US008114975B2

(12) United States Patent
Samelson et al.

(10) Patent No.: US 8,114,975 B2
(45) Date of Patent: Feb. 14, 2012

(54) PROTEIN TYROSINE KINASE SUBSTRATE LAT AND ITS USE IN THE IDENTIFICATION OF (ANT) AGONISTS OF THE KINASE

(75) Inventors: Lawrence E. Samelson, Chevy Chase, MD (US); Weiguo Zhang, Chapel Hill, NC (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 11/218,020

(22) Filed: Aug. 31, 2005

(65) Prior Publication Data

US 2006/0073562 A1 Apr. 6, 2006

Related U.S. Application Data

(60) Division of application No. 09/597,920, filed on Jun. 19, 2000, now Pat. No. 7,118,889, which is a continuation of application No. PCT/US98/27400, filed on Dec. 23, 1998.

(60) Provisional application No. 60/068,690, filed on Dec. 23, 1997.

(51) Int. Cl.
*C07H 21/04* (2006.01)

(52) U.S. Cl. ...................... 536/23.5; 536/24.3

(58) Field of Classification Search ........................ None
See application file for complete search history.

(56) References Cited

U.S. PATENT DOCUMENTS

| 4,016,043 | A | 4/1977 | Schuurs et al. |
|---|---|---|---|
| 4,018,653 | A | 4/1977 | Mennen |
| 4,424,279 | A | 1/1984 | Bohn et al. |
| 4,683,195 | A | 7/1987 | Mullis et al. |
| 4,683,202 | A | 7/1987 | Mullis |
| 5,608,039 | A | 3/1997 | Pastan et al. |
| 5,652,096 | A | 7/1997 | Cimino |
| 6,180,370 | B1 | 1/2001 | Queen et al. |

OTHER PUBLICATIONS

Zhang et al., Cell 92 (1), 83-92 (1998).*
Yamauchi et al., DNA Research 1995, vol. 2, pp. 269-275.*
Genbank accession No. AA380490.1 entitled "EST93460 Supt cells *Homo sapiens* cDNA 5- end, mRNA sequence", Apr. 21, 1997, pp. 1-2.*
Peter Goodfellow, Nature. Sep. 28, 1995;377(6547):285-6.*
Walter et al., Nat Genet. May 1994;7(1):22-8.*
Plasmid map for pBlueScript Sk-, obtained from http://www.lablife.org/p?a=vdb_view&id=g2.CA.17q8U5a0JuLII0gsSTm4jKLo—on Apr. 12, 2011, 2 pages.*
Turner et al., "Perinatal lethality and blocked B-cell development in mice lacking the tyrosine kinase Syk," *Nature* 378:298-302 (1995).
Arpaia et al., "Defective T cell receptor signaling and CD8+ thymic selection in humans lacking ZAP-70 kinase," *Cell* 76:947-958 (1994).
Chan et al., "ZAP-70 deficiency in an autosomal recessive form of severe combined immunodeficiency," *Science* 264:1599-1601 (1994).

Elder et al., "Human severe combined immunodeficiency due to a defect in ZAP-70, a T cell tyrosine kinase," *Science* 264:1596-1599 (1994).
Negishi et al., "Essential role for ZAP-70 in both positive and negative selection of thymocytes," *Nature* 376:435-438 (1995).
Chan et al., "ZAP-70: a 70 kd protein-tyrosine kinase that associates with the TCE ζ chain," *Cell* 71:649-662 (1992).
Watts et al., "Identification by electrospray ionization mass spectrometry of the sites of tyrosine phosphorylation induced in activated Jurkat T cells on the protein tyrosine kinase ZAP-70," *J. Biol. Chem.* 269:29520-29529 (1994).
Guanghui et al. "Distinct tyrosine phosphorylation sites within ZAP-70 mediate activation and negative regulation of antigen receptor function," *Mol. Cell. Biol.* (1996).
Chan et al., "Activation of ZAP-70 kinase activity by phosphorylation of tyrosine 493 is required for lymphocyte antigen receptor function," *EMBO J.* 14:2499-2508 (1995).
Wange et al., "Activating and inhibitory mutations in adjacent tyrosines in the kinase domain of ZAP-70," *J. Biol. Chem.* 270:18730-18733 (1995).
Wange et al., "Tandem SH2 domains of ZAP-70 bind to T cell antigen receptor and CD3 from activated Jurkat T cells," *J. Biol.Chem.* 268:19797-19801 (1993).
Iwashima et al., "Sequential interactions of the TCR with two distinct cytoplasmic tyrosine kinases," *Science* 263:1136-1139 (1994).
Wange et al., "F2(Pmp)2-TAM 3, a novel competitive inhibitor of the binding of ZAP-70 to the T cell antigen receptor, blocks early T cell signaling," *J. Biol. Chem.* 270:944-948 (1995).
Qian et al., "Dominant-negative Zeta-associated Protein 70 Inhibits T Cell Antigen Receptor Signaling," *J. Exp. Med.* 183:611-620 (1996).
van Oers et al., "Constitutive tyrosine phosphorylation of the T-cell receptor (TCR) subunit: regulation of TCR-associated protein tyrosine kinase activity by TCR ζ," *Mol. Cell. Biol.* 13:5771-5780 (1993).
Wiest et al., "TCR activation of ZAP-70 is impaired in CD4+CD8+ thymocytes as a consequence of intrathymic interactions that diminish available p56lck," *Immunity* 4:495-504 (1996). Desiderio et al., "The Itk/Btk/Tec Family of Protein-Tyrosine Kinases," *Chem. Immunol.* 59:191-208 (1994).
Liao et al., "Altered T cell receptor signaling and disrupted T cell development in mice lacking Itk," *Immunity* 3:757-769 (1995).
Gibson et al., "The EMT/ITK/TSK (EMT) tyrosine kinase is activated during TCR signaling," *J. Immunol.* 156:2716-2722 (1996).
Bustelo et al., "Product of the Vav protooncogene defines a new class of tyrosine protein kinase substrates," *Nature* 356: 68-74 (1992).
Donovan et al., "The protein product of the c-cbl protooncogene is the 120-kDa tyrosine-phosphorylated protein in Jurkat cells activated via the T cell antigen receptor," *J. Biol. Chem.* 269:22921-22924 (1994).
Jackman et al., "Molecular cloning of SLP-76, a 76-kDa tyrosine phosphoprotein associated with Grb2 in T cells," *J. Biol. Chem.* 270:7029-7032 (1995).
Harrison et al., "Phosphorylation of human erythrocyte band 3 by endogenous p72syk," *J. Biol. Chem.* 269:955-959 (1994).
Peters et al., "Syk, activated by cross-linking the B-cell antigen receptor, localizes to the cytosol where it interacts with and phosphorylates alpha-tubulin on tyrosine," *J. Biol. Chem.* 271:4755-4762 (1996).

(Continued)

*Primary Examiner* — Zachary Skelding
(74) *Attorney, Agent, or Firm* — Edwards Wildman Palmer LLP; Peter F. Corless; Christine C. O'Day

(57) ABSTRACT

The invention generally relates to compositions and methods for identifying and testing tyrosine kinase signaling pathway agonists and antagonists, and more particularly, methods and compositions for screening compounds and identifying compounds that will modulate the interaction of protein tyrosine kinase substrates with their intracellular ligands, as well as between their intracellular ligands and other members of the signaling pathway.

20 Claims, 34 Drawing Sheets

OTHER PUBLICATIONS

Ley et al., "Tyrosine phosphorylation of tubulin in human T lymphocytes," *Eur. J. Immunol.*, 24:99-106 (1994).
Huby et al., "Interactions between the Protein-tyrosine Kinase ZAP-70, the Proto-oncoprotein Vav, and Tubulin in Jurkat T Cells," *J. Biol. Chem.*, 270:30241-30244 (1995).
Wardenburg et al., "Phosphorylation of SLP-76 by the ZAP-70 protein tyrosine kinase is required for T cell receptor function," *J. Biol. Chem.*, in press (1996).
Wu et al., "Vav and SLP-76 interact and functionally cooperate in IL-2 gene activation," *Immunity* 4:593-602 (1996).
Fusaki et al., "Physical and functional interactions of protein tyrosine kinases, p59fyn and ZAP-70, in T cell signaling," *J. Immunol.* 156:1369-1377 (1996).
Vogel et al., "The SH3 domain of p56lck is involved in binding to phosphatidylinositol 3'-kinase from T lymphocytes," *Mol. Cell. Biol.*, 13:7408-7417 (1993).
Thome et al., "Syk and ZAP-70 mediate recruitment of p56lck/CD4 to the activated T cell receptor/CD3/ complex," *J. Exp. Med.*, 181:1997-2006 (1995).
Hatada et al., "Molecular basis for interaction of the protein tyrosine kinase ZAP-70 with the T-cell receptor," *Nature* 377:32-38 (1995).
Shiue et al., "Syk is activated by phosphotyrosine-containing peptides representing the tyrosine-based activation motifs of the high affinity receptor for IgE," *J. Biol. Chem.* 270:10498-10502 (1995).
Neumeister et al., "Binding of ZAP-70 to phosphorylated T-cell receptor and enhances its autophosphorylation and generates specific binding sites for SH2 domain-containing proteins," *Mol. Cell. Biol.* 15:3171-3178 (1995).
Isakov et al., "Purification and characterization of human ZAP-70 protein tyrosine kinase from a baculovirus expression system," *J. Biol. Chem.* 271:15753-15761 (1996).
Katzav et al., "The protein tyrosine kinase ZAP-70 can associate with the SH2 domain of proto-vav," *J. Biol. Chem.* 269:32579-32585 (1994).
Foumel et al., "Association of tyrosine protein kinase ZAP-70 with the protooncogene product p120c-cbl in T lymphocytes," *J. Exp. Med.* 183:301-306 (1996).
Downward, "The GRB2/Sem-5 adaptor protein," *FEBS Lett.* 338:113-117 (1994).
Meisner et al., "Interaction of Cbl with Grb2 and Phosphatidylinositol-3'-Kinase in Activated Jurkat Cells," *Mol. Cell Biol.* 15:3571-3578 (1995).
Holsinger et al., "Signal transduction in T lymphocytes using a conditional allele of Sos," *Proc. Natl. Acad. Sci. USA* 92:9810-9814 (1995).
Ravichandran et al., "Interaction of Shc with Grb2 regulates association of Grb2 with mSOS," *Mol. Cell. Biol.* 15:593-600 (1995).
Osman et al., "A comparison of the interaction of Shc and the tyrosine kinase ZAP-70 with the T cell antigen receptor chain tyrosine-based activation motif," *J. Biol. Chem.* 270:13981-13986 (1995).
Motto et al., "In vivo association of Grb2 with pp116, a substrate of the T cell antigen receptor-activated protein tyrosine kinase," *J. Biol. Chem.* 269:21608-21613 (1994).
Buday et al., "A complex of Grb2 adaptor protein, Sos exchange factor, and a 36-kDa membrane-bound tyrosine phosphoprotein is implicated in ras activation in T cells," *J. Biol. Chem.* 269:9019-9023 (1994).
Reif et al., "SH3 domains of the adapter molecule Grb2 compete with two proteins in T cells: the guanine nucleotide exchange protein SOS and a 75-kDa protein that is a substrate for T cell antigen receptor-activated tyrosine kinases," *J. Biol. Chem.* 269:14081-14087 (1994).
Fukazawa et al., "T cell activation-dependent association between the p85 subunit of the phosphatidyl 3-kinase and Grb2/phospholipase C-γ1-binding phosphotyrosyl protein," *J. Biol. Chem.* 270:36-38, 20177-20182 (1995).
Liu et al., "Activation-modulated association of 14-3-3 proteins with Cbl in T cells," *J. Biol. Chem.* 271:14591-14595 (1996).
Reedquist et al., "Stimulation through the T cell receptor induces Cbl association with Crk proteins and guanine nucleotide exchange protein C3G," *J. Biol. Chem.* 271:8435-8442 (1996).

Motto et al., "Implications of the GRB2-associated phosphoprotein SLP-76 in T cell receptor-mediated interleukin 2 production," *J. Exp. Med.* 183:1937-1943 (1996).
McFarland et al., "Protein tyrosine phosphatases involved in lymphocyte signal transduction," *Chem. Immunol.* 59:40-61 (1994).
Plas et al., "Direct regulation of ZAP-70 by SHP-1 in T cell antigen receptor signaling," *Science* 272:1173-1176 (1996).
Kon-Kozlowski et al., "The tyrosine phosphatase PTP1C associates with Vav, Grb2, and mSos1 in hematopoietic cells," *J. Biol. Chem.* 271:3856-3862 (1996).
Marengere et al., "Regulation of T cell receptor signaling by tyrosine phosphatase SYP association with CTLA-4," *Science* 272:1170-1173 (1996).
Douillard and Hoffman, Basic Facts about Lymphocyte Hybridomas, in *Compendium of Immunology* vol. II, ed. by Schwartz, 1981.
Kohler and Milstein, "Continuous cultures of fused cells secreting antibody of predefined specificity," *Nature* 256: 495-497 (1975).
Kohler and Milstein, "Derivation of specific antibody-producing tissue culture and tumor lines by cell fusion," *Euro. J. of Immunology* 6: 511-519 (1976).
Reading, "Theory and Methods for Immunization in Culture and Monoclonal Antibody Production," *J. of Immuno. Meth.* 53: 261-291, 1982.
Sambrook et al., Molecular Cloning: A Laboratory Manual, 2d ed. (1989) Cold Spring Harbor Laboratory Press, Cold Spring Harbor, N.Y.
Current Protocols in Molecular Biology (1996) John Wiley and Sons, Inc., N.Y.
Sinha et al., "Polymer support oligonulcoetide synthesis XVIII$^{(1,2)}$: use of β-cyanoethyl-N,N-dialkylamino-/N-morpholino phosphoramidite of deoxynucleosides for the synthesis of DNA fragments simplifying deprotection and islation of the final product," *Nuc. Acids Res.* 12:4539 (1984).
Samelson et al., "Association of the fyn protein-tyrosine kinase with the T-cell antigen receptor," *Proc. Natl. Acad. Sci. USA* 87:4358-4362 (1990).
Kung et al., "Monoclonal antibodies defining distinctive human T cell surface anigens," *Science* 206:347-349 (1979).
Mizushima et al., "pEF-BOS, a powerful mammalian expression vector," *Nuc. Acids Res.* 18:5322 (1990).
Seed, "An LFA-3 cDNA encodes a phospholipid-linked membrane protein homologous to its receptor CD2," *Nature* 329:840-842 (1987).
Nagata et al., "Molecular cloning and expression of cDNA for human granulocyte colony-stimulating factor," Nature 319: 415-418 (1986).
Uetsuki et al., "Isolation and Characterization of the Human Chromosomal Gene for Polypeptide Chain Elongation Factor-1α," *J. Biol. Chem.*, 264:5791-5798 (1989).
Spencer et al., "Controlling signal transduction with synthetic ligands." *Science* 262:1019-1024 (1993).
Berger et al., "Secreted placental alkaline phosphatase: a powerful new quantitative indicator of gene expression in eukaryotic cells," *Gene* 66:1-10 (1988).
Sloan-Lancaster et al., "Regulation of ZAP-70 intracellular localization: visualization with the green fluorescent protein," *J. Exp. Med.* 186:1713-1724 (1997).
Zhang et al., "LAT: the ZAP-70 tyrosine kinase substrate that links T cell receptor to cellular activation," *Cell* 92:83-92 (1998).
Songyang et al., "Specific motifs recognized by the SH2 domains of Csk, 3BP2, fps/fes, GRB-2, HCP, SHC, Syk and Vav," *Mol. Cell. Biol.* 14:2777-2785 (1994).
Alland et al., "Dual myristylation and palmitoylation of Src family member p59$^{fyn}$ affects subcellular localization," *J. Biol. Chem.* 269:16701-16705 (1994).
Shenoy-Scaria et al., "Cysteine of Src family protein tyrosine kinases determines palmitoylation and localization in caveolae" *J. Cell Biol.* 126:353-363 (1994).
Simons and Ikonen, "Functional rafts in cell membranes" *Nature* 387:569-572 (1997).
Brown and Rose, "Sorting of GPI-anchored proteins to glycolipid-enriched membrane subdomains during transport to the apical cell surface" *Cell* 68:533-544 (1992).

Marth et al., "Lymphocyte activation provokes modification of a lymphocyte-specific protein tyrosine kinase (p56*lck*)," *J. Immunol.* 142:2430-2437 (1989).

Clipstone and Crabtree, "Identification of calcineurin as a key signaling enzyme in T-lymphocyte activation" Nature 357:695-697 (1992).

Sieh et al., "Grb2 and phospholipase C-gammal associate with a 36- to 38-kilodalton phosphotyrosine protein after T-cell receptor stimulation," *Mol. Cell. Biol.* 14:4435-42 (1994).

Weber et al., "Molecular cloning of the cDNA encoding pp36, a tyrosine-phosphorylated adapter protein selectively expressed by T cells and natural killer cells," *J. Exp. Med.* 187:1157-61 (1998).

Zhang et al., "LAT: the ZAP-70 tyrosine kinase substrate that links T cell receptor to cellular activation," Cell 92:83-92 (1998).

Huang et al., "Cloning and characterization of Lnk, a signal transduction protein that links T-cell receptor activation signal to phospholipase $C\gamma_1$, Grb2, and phosphatidylinositol 3-kinase," Proc. Natl. Acad. Sci. USA 92:11618.

Weiss et al., "Signal transduction by lymphocyte antigen receptors," *Cell* 76:263-274 (1994).

Cantrell, "T Cell Antigen Receptor Signal Transduction Pathways," *Annu. Rev. Immunol.*, 14:259-274 (1996).

Marmur and Lane, "Strand Separation and Specific Recombination in Deoxyribonucleic Acids: Biological Studies," *Proc. Natl. Acad. Sci. USA* 46:453 (1960).

Doty et al., "Strand Separation and Specific Recombination in Deoxyribonucleic Acids: Physical Chemical Studies," *Proc. Natl. Acad. Sci. USA* 46:461 (1960).

Wallace et al., (1985) "Application of synthetic oligonucleotides to the diagnosis of human genetic diseases," *Biochimie* 67:755-762.

Studencki and Wallace, "Allele-Specific Hybridization Using Olignucleotide Probes of Very High Specific Activity: Discrimination of the Human $\beta^A$- and $\beta^S$-Globin Genes," *DNA* 3:7-15 (1984).

Studencki et al., (1985) "Discrimination Among the Human, $\beta^A$, $\beta^S$, and $\beta^C$-Globin Genes Using Allele-Specific Oligonucleotide Hybridization Probes," *Human Genetics* 37:42-51.

Smith and Waterman, "Comparison of Biosequences," *Adv. Appl. Math.* 2:482-489 (1981).

Needleman and Wunsch, "A General Method Applicable to the Search for Similarities in the Amino Acid Sequence of Two Proteins," *J. Mol. Biol.* 48:443-453 (1970).

Pearson and Lipman, "Improved Tools for Biological Sequence Comparison," *Proc. Natl. Acad. Sci. USA* 85:2444 (1988).

Exley et al., "Association of phosphatidylinositol-3-kinase with a specific sequence of the T cell receptor chain is dependent on T cell activation", *J. Biol. Chem.* 269:15140-15146 (1994).

Cambior et al., "Differential binding activity of ARH1/TAM motifs," *Immunol. Lett.* 44:77-40 (1995).

Isakov et al., "ZAP-70 binding specificity to T cell receptor tyrosine-based activation motifs: the tandem SH2 domains of ZAP-70 bind distinct tyrosine-based activation motifs with varying affinity," *J. Exp. Med.* 181:375-380 (1995).

Osman et al., "The protein interactions of the immunoglobulin receptor family tyrosine-based activation motifs present in the T cell receptor subunits and the CD3, and chains," *Eur. J. Immunol.* 26:1063-1068 (1996).

Caplan et al., "Cell-surface expressed T-cell antigen-receptor chain is associated with the cytoskeleton," *Proc. Natl. Acad. Sci. USA* 92:4768-4772 (1995).

Rozdzial et al., Tyrosine-phosphorylated T cell receptor chain associates with actin cytoskeleton upon activation of mature T lymphocytes, *Immunity* 3:623-633 (1995).

Bolen et al., "Nonreceptor tyrosine protein kinases," *Oncogene* 8:2025-2031 (1993).

Peri et al., "Tyrosine protein kinases in T lymphocytes," *Chem. Immunol.* 59:19-39 (1994).

Jayaraman et al., "Regulation of the Inositol 1,4,5-trisphosphate receptor by tyrosine phosphorylation," *Science* 272:1492-1494 (1996).

Cheng et al., "Syk tyrosine kinase required for mouse viability and B-cell development," *Nature* 378:303-306 (1995).

Fargnoli et al., "Syk mutation in Jurkat E6-derived clones results in lack of p72syk expression," *J Biol. Chem.* 270:26533-26537 (1995).

* cited by examiner

| Expt | Peak | Mass | Sequence | Source |
|---|---|---|---|---|
| 1 | 40 | 1721.9 | x x v N V S Q E L H P x A A k | LAT |
| 1 | 82 | 1840.0 | S E V L G W D P D S L A D Y F K | SLP-76 |
| 2 | 31 | n.d. | S I F T R | SLP-76 |
| 3 | 55 | 1334.8 | n.d. | SLP-76 |
| 3 | 48 | 1743.3 | L P G S Y D S T S S D S L Y P R | LAT |
| 3 | 48 | 1641.6 | x Y v N V | LAT |

INPUT DNA:
| | | | | | | | | |
|---|---|---|---|---|---|---|---|---|
| LAT-FLAG | − | + | + | + | + | + | + | + | + |
| Lck | | | | | + | +* | | + | |
| Fyn | | | | | | | + | | + |
| ZAP-70 | | + | | | | | | + | + |
| Syk | | | + | | | | | | |
BLOT: ANTI-pY
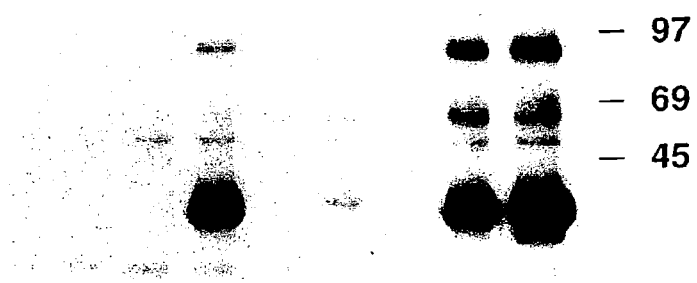
— 97
— 69
— 45
BLOT: ANTI-Grb2
BLOT: ANTI-FLAG
FIG. 4A

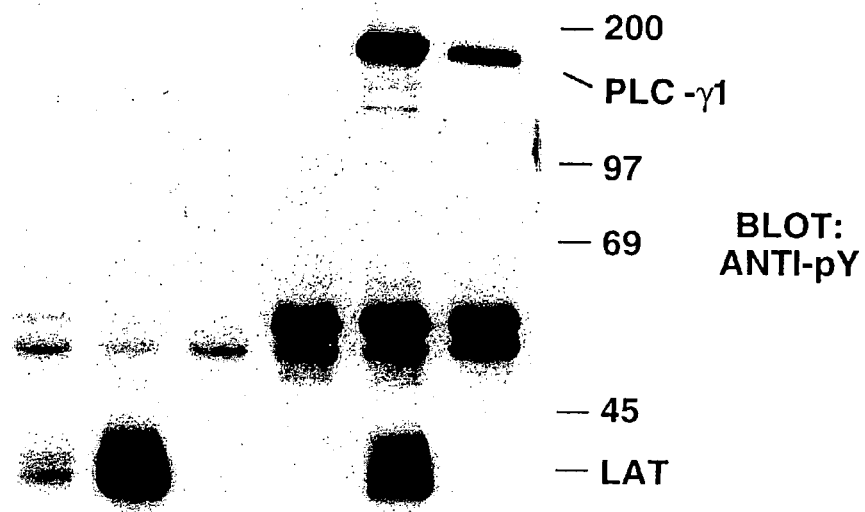
FIG. 5B

Human LAT Nucleotide Sequence (1-1060)

```
  1 gactctgccc ttgaggggcc taggggtgca gccagcctgc tccgagctcc cctgcagatg
 61 gaggaggcca tcctggtccc ctgcgtgctg gggctcctgc tgctgcccat cctggccatg
121 ttgatggcac tgtgtgtgca ctgccacaga ctgccaggct cctacgacag cacatcctca
181 gatagtttgt atccaagggg catccagttc aaacggcctc acacggttgc cccctggcca
241 cctgcctacc cacctgtcac ctcctaccca ccctgagcc agccagacct gctccccatc
301 ccaagatccc cgcagccct tggggctcc caccggacgc catcttcccg gcgggattct
361 gatggtgcca acagtgtggc gagctacgag aacgaggaac cagcctgtga ggatgcagat
421 gaggatgagg acgactatca cacccaggc tacctggtgg tgcttcctga cagcacccg
481 gccactagca ctgctgcccc atcagctcct gcactcagca ccctggcat ccgagacagt
541 gccttctcca tggagtccat tgatgattac gtgaacgttc cggagagcgg ggagagcgca
601 gaagcgtctc tggatggcag ccgggagtat gtgaatgtgt cccaggaact gcatcctgga
661 gcggctaaga ctgagcctgc cgccctgagt tcccaggagg cagaggaagt ggaggaagag
721 ggggctccag attacgagaa tctgcaggag ctgaactgag ggctgtgga ggccgagtct
781 gtcctggaac caggcttgcc tgggacggct gagctgggca gctggaagtg gctctggggt
841 cctcacatgg cgtcctgccc ttgctccagc ctgacaacag cctgagaaat cccccgtaa
901 cttattatca ctttgggggtt cggcctgtgt ccccgaacg ctctgcacct tctgacgcag
961 cctgagaatg acctgccctg gccccagccc tactctgtgt aatagaataa aggcctgcgt
1021 gtgtctgtgg aaaaaaaaaa aaaaaaaaaa aaaaaaaaa
```

Figure 7A

Human LAT Nucleotide Sequence (1-1460), [alternative splice variant]

```
   1 accccatctt catctggcct tgactctgcc cttgaggggc ctaggggtgc agccagcctg
  61 ctccgagctc ccctgcagat ggaggaggcc atcctggtcc cctgcgtgct ggggctcctg
 121 ctgctgccca tcctggccat gttgatggca ctgtgtgtgc actgccacag actgccaggc
 181 tcctacgaca gcacatcctc agatagtttg tatccaaggg gcatccagtt caaacggcct
 241 cacacggttg cccctggcc acctgcctac ccacctgtca cctcctaccc accctgagc
 301 cagccagacc tgctccccat cccaagatcc ccgcagcccc ttggggctc ccaccggacg
 361 ccatcttccc ggcgggattc tgatggtgcc aacagtgtgg cgagctacga gaacgagggt
 421 gcgtctggga tccgaggtgc ccaggctggg tggggagtct ggggtccgtc ctggactagg
 481 ctgacccctg tgtcgttacc cccagaacca gcctgtgagg atgcagatga ggatgaggac
 541 gactatcaca acccaggcta cctggtggtg cttcctgaca gcaccccggc cactagcact
 601 gctgcccat cagctcctgc actcagcacc cctggcatcc gagacagtgc cttctccatg
 661 gagtccattg atgattacgt gaacgttccg gagagcgggg agagcgcaga agcgtctctg
 721 gatggcagcc gggagtatgt gaatgtgtcc caggaactgc atcctggagc ggctaagact
 781 gagcctgccg ccctgagttc ccaggaggca gaggaagtgg aggaagaggg ggctccagat
 841 tacgagaatc tgcaggaggct gaactgaggg cctgtggagg ccgagtctgt cctggaacca
 901 ggcttgcctg ggacggctga gctgggcagc tggaagtggc tctggggtcc tcacatggcg
 961 tcctgccctt gctccagcct gacaacagcc tgagaaatcc ccccgtaact tattatcact
1021 ttggggttcg gcctgtgtcc cccgaacgct ctgcaccttc tgacgcagcc tgagaatgac
1081 ctgccctggc cccagcccta ctctgtgtaa tagaataaag gcctgcgtgt gtctgtgttg
1141 agcgtgcgtc tgtgtgtgcc tgtgtgcgag tctgagtcag agatttggag atgtctctgt
1201 gtgtttgtgt gtatctgtgg gtctccatcc tccatggggg ctcagccagg tgctgtgaca
1261 ccccccttct gaatgaagcc ttctgacctg ggctggcact gctgggggtg aggacacatt
1321 gccccatgag acagtcccag aacacggcag ctgctggctg tgacaatggt ttcaccatcc
1381 ttagaccaag ggatgggacc tgatgacctg ggaggactct tttagttctt acctcttgtg
1441 gttctcaata aaacagaacg
```

Figure 7B

Murine LAT Nucleotide Sequence (1-1260)

```
   1 ggcacgagca ggcggggagc aagaaagggg caggtacagc tgggcacggg gatcgtgcag
  61 ctggtagctg gggcacgggc cccagctctg gctctggggc gagcaccttt ccagagccaa
 121 cactgctctc aactcagtcc agcaagagag gggagccatc cagccccgaa aggatacggc
 181 tgcctactgc cgggcggatc ccaggctgga gcccgcttgg tcccatacct ctgctgccac
 241 tctgtctcga ggggctgcag tgcagcaggg cctgtggcag gtgctctgca gatggaagca
 301 gacgccttga gcccggtggg gctgggcctc ctgctgctgc ccttcttggt cacgctcctg
 361 gctgccctgt gcgtgcgctg ccgtgagttg ccagtctcct atgacagcac ttccacagag
 421 agtttgtacc caagaagcat cctcatcaag ccacctcaaa taaccgtccc ccgaacacct
 481 gctgtttcct accctctagt cacttccttc ccacccctga ggcagccaga cctgctcccc
 541 atcccgagat ccccacagcc ccttgggggt tcccatcgga tgccatcttc ccagcagaat
 601 tcagatgatg ccaacagtgt ggcaagctac gagaaccagg agccagcctg taagaatgtg
 661 gatgcagatg aggatgaaga cgactatccc aacggctacc tagtggtgct gcctgacagt
 721 agtcctgctg ccgtccctgt tgtctcctct gctcctgtgc ctagcaaccc tgaccttgga
 781 gacagtgcct tctctgtgga gtcgtgtgaa gattacgtga atgttcctga gagtgaggag
 841 agcgcagagg cgtctctgga tgggagccgg gagtatgtga atgtgtcccc agagcagcag
 901 ccagtgacca gggctgagct ggcctctgtg aactcccagg aggtggaaga cgaaggagaa
 961 gaggaagggg tggatggaga ggaagctccc gactatgaga atctacagga gcttaactga
1021 aagcctactg cagctgtctg tcctgaaact ggacttgctg gggtgtcgct aagaggatcc
1081 catttgatct ctgccttgcc acagcctgag aatcttcccc taacttattg tcactttggg
1141 gtccagtctg tgtccccaat attctgtacc ttctgataaa gcctgagaat gaatctggtt
1201 ccagccagac catgtcatgg aataaaggcc atgtgacata aaaaaaaaaa aaaaaaaaa
```

Figure 7C

```
human LAT    1   MEEAILVPCVLGLLLPIL.AMLMALCVHCHRLPGSDSTSSDSLPRGI   49
                 ||||:|||:|||||||||:||||||:||||:|||||||||||||:|||
murine LAT   1   MEADALSPVGLGLLLLPFLVTLLAALCVRCRELPVSDSTSTESLPRSI   50

50   QFKRPHTVAPWPPA...PPVTSYPPLSQPDLLPIPRSPQPLGGSHRTPSS   97
                 ::|||||:|||||    ||||:|||||:|||||||||:|||||:|||
            51   LIKPPQITVPRTPAVSPLVTSFPPLRQPDLLPIPRSPQPLGGSHRMPSS  100

98   RRDSDGANSVASENEEPACE..DADEDEDDHNPGLVVLPDSTPATST   145
                 :::||:|||||||:|::|||  |||||||||| :|:||||||:|||:
           101   QQNSDDANSVASENQEPACKNVDADEDEDDPN.GLVVLPDSSPAAVP   149

146   AAPSAPALSTPGIRDSAFSMESIDDVNVPESGESAEASLDGSREVNVS   195
                 .  ||||||:|||||||||||||||||||::|||||||||||||||||
           150   VVSSAPVPSNPDLGDSAFSVESCEDVNVPESEESAEASLDGSREVNVS   199

196   QELHPGAAKTEPAALSSQEAEE......VEEEGAPDENLQELN       233
                 ::|:|||:|:|::  :|:|:    :||::|||||||||||
           200   PEQQP.VTRAELASVNSQEVEDEGEEEGVDGEEAPDENLQELN       242
```

FIG. 7D

1 ggaataggtt agtttcagac aagcctgctt gccggagctc agcagacacc aggccttccg
61 ggcaggcctg gcccaccgtg ggcctcagag ctgctgctgg ggcattcaga accggctctc
121 cattggcatt gggaccagag accccgcaag tggcctgttt gcctggacat ccacctgtac
181 gtccccaggt ttcgggaggc ccaggggcga tgccagaccc cgcggcgcac ctgcccttct
241 tctacggcag catctcgcgt gccgaggccg aggagcacct gaagctggcg ggcatggcgg
301 acgggctctt cctgctgcgc cagtgcctgc gctcgctggg cggctatgtg ctgtcgctcg
361 tgcacgatgt gcgcttccac cactttccca tcgagcgcca gctcaacggc acctacgcca
421 ttgccggcgg caaagcgcac tgtggaccgg cagagctctg cgagttctac tcgcgcgacc
481 ccgacgggct gccctgcaac ctgcgcaagc cgtgcaaccg gccgtcgggc ctcgagccgc
541 agccgggggt cttcgactgc ctgcgagacg ccatggtgcg tgactacgtg cgccagacgt
601 ggaagctgga gggcgaggcc ctggagcagg ccatcatcag ccaggccccg caggtggaga
661 agctcattgc tacgacggcc cacgagcgga tgccctggta ccacagcagc ctgacgcgtg
721 aggaggccga gcgcaaactt tactctgggg cgcagaccga cggcaagttc ctgctgaggc
781 cgcggaagga gcagggcaca tacgccctgt ccctcatcta tgggaagacg gtgtaccact
841 acctcatcag ccaagacaag gcgggcaagt actgcattcc cgagggcacc aagtttgaca
901 cgctctggca gctggtggag tatctgaagc tgaaggcgga cgggctcatc tactgcctga
961 aggaggcctg ccccaacagc agtgccagca acgcctcagg ggctgctgct cccacactcc
1021 cagcccaccc atccacgttg actcatcctc agagacgaat cgacaccctc aactcagatg
1081 gatacacccc tgagccagca cgcataacgt ccccagacaa accgcggccg atgcccatgg
1141 acacgagcgt gtatgagagc ccctacagcg acccagagga gctcaaggac aagaagctct
1201 tcctgaagcg cgataacctc ctcatagctg acattgaact tggctgcggc aactttggct
1261 cagtgcgcca gggcgtgtac cgcatgcgca agaagcagat cgacgtggcc atcaaggtgc
1321 tgaagcaggg cacggagaag gcagacacgg aagagatgat gcgcgaggcg cagatcatgc
1381 accagctgga caacccctac atcgtgcggc tcattggcgt ctgccaggcc gaggccctca
1441 tgctggtcat ggagatggct gggggcgggc cgctgcacaa gttcctggtc ggcaagaggg
1501 aggagatccc tgtgagcaat gtggccgagc tgctgcacca ggtgtccatg ggatgaagt
1561 acctggagga gaagaacttt gtgcaccgtg acctggcggc ccgcaacgtc ctgctggtta
1621 accggcacta cgccaagatc agcgactttg gcctctccaa agcactgggt gccgacgaca
1681 gctactacac tgcccgctca gcagggaagt ggccgctcaa gtggtacgca cccgaatgca
1741 tcaacttccg caagttctcc agccgcagcg atgtctggag ctatggggtc accatgtggg
1801 aggccttgtc ctacggccag aagccctaca agaagatgaa agggccggag gtcatggcct
1861 tcatcgagca gggcaagcgg atggagtgcc caccagagtg tccacccgaa ctgtacgcac
1921 tcatgagtga ctgctggatc tacaagtggg aggatcgccc cgacttcctg accgtggagc
1981 agcgcatgcg agcctgttac tacagcctgg ccagcaaggt ggaagggccc ccaggcagca
2041 cacagaaggc tgaggctgcc tgtgcctgag ctcccgctgc ccaggggagc cctccacgcc
2101 ggctcttccc caccctcagc cccaccccag gtcctgcagt ctggctgagc cctgcttggt
2161 tgtctccaca cacagctggg ctgtggtagg gggtgtctca ggccacaccg gccttgcatt
2221 gcctgcctgg ccccctgtcc tctctggctg gggagcaggg aggtccggga gggtgcggct
2281 gtgcagcctg tcctgggctg gtggctcccg gagggccctg agctgagggc attgcttaca
2341 cggatgcctt cccctgggcc ctgacattgg agcctgggca tcctcaggtg gtcaggcgta
2401 gatcaccaga ataaacccag cttccctctt gaaaaaaaaa aaaaaaaaaa aacc Human ZAP-70 Nucleotide Sequence (1-2454)

Figure 8A

```
  1 mpdpaahlpf fygsisraea eehlklagma dglfllrqcl rslggyvlsl vddvrfhhfp
 61 ierqlngtya iaggkahcgp aelcqfysqd pdglpcnlrn acnrppglep qpgvfdclrd
121 amvrdyvrqt wklegdaleq aiisqapqve kliattaher mpwyhssltr eeaerklysg
181 qqtdgkfllr prkeqgtyal slvygktvyh ylisqdkagk ycipegtkfd tlwqlveylk
241 lkadgliyrl kevcpnssas aavaaptlpa hpstftqpqr rvdtlnsdgy tpeparlass
301 tdkprpmpmd tsvyespysd peelkdkklf lkrenllvad ielgcgnfgs vrqgvyrmrk
361 kqidvaikvl kqgtekadkd emmreaqimh qldnpyivrl igvcqaealm lvmemagggp
421 lhkfllgkke ipvsnvaell hqvamgmkyl eeknfvhrdl aarnvllvnr hyakisdfgl
481 skalgaddsy ytarsagkwp lkwyapecin frkfssrsdv wsygvtmwea fsygqkpykk
541 mkgpevldfi kqgkrmecpp ecppemyalm sdcwiykwed rpdfltveqr mrnyyyslas
601 raegppqceq vaeaacg
```

Human ZAP-70 Amino Acid Sequence (1-617)

Figure 8B

```
   1 gaggaagagc cgcgggcccg gcggctgagg ccacccggc ggcggctgga gagcgaggag
  61 gagcgggtgg ccccgcgctg cgcccgccct cgcctcacct ggcgcaggtg gacacctgcg
 121 caggtgtgtg ccctccggcc cctgaagcat ggccagcagc ggcatggctg acagcgccaa
 181 ccacctgccc ttcttttcg gcaacatcac ccgggaggag gcagaagatt acctggtcca
 241 gggggcatg agtgatgggc tttatttgct gcgccagagc cgcaactacc tgggtggctt
 301 cgccctgtcc gtggcccacg ggaggaaggc acaccactac accatcgagc gggagctgaa
 361 tggcacctac gccatcgccg gtggcaggac ccatgccagc cccgccgacc tctgccacta
 421 ccactcccag gagtctgatg gcctggtctg cctcctcaag aagcccttca accggcccca
 481 aggggtgcag cccaagactg ggcccttga ggatttgaag gaaaacctca tcagggaata
 541 tgtgaagcag acatggaacc tgcagggtca ggctctggag caggccatca tcagtcagaa
 601 gcctcagctg gagaagctga tcgctaccac agcccatgaa aaaatgcctt ggttccatgg
 661 aaaaatctct cgggaagaat ctgagcaaat tgtcctgata ggatcaaaga caaatggaaa
 721 gttcctgatc cgagccagag acaacaacgg ctcctacgcc ctgtgcctgc tgcacgaagg
 781 gaaggtgctg cactatcgca tcgacaaaga caagacaggg aagctctcca tccccgaggg
 841 aaagaagttc gacacgctct ggcagctagt cgagcattat tcttataaag cagatggttt
 901 gttaagagtt cttactgtcc catgtcaaaa aatcggcaca cagggaaatg ttaattttgg
 961 aggccgtcca caacttccag gttcccatcc tgcgtcctcc cctgcccaag ggaaccggca
1021 agagagtact gtgtcattca atccgtatga gccagaactt gcaccctggg ctgcagacaa
1081 aggcccccag agagaagccc tacccatgga cacagaggtg tacgagagcc cctacgcgga
1141 ccccgaggag atcaggccca aggaggttta cctggaccga aagctgctga cgctggaaga
1201 caaagaactg ggctctggta attttggaac tgtgaaaaag ggctactacc aaatgaaaaa
1261 agttgtgaaa accgtggctg tgaaaatact gaaaaacgag gccaatgacc ccgctcttaa
1321 agatgagtta ttagcagaag caaatgtcat gcagcagctg gacaacccgt acatcgtgcg
1381 gatgatcggg atatgcgagg ccgagtcctg gatgctggtt atggagatgg cagaacttgg
1441 tccctcaat aagtatttgc agcagaacag acatgtcaag gataagaaca tcatagaact
1501 ggttcatcag gtttccatgg gcatgaagta cttggaggag agcaattttg tgcacagaga
1561 tctggctgca agaaatgtgt tgctagttac ccaacattac gccaagatca gtgatttcgg
1621 actttccaaa gcactgcgtg ctgatgaaaa ctactacaag gcccagaccc atggaaagtg
1681 gcctgtcaag tggtacgctc cggaatgcat caactactac aagttctcca gcaaaagcga
1741 tgtctggagc tttggagtgt tgatgtggga agcattctcc tatgggcaga gccatatcg
1801 agggatgaaa ggaagtgaag tcaccgctat gttagagaaa ggagagcgga tgggggtgccc
1861 tgcagggtgt ccaagagaga tgtacgatct catgaatctg tgctggacat acgatgtgga
1921 aaacaggccc ggattcgcag cagtggaact gcggctgcgc aattactact atgacgtggt
1981 gaactaaccg ctcccgcacc tgtcggtggc tgcctttgat cacaggagca atcacaggaa
2041 aatgtatcca gaggaattga ttgtcagcca cctccctctg ccagtcggga gagccaggct
2101 tggatggaac atgcccacaa cttgtcaccc aaagcctgtc ccaggactca ccctccacaa
2161 agcaaaggca gtcccgggag aaaagacgga tggcaggatc caaggggcta gctggatttg
2221 tttgttttct tgtctgtgtg attttcatac aggttatttt tacgatctgt ttccaaatcc
2281 ctttcatgtc tttccacttc tctgggtccc ggggtgcatt tgttactcat cgggcccagg
2341 gacattgcag agtggcctag agcactctca ccccaagcgg ccttttccaa atgcccaagg
2401 atgccttagc atgtgactcc tgaagggaag gcaaaggcag aggaatttgg ctgcttctac
2461 ggccatgaga ctgatccctg gccactgaaa agctttcctg acaataaaaa tgttttgagg
2521 ctttaaaaag aaaaaaaaaa a
```

Human Syk Kinase Nucleotide Sequence (1-2541)

Figure 9A

```
  1 massgmadsa nhlpfffgni treeaedylv qggmsdglyl lrqsrnylgg falsvahgrk
 61 ahhytierel ngtyaiaggr thaspadlch yhsqesdglv cllkkpfnrp qgvqpktgpf
121 edlkenlire yvkqtwnlqg qaleqaiisq kpqlekliat tahekmpwfh gkisreeseq
181 ivligsktng kflirardnn gsyalcllhe gkvlhyridk dktgklsipe gkkfdtlwql
241 vehysykadg llrvltvpcq kigtqgnvnf ggrpqlpgsh passpaqgnr qestvsfnpy
301 epelapwaad kgpqrealpm dtevyespya dpeeirpkev yldrklltle dkelgsgnfg
361 tvkkgyyqmk kvvktvavki lkneandpal kdellaeanv mqqldnpyiv rmigiceaes
421 wmlvmemael gplnkylqqn rhvkdkniie lvhqvsmgmk yleesnfvhr dlaarnvllv
481 tqhyakisdf glskalrade nyykaqthgk wpvkwyapec inyykfssks dvwsfgvlmw
541 eafsygqkpy rgmkgsevta mlekgermgc pagcpremyd lmnlcwtydv enrpgfaave
601 lrlmyyydv vn
```

Human Syk Kinase Amino Acid Sequence (1-612)

Figure 9B

```
  1 gccagtgaat tcgggggctc agccctcctc cctcccttcc ccctgcttca ggctgctgag
 61 cactgagcag cgctcagaat ggaagccatc gccaaatatg acttcaaagc tactgcagac
121 gacgagctga gcttcaaaag gggggacatc ctcaaggttt tgaacgaaga atgtgatcag
181 aactggtaca aggcagagct taatggaaaa gacggcttca ttcccaagaa ctacatagaa
241 atgaaaccac atccgtggtt ttttggcaaa atccccagag ccaaggcaga agaaatgctt
301 agcaaacagc ggcacgatgg ggcctttctt atccgagaga gtgagagcgc tcctggggac
361 ttctccctct ctgtcaagtt tggaaacgat gtgcagcact tcaaggtgct ccgagatgga
421 gccgggaagt acttcctctg ggtggtgaag ttcaattctt tgaatgagct ggtggattat
481 cacagatcta catctgtctc cagaaaccag cagatattcc tgcgggacat agaacaggtg
541 ccacagcagc cgacatacgt ccaggccctc tttgactttg atccccagga ggatgggagag
601 ctgggcttcc gccggggaga ttttatccat gtcatggata actcagaccc caactggtgg
661 aaaggagctt gccacgggca gaccggcatg tttcccccgca attatgtcac ccccgtgaac
721 cggaacgtct aagagtcaag aagcaattat taaagaaag tgaaaaatgt aaaacacata
781 caaaagaatt aaacccacaa gctgcctctg acagcagcct gtgagggagt gcagaacacc
841 tggccgggtc accctgtgac cctctcactt tggttggaac tttaggggggt ggggggggggc
901 gttggattta aaaatgccaa aacttaccta taaattaaga agagttttta ttacaaattt
961 tcactgctgc tcctctttcc cctcctttgt ctttttttc atccttttt ctcttctgtc
1021 catcagtgca tgacgtttaa ggccacgtat agtcctagct gacgccaata ataaaaaaca
1081 agaaaccaaa aaaaaaaaac ccgaattca
```

Human Grb Nucleotide Sequence (1-1109)

Figure 10A

```
  1 meaiakydfk ataddelsfk rgdilkvlne ecdqnwykae lngkdgfipk nyiemkphpw
 61 ffgkipraka eemlskqrhd gaflireses apgdfslsvk fgndvqhfkv lrdgagkyfl
121 wvvkfnslne lvdyhrstsv srnqqiflrd ieqvpqqpty vqalfdfdpq edgelgfrrg
181 dfihvmdnsd pnwwkgachg qtgmfprnyv tpvnrnv
```

Human Grb Amino Acid Sequence (1-217)

Figure 10B

```
   1 ctaggctttt gcaaaaagct tcacgctgcc gcaagcactc agggcgcaag ggctgctaaa
  61 ggaagcggaa cacgtagaaa gccagtccgc agaaacggtg ctgaccccgg atgaatgtca
 121 gctactgggc tatctggaca agggaaaacg caagcgcaaa gagaaagcag ttcctgtgcc
 181 ttaagaacat tagaaccttc ctgtccacct gctgtgagaa gttcggcctc aagcggagcg
 241 agctcttcga agcctttgac ctcttcgatg tgcaggattt tggcaaggtc atctacaccc
 301 tgtctgctct gtcctggacc ccgatcgccc agaacagggg gatcatgccc ttccccaccg
 361 aggaggagag tgtaggtgat gaagacatct acagtggcct gtccgaccag atgacgaca
 421 cggtggagga ggatgaggac ctgtatgact gcgtggagaa tgaggaggcg gaaggcgacg
 481 agatctatga ggacctcatg cgctcggagc ccgtgtccat gccgcccaag atgacagagt
 541 atgacaagcg ctgctgctgc ctgcgggaga tccagcagac ggaggagaag tacactgaca
 601 cgctgggctc catccagcag catttcttga gcccctgca acggttcctg aaacctcaag
 661 acattgagat catctttatc aacattgagg acctgcttcg tgttcatact cacttcctaa
 721 aggagatgaa ggaagccctg gcaccccctg gcgcaccgaa tctctaccag gtcttcatca
 781 aatacaagga gaggttcctc gtctatggcc gctactgcag ccaggtggag tcagccagca
 841 aacacctgga ccgtgtggcc gcagcccggg aggacgtgca gatgaagctg gaggaatgtt
 901 ctcagagagc caacaacggg aggttcactg cgcgacctgc tgatggtgcc tatgcagcga
 961 gttctcaaat atcacctcct tctccaggag ctggtgaaac acacgcagga ggcgatggag
1021 caaggaaact gcggctggcc ctggatgcca tgagggacct ggctcagtgc gtgaacgagg
1081 tcaagcgaga caacgagaca ctgcgacaga tcaccaattt ccagctgtcc attgagaacc
1141 tggaccagtc tctggctcac tatggccggc caagatcga cggggaactc aagatcacct
1201 cggtggaacg gcgctccaag atggacaggt atgccttcct gctcgacaaa gtctactca
1261 tctgtaagcg caggggagac tcctatgacc tcaaggactt tgtaaacctg cacagcttcc
1321 aggttcggga tgactcttca ggagaccgag acaacaagaa gtggagccac atgttcctcc
1381 tgatcgagga ccaaggtgcc cagggctatg agctgttctt caagacaaga gaattgaaga
1441 agaagtggat ggagcagttt gagatggcca tctccaacat ctatccggag aatgccaccg
1501 ccaacgggca tgacttccag atgttctcct ttgaggagac cacatcctgc aaggcctgtc
1561 agatgctgct tagaggtacc ttctatcagg gctaccgctg ccatcggtgc cgggcatctg
1621 cacacaagga gtgtctgggg aggggtccctc catgtggccg acatgggcaa gatttcccag
1681 gaactatgaa gaaggacaaa ctacatcgca gggctcagga caaaaagagg aatgagctgg
1741 gtctgcccaa gatggaggtg tttcaggaat actacgggct tcctccaccc cctggagcca
1801 ttggaccctt tctacggctc aaccctggag acattgtgga gctcacgaag gctgaggctg
1861 aacagaactg gtgggaggc agaaatacat ctactaatga aattggctgg ttccttgta
1921 acagggtgaa gccctatgtc catggccctc ctcaggacct gtctgttcat ctctggtacg
1981 caggccccat ggagcgggca ggggcagaga gcatcctggc caaccgctcg gacgggactt
2041 tcttggtgcg gcagagggtg aaggatgcag cagatttgc catcagcatt aaatataacg
2101 tcgaggtcaa gcacacggtt aaaatcatga cagcagaagg actgtaccgg atcacagaga
2161 aaaaggcttt ccggggggctt acggagctgg tggagtttta ccagcagaac tctctaaagg
2221 attgcttcaa gtctctggac accaccttgc agttccccct caaggagcct gaaaagagaa
2281 ccatcagcag gccagcagtg ggaagcacaa agtattttgg cacagccaaa gcccgctatg
2341 acttctgcgc ccgtgaccgt tcagagctgt cgctcaagga gggtgacatc atcaagatcc
2401 ttaacaagaa gggacagcaa ggctggtggc gaggggagat ctatggccgg gttggctggt
2461 tccctgccaa ctacgtggag gaagattatt ctgaatactg ctgagccctg gtgccttggc
2521 agagagacga gaaactccag gctctgagcc cggcgtggcc aggcagcgga ccaggggctg
2581 tgacagctcc ggcgggtgga gactttggga tggactggag gaggccagcg tccagctggc
2641 ggtgctcccg ggatgtgccc tgacatggtt aatttataac accccgattt tcctcttggg
2701 tccctcaag cagacggggg ctcaagggg ttacatttaa taaaaggatg aagatgg
```

Human Vav Nucleotide Sequence (1-2757)

Figure 11A

```
  1 mnvsywaiwt renasakrkq flclknirtf lstccekfgl krselfeafd lfdvqdfgkv
 61 iytlsalswt piaqnrgimp fptccesvgd ediysglsdq iddtveeded lydcveneea
121 egdeiyedlm rsepvsmppk mteydkrccc lreiqqteek ytdtlgsiqq hflkplqrfl
181 kpqdieiifi niedllrvht hflkemkeal gtpgapnlyq vfikykerfl vygrycsqve
241 saskhldrva aaredvqmkl eecsqrannng rftarpadga yaassqispp spgagethag
301 gdgarklrla ldamrdlaqc vnevkrdnet lrqitnfqls ienldqslah ygrpkidgel
361 kitsverrsk mdryaflldk allickrrgd sydlkdfvnl hsfqvrddss gdrdnkkwsh
421 mflliedqga qgyelffktr elkkkwmeqf emaisniype natanghdfq mfsfeettsc
481 kacqmllrgt fyqgyrchrc rasahkeclg rvppcgrhgq dfpgtmkkdk lhrraqdkkr
541 nelglpkmev fqeyyglppp pgaigpflrl npgdiveltk aeaeqnwwveg mtstneigw
601 fpcnrvkpyv hgppqdlsvh lwyagpmera gaesilanrs dgtflvrqrv kdaaefaisi
661 kynvevkhtv kimtaeglyr itekkafrgl telvefyqqn slkdcfksld ttlqfpfkep
721 ekrtisrpav gstkyfgtak arydfcardr selslkegdi ikilnkkgqq gwwrgeiygr
781 vgwfpanyve edyseyc
```

Human Vav Amino Acid Sequence (1-797)

Figure 11B

```
   1 gaattccggg cccggatagc cggcggcggc ggcggcggcg gcggcggcgg cggccgggag
  61 aggcccctcc ttcacgccct gcttctctcc ctcgctcgca gtcgagccga gccggcggac
 121 ccgcctgggc tccgaccctg cccaggccat ggccggcaac gtgaagaaga gctctggggc
 181 cggggcggc acgggctccg ggggctcggg ttcgggtggc ctgattgggc tcatgaagga
 241 cgccttccag ccgcaccacc accaccacca ccacctcagc cccacccgc cggggacggt
 301 ggacaagaag atggtggaga agtgctggaa gctcatggac aaggtggtgc ggttgtgtca
 361 gaacccaaag ctggcgctaa agaatagccc accttatatc ttagacctgc taccagatac
 421 ctaccagcat ctccgtacta tcttgtcaag atatgagggg aagatggaga cacttggaga
 481 aaatgagtat tttagggtgt ttatggagaa tttgatgaag aaaactaagc aaaccataag
 541 cctcttcaag gagggaaaag aaagaatgta tgaggagaat tctcagccta ggcgaaacct
 601 aaccaaactg tccctcatct tcagccacat gctggcagaa ctaaaaggaa tctttccaag
 661 tggactcttt cagggagaca catttcggat tactaaagca gatgctgcgg aattttggag
 721 aaaagctttt ggggaaaaga caatagtccc ttggaagagc tttcgacagg ctctacatga
 781 agtgcatccc atcagttctg ggctggaggc catggctctg aaatccacta ttgatctgac
 841 ctgcaatgat tatatttcgg tttttgaatt tgacatcttt acccgactct ttcagccctg
 901 gtcctctttg ctcaggaatt ggaacagcct tgctgtaact catcctggct acatggcttt
 961 tttgacgtat gacgaagtga aagctcggct ccagaaattc attcacaaac ctggcagtta
1021 tatcttccgg ctgagctgta ctcgtctggg tcagtgggct attgggtatg ttactgctga
1081 tgggaacatt ctccagacaa tccctcacaa taaacctctc ttccaagcac tgattgatgg
1141 cttcagggaa ggcttctatt tgtttcctga tggacgaaat cagaatcctg atctgactgg
1201 cttatgtgaa ccaactcccc aagaccatat caaagtgacc caggaacaat atgaattata
1261 ctgtgagatg ggctccacat tccaactatg taaaatatgt gctgaaaatg ataaggatgt
1321 aaagattgag ccctgtggac acctcatgtg cacatcctgt cttacatcct ggcaggaatc
1381 agaaggtcag ggctgtcctt ctgccgatg tgaaattaaa ggtactgaac ccatcgtggt
1441 agatccgttt gatcctagag ggagtggcag cctgttgagg caaggagcag agggagctcc
1501 ctccccaaat tatgatgatg atgatgatga acgagctgat gatactctct tcatgatgaa
1561 ggaattggct ggtgccaagg tggaacggcc gccttctcca ttctccatgg ccccacaagc
1621 ttccctccc ccggtgccac cacgacttga ccttctgccg cagcgagtat gtgttccctc
1681 aagtgcttct gctcttggaa ctgcttctaa ggctgcttct ggctcccttc ataaagacaa
1741 accattgcca gtacctccca cacttcgaga tcttccacca ccaccgcctc cagaccggcc
1801 atattctgtt ggagcagaat cccgacctca agacgcccc ttgccttgta caccaggcga
1861 ctgtccctcc agagacaaac tgcccctgt cccctctagc cgccttggag actcatggct
1921 gccccggcca atccccaaag taccagtatc tgccccaagt tccagtgatc cctggacagg
1981 aagagaatta accaaccggc actcacttcc attttcattg ccctcacaaa tggagcccag
2041 accagatgtg cctaggctcg gaagcacgtt cagtctggat acctccatga gtatgaatag
2101 cagcccatta gtaggtccag agtgtgacca ccccaaaatc aaaccttcct catctgccaa
2161 tgccatttat tctctggctg ccagacctct tcctgtgcca aaactgccac ctggggagca
2221 atgtgagggt gaagaggaca cagagtacat gactccctct tccaggcctc tacggccttt
2281 ggatacatcc cagagttcac gagcatgtga ttgcgaccag cagattgata gctgtacgta
2341 tgaagcaatg tataatattc agtcccaggc gccatctatc accgagagca gcacctttgg
2401 tgaagggaat ttggccgcag cccatgccaa cactggtccc gagggagtcag aaaatgagga
2461 tgatgggtat gatgtcccaa agccacctgt gccggccgtg ctggcccgcc gaactctctc
2521 agatatctct aatgccagct cctccttggg ctggttgtct ctggatggtg atcctacaac
2581 aaatgtcact gaaggttccc aagttcccga gaggcctcca aaaccattcc cgcggagaat
2641 caactctgaa cggaaagctg gcagctgtca gcaaggtagt ggtcctgccg cctctgctgc
2701 caccgcctca cctcagctct ccagtgagat cgagaacctc atgagtcagg ggtactccta
2761 ccaggacatc cagaaagctt tggtcattgc ccagaacaac atcgagatgg ccaaaaacat
2821 cctccgggaa tttgtttcca tttcttctcc tgcccatgta gctacctagc acaccatctc
2881 cctgctgcag gtttagagga ccagtgagtt gggagttatt actcaagtgg cacctagaag
2941 ggcaggagtt cctttggtga cttcacagtg aagtcttgcc ctctctgtgg gatatcacat
3001 cagtggttcc aagatttcaa agtggtgaaa tgaaaatgga gcagctagta tgtttatta
3061 ttttatgggt cttgagtgca tttgaaggtg
```

Human Cb1 Nucleotide Sequence (1-3090)

Figure 12A

```
  1 magnvkkssg aggggsggsg aggliglmkd afqphhhhhh lsphppctvd kkmvekcwkl
 61 mdkvvrlcqn pnvalknspp yildllpdty qhlrtvlsry egkmetlgen eyfrvfmenl
121 mkktkqtisl fkegkermye ensqprrnlt klslifshml aelkgifpsg lfqgdtfrit
181 kadaaefwrk afgektivpw ksfrqalhev hpissgleam alkstidltc ndyisvfefd
241 iftrlfqpws sllrnwnsla vthpgymafl tydevkarlq kfihkpgsyi frlsctrlgq
301 waigyvtadg nilqtiphnk plfqalidgf regfylfpdg mqnpdltgl ceptpqdhik
361 vtqicaendk dvkiepcghl mctscltswq esegqgcpfc rceikgtepi vvdpfdprgs
421 gsllrqgaeg apspnydddd deraddslfm mkelagakve rpsspfsmap qaslppvppr
481 ldllqqrapv pastsvlgta skaasgslhk dkplpipptl rdlppppppd rpysvgaetr
541 pqrrplpctp gdcpsrdklp pvpssrpgds wlsrtipkvp vatpnpgdpw ngreltnrhs
601 lpfslpsqme pradvprlgs tfsldtsmtm nsspvagpes ehpkikpsss anaiyslaar
661 plpmpklppg eqgeseedte ymtptsrpvg vqkpepkrpl eatqssracd cdqqidscty
721 eamytiqsqa lsvaensasg egnlatahts tgpeesened dgydvpkppv pavlarrtls
781 disnasssfg wlsldgdptn fnegsqvper ppkpfprrin serkassyqq gggatanpva
841 tapspqlsse ierlmsqgys yqdiqkalvi ahnniemakn ilrefvsiss pahvat
```

Human Cbl Amino Acid Sequence (1-896)

Figure 12B

Schematic A

US 8,114,975 B2

PROTEIN TYROSINE KINASE SUBSTRATE LAT AND ITS USE IN THE IDENTIFICATION OF (ANT) AGONISTS OF THE KINASE

PRIORITY

This application is a division of U.S. application Ser. No. 09/597,920, filed Jun. 19, 2000, now issued as U.S. Pat. No. 7,118,889, which is a continuation of International Application No. PCT/US98/27400 filed Dec. 23, 1998, which claims priority to U.S. Provisional application No. 60/060,690, filed Dec. 23, 1997.

This invention was made with government support from a grant from the National Institute of Child Health and Human Development (NICHHD). The United States Government has certain rights in the invention.

FIELD OF THE INVENTION

The invention generally relates to compositions and methods for identifying and testing tyrosine kinase signaling pathway agonists and antagonists, and more particularly, methods and compositions for screening compounds and identifying compounds that will modulate the interaction of protein tyrosine kinase substrates with their intracellular ligands, as well as between their intracellular ligands and other members of the signaling pathway.

BACKGROUND OF INVENTION

The immune system has evolved to provide an organism with a flexible and dynamic mechanism to respond specifically to a wide variety of antigenic insults. In order for an immune response to occur following antigenic challenge, the antigen must not only be recognized by antigen specific lymphocytes, but this recognition event must lead to a variety of cellular responses. T lymphocytes, together with B lymphocytes, represent the two antigen specific components of the cellular immune system. T cells are central to the immune response and control the response to infectious agents, tumors and transplants.

The T cell receptor for antigen (TCR) recognizes and binds foreign antigens. This binding event leads to T cell activation. The activation of T lymphocytes is a complex process which results in cell growth and differentiation. The engagement of the TCR on mature peripheral T cells initiates multiple intracellular signals that can lead to cellular proliferation and the acquisition of complex effector functions.

The biochemical mechanisms that couple receptor binding to these intracellular events have been intensively investigated. Early events such as activation of tyrosine phosphorylation, elevation of intracellular calcium, activation of lipid-dependent kinases, and activation of Ras and its downstream kinase cascade are well known [Weiss, A. and Littman, D. R., Signal transduction by lymphocyte antigen receptors, $Cell$ 76:263-274 (1994); Cantrell, D., T Cell Antigen Receptor Signal Transduction Pathways, $Annu. Rev. Immunol.$, 14:259-274 (1996)]. Moreover, there has been analysis of the events involved in transcriptional induction of T cell-specific lymphokines. There remain, however, significant gaps in the understanding of TCR signaling, particularly in how the early tyrosine phosphorylation events couple receptor activation to later cellular events.

Perhaps the most critical insight of the past decade in the study of signal transduction has been the recognition that activation of receptor tyrosine kinases results in the assembly of multimolecular complexes at the cytoplasmic domain of the receptor. Likewise, a major role of the tyrosine phosphorylation cascade initiated by TCR engagement is the assembly of multimolecular signaling complexes at and near the TCR itself. The identity and functions of these proteins that engage in such molecular interactions, are critical in the understanding of T cell receptor signal transduction.

SUMMARY OF THE INVENTION

The invention generally relates to compositions and methods for identifying and testing tyrosine kinase signaling pathway agonists and antagonists, and more particularly, methods and compositions for screening compounds and identifying compounds that will modulate the interaction of protein tyrosine kinase substrates with their intracellular ligands, as well as between their intracellular ligands and other members of the signaling pathway. It is not intended that the present invention be limited to particular signaling pathways. The present invention contemplates that the methods and compositions described herein will be useful for identifying protein tyrosine kinase (PTK) downstream signaling proteins, particularly in cells including but not limited to T cells, NK cells, and mast cells, and will enable the identification of compounds that will modulate the interactions of protein tyrosine kinase that bind particular intracellular ligands, as well as between their intracellular ligands and other members of the signaling pathway.

In preferred embodiments, "Linker for Activation of T-cells" (LAT, and in particular, fragments of LAT) are useful in drug screening assays designed to identify drugs that interfere with the specific binding of Grb2 or GST-GRb2 with LAT and thereby block the activation of downstream signaling molecules.

In one embodiment, the present invention contemplates screening compounds and identifying compounds that modulate the interactions of T cell protein kinases, and their substrates, in particular ZAP-70 and/or Syk tyrosine kinase.

Furthermore, the present invention contemplates identifying ZAP-70 and/or Syk substrates and ZAP-70 and/or Syk-binding ligands, and compounds that will modulate the interaction of ZAP-70 and/or Syk kinase with ZAP-70 and/or Syk substrates and ZAP-70 and/or Syk-binding ligands.

In one embodiment, the present invention contemplates identifying compounds that modulate the interaction of LAT, which binds to activated, Tyr phosphorylated ZAP-70 and/or Syk kinases.

In preferred embodiments, LAT (and, in addition, fragments of LAT and mutated LAT) are useful in drug screening assays designed to identify drugs that interfere with the specific binding activated ZAP-70 and/or Syk kinases with their substrates and thereby block the activation of downstream signaling molecules.

In other embodiments, the present invention contemplates identifying compounds that modulate the interaction of LAT, which may bind to kinases other than ZAP-70 and/or Syk. In other embodiments, the invention provides an isolated LAT polypeptide, or a fragment thereof, having ZAP-70 and/or Syk kinase-specific binding affinity. The invention provides nucleic acids encoding the LAT polypeptide and LAT fragments as part of expression vectors for introduction into cells. The invention provides methods of identifying intracellular molecules which interact with LAT or LAT fragments, as well as exogenous agents (i.e. drugs) which disrupt or enhance the binding of LAT and/or fragments thereof to such intracellular targets.

The claimed polypeptide LAT finds particular use in screening assays for agents or lead compounds for agents useful in the diagnosis, prognosis or treatment of disease, particularly disease associated with undesirable cell growth, differentiation, proliferation and T cell anergy. One such assay involves forming mixtures of 1) LAT (or fragments thereof) and 2) an intracellular LAT-binding ligand, in the presence or absence of 3) a prospective drug candidate. The mixtures are made under conditions that permit the binding of the intracellular LAT-binding ligand to LAT (or fragments thereof) and the mixtures are then analyzed for the presence of such binding. A difference in such binding in the presence of such a drug candidate indicates that the agent is capable of modulating the binding of LAT (or fragments thereof) to an intracellular LAT-binding ligand.

It is not intended that the present invention be limited by the species (human, murine, rat, etc.) of the binding ligands described above. The polypeptide LAT and LAT fragments may bind across species. Moreover, the nucleic acid sequences described herein allow for the identification of homologues in other species by various methods, including but not limited to amplification (e.g. PCR) using primers designed from the nucleic acid sequence of one species (e.g. mouse) on the nucleic acid template of another species (e.g. human).

In one embodiment, the present invention contemplates an isolated nucleic acid encoding at least a fragment of a protein having the amino acid sequence set forth in SEQ ID NO:4. It is not intended that the present invention be limited by the size or nature of the fragment (although it is preferred that such fragments are capable of binding kinases). In one embodiment, said nucleic acid comprises SEQ ID NO:1 and encodes full-length LAT as set forth in (SEQ ID NO:4). In yet another embodiment, said nucleic acid encodes a fusion protein.

It is not intended that the present invention be limited as to the specific nature of the nucleic acid encoding the peptides described above. In one embodiment, said nucleic acid is contained in a vector. In another embodiment, said vector is in a host cell.

The present invention also contemplates complexes of ligands. In one embodiment, the present invention contemplates a composition, comprising a LAT-kinase complex comprising a purified peptide having at least a portion of the amino acid sequence set forth in SEQ ID NO:4 specifically bound to activated ZAP-70 and/or Syk (or other kinases). Again, the peptides bound specifically to activated ZAP-70 and/or Syk kinases may be full-length LAT or a fragment defined by a portion of the amino acid sequence as set forth in SEQ ID NO:4. The peptide may be part of a fusion protein. The complex can also contain other ligands, such as effector molecules downstream to PTKs. The complexes can be used to identify other ligands (as described below).

As noted above, the present invention contemplates compound screening assays. In one embodiment, the present invention contemplates a method for compound screening, comprising: a) providing: i) a peptide comprising at least a portion of the amino acid sequence set forth in SEQ ID NO:4, wherein said portion is capable of binding to ZAP-70 and/or Syk kinases, ii) ZAP-70 and/or Syk kinases, and iii) one or more compounds for screening; b) mixing, in any order, said peptide, said ZAP-70 and/or Syk kinases and said one or more compound; and c) measuring the extent of binding of said peptide to said ZAP-70 and/or Syk kinases. Again, the peptides may be full-length LAT or mutated LAT or a fragment defined by a portion of the amino acid sequence as set forth in SEQ ID NO:4. The peptide may also be part of a fusion protein. The present invention also contemplates embodiments where either the peptide or kinase is bound to other ligands, such as effector molecules downstream to PTKs or other PTKs. These complexes can be used in the compound screening assay described above.

The present invention specifically contemplates an isolated polypeptide comprising at least a portion of the amino acid sequence of SEQ ID NO:4. It is not intended that the present invention be limited to a specific portion. However, in one embodiment, said portion comprises a region comprising at least one tyrosine. In another embodiment, said portion comprises more than one tyrosine (and more preferably more than five tyrosine residues). The present invention also contemplates domains of the LAT protein. While not limited to any particular domain, domains such as the cytosolic domain (defined approximately by amino acids 28 to 233).

The present invention also specifically contemplates antibodies (both polyclonal and monoclonal) to LAT, LAT fragments, mutant LAT, mutant LAT fragments, and LAT/LAT Binding Ligand complexes. In one embodiment, the present invention contemplates A purified antibody which binds specifically to a polypeptide comprising at least a portion of the amino acid sequence of SEQ ID NO:4.

The present invention also contemplates an isolated polynucleotide encoding the polypeptide comprising the sequence of SEQ ID NO:4. In one embodiment, said polynucleotide comprises the sequence of SEQ ID NO: 1. The present invention contemplates embodiments where said polynucleotide is contained on a recombinant expression vector and where said expression vector containing said polynucleotide sequence is contained within a host cell.

In some embodiments, the present invention contemplates nucleic acids capable of hybridizing to portions of the LAT gene. In one embodiment, the present invention contemplates a polynucleotide sequence that hybridizes under stringent conditions to the nucleic acid sequence of SEQ ID NO:1.

As discussed above, screening methods are contemplated. In a preferred embodiment, the present invention contemplates a method of screening a compound, said method comprising: a) providing, in any order: i) a peptide comprising at least a portion of the amino acid sequence set forth in SEQ ID NO:4, wherein said portion is capable of binding to a LAT binding ligand; ii) a LAT binding ligand; and iii) one or more compounds for screening; b) mixing, in any order, said peptide, said LAT binding ligand and said one or more compound; and c) measuring the extent of binding of said peptide to said LAT binding ligand.

It is not intended that the present invention be limited to a particular LAT binding ligand. In one embodiment, said LAT binding ligand comprises a tyrosine kinase. In another embodiment, said kinase comprises ZAP-70 kinase. In yet another embodiment, said kinase comprises Syk kinase.

In the embodiments described above, it may be useful to use the entire LAT polypeptide or fragments. In addition, it may be useful where said peptide is part of a fusion protein.

The present invention also contemplates detecting LAT (e.g. detecting LAT in cells and other biological samples). In one embodiment, the present invention contemplates a method for detecting the presence of a portion of the polypeptide having the amino acid sequence set forth in SEQ ID NO:4, said method comprising the steps of: a) providing in any order: i) an antibody capable of reacting with a portion of the polypeptide having the sequence set forth in SEQ ID NO: 4; and ii) a sample suspected of containing at least a portion of the polypeptide having the sequence set forth in SEQ ID NO: 4; b) combining said antibody and said sample under conditions such that a complex is formed between said antibody and said portion of said polynucleotide; and c) detecting said complex. Again, the antibody can be polyclonal antibody or monoclonal antibody. A variety of cells and samples are contemplated, including but not limited to NK cells, mast cells and lymphocytes.

The present invention also contemplates using antibodies in other formats. In one embodiment, LAT is detected on gels by immunoblotting.

The present invention is not limited to antibody detection. It may be useful to detect nucleic acid encoding the LAT polypeptide or detect gene expression. In one embodiment, the present invention contemplates a method for detecting the presence of polynucleotide sequences encoding at least a portion of LAT gene in a sample, said method comprising the steps of: a) providing in any order: i) a polynucleotide comprising a sequence that hybridizes under stringent conditions to the nucleic acid sequence of SEQ ID NO:1; and ii) a sample suspected of containing nucleic acid comprising the sequence of SEQ ID NO:1; b) combining said polynucleotide and said sample under conditions such that a hybridization complex is formed between said polynucleotide and said sample nucleic acid; and c) detecting said hybridization complex. The present invention contemplates detecting both RNA and DNA. Again, a variety of cells and samples can be used, including but not limited to, NK cells, mast cells and lymphocytes. It is desirable that said detected hybridization complex correlates with expression of the LAT gene in said lymphocytes.

DESCRIPTION OF FIGURES

FIG. 1 shows the purification, cDNA cloning, and the deduced amino acid sequence of LAT (Linker for activation of T cells)

FIG. 2 shows the characterization of the LAT protein.

FIG. 3. shows the tissue distribution of LAT.

FIG. 4 shows LAT is phosphorylated by PTKs and associates with Grb2, Grap, the p85 subunit of PI-3K and PLC-γ1 in 293T cells.

FIG. 4(A) is a representative immunoblot showing tyrosine phosphorylation of LAT by Syk and ZAP-70 PTKs. FLAG-tagged LAT in pcDNA3 was transfected in 293T cells either alone or cotransfected with other PTKs as indicated.

FIG. 5 shows LAT associates with Grb2, p85 and PLC-γ1 in Jurkat T cells.

FIG. 5(B) is a representative immunoblot, depicting lysates from unstimulated or C305 stimulated Jurkat T cells subjected to anti-Grb2 or anti-PLC-γ1 immunoprecipitation, and immunoblotted with anti-LAT antibody.

FIG. 6 shows overexpression of a mutant form of LAT (Y171/191F) blocks complex formation and TCR mediated AP-1 and NFAT transcriptional activation.

FIG. 7A shows the nucleotide sequence (SEQ ID NO:1) of human LAT.

FIG. 7B shows the nucleotide sequence (SEQ ID NO: 2) of an alternative splice variant of human LAT.

FIG. 7C shows the nucleotide sequence (SEQ ID NO: 3) of murine LAT.

FIG. 7D shows the amino acid sequence (SEQ ID NO:4) of human LAT and of murine LAT (SEQ ID NO:5).

FIG. 8A shows the nucleotide sequence (SEQ ID NO:6) of human ZAP-70 kinase.

FIG. 8B shows the amino acid sequence (SEQ ID NO:7) of human ZAP-70 kinase.

FIG. 9A shows the nucleotide sequence (SEQ ID NO:8) of human Syk kinase.

FIG. 9B shows the amino acid sequence (SEQ ID NO:9) of human Syk kinase.

FIG. 10A shows the nucleotide sequence (SEQ ID NO:10) of human Grb2.

FIG. 10B shows the amino acid sequence (SEQ ID NO:11) of human Grb2.

FIG. 11A shows the nucleotide sequence (SEQ ID NO:12) of human Vav.

FIG. 11B shows the amino acid sequence (SEQ ID NO:13) of human Vav.

FIG. 12A shows the nucleotide sequence (SEQ ID NO:14) of human Cbl.

FIG. 12B shows the amino acid sequence (SEQ ID NO:15) of human Cbl.

DEFINITIONS

Figure 1A:
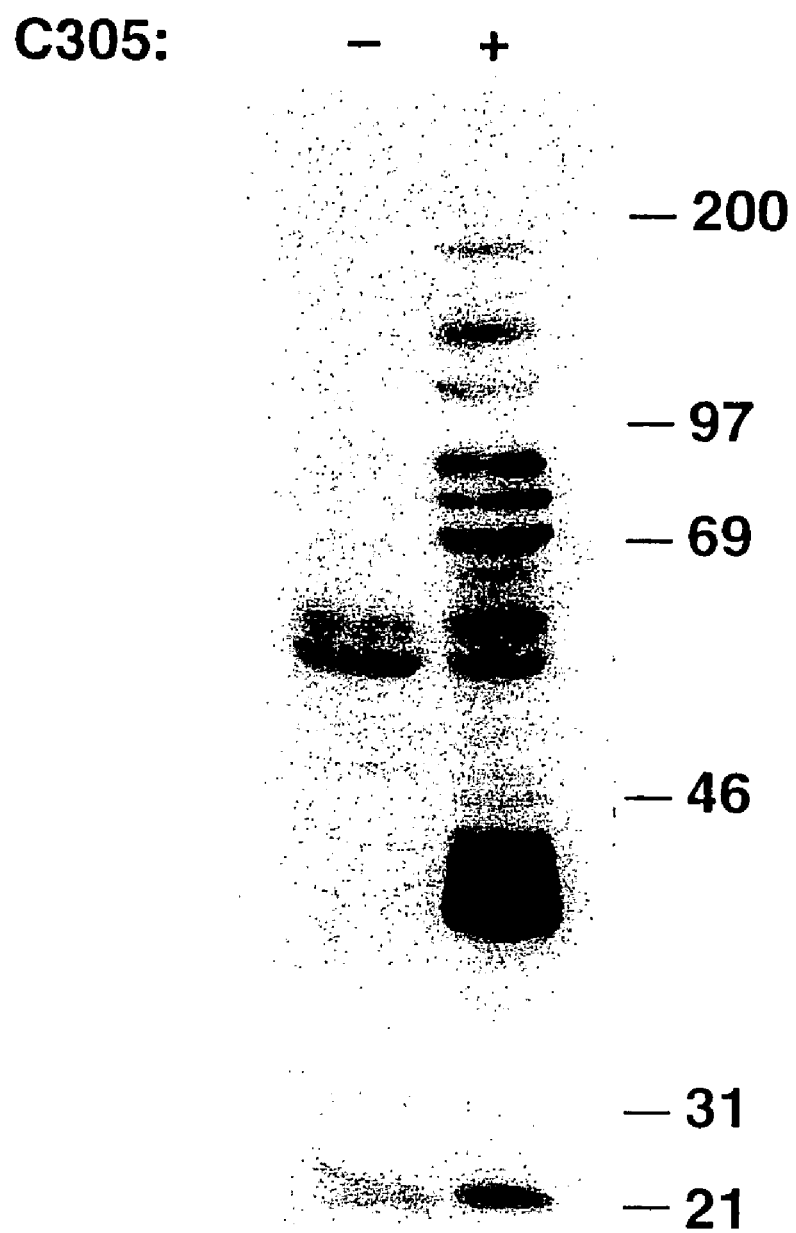
FIG. 1(A) is a representative immunoblot of Jurkat cells stimulated with C305 (+) or unstimulated cells (−), analyzed by immunoblotting with anti-phosphotyrosine antibody (PY20).

To facilitate understanding of the invention, a number of terms are defined below.

The abbreviations used herein are: LAT, Linker for activation of T cells, mLAT, mutant LAT (Y171/191F); PTKs, Protein tyrosine kinases; PTPS, protein tyrosine phosphatases; GST, glutathione S-transferase; TCR, T cell receptor, BCR, B cell antigen receptor; SEAP, secreted alkaline phosphatase; Tyr, tyrosine; PAGE, polyacrylamide gel electrophoresis; SDS, sodium dodecylsulfate; ITAMs, immunoreceptor tyrosine-based activation motifs; SLP-76, SH2-domain Leukocyte Protein; PLC-γ1, Phospholipase C-gamma1; PI3-K, phosphatidylinositol 3-kinase; IgR, Immunoglobulin receptor; SH2(C), C terminal of Src-homology 2 domain.

The terms "Lck and Fyn" refer to the protein tyrosine kinases of the src family, shown to be involved in TCR signaling.

The terms "Zap-70 and Syk" refer to the protein tyrosine kinases of the syk family, shown to be involved in TCR signaling.

The term "Vav" refers to the human oncogene derived from a locus ubiquitously expressed in hematopoietic cells.

The term "Cbl" refers to the human proto-oncogene c-cbl.

The term "Gbr2" refers to the human epidermal growth factor receptor-binding protein.

The term "adaptor" or "linker protein" refers to a protein or scaffold upon which other signaling molecules assemble, for e.g. the Shc protein, Grb2, ZAP-70 etc The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications (e.g. deletions, substitutions, etc.) in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transfection" as used herein refers to the introduction of a transgene into a cell. The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is not endogenous to the cell into which it is introduced. Heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. Generally, although not necessarily, heterologous DNA encodes RNA and proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc. Yet another example of a heterologous DNA includes a nucleotide sequence which encodes a ribozyme which is found in the cell into which it is introduced, and which is ligated to a promoter sequence to which it is not naturally ligated in that cell.

Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "stable transfection" or "stably transfected" refers to the introduction and integration of a transgene into the genome of the transfected cell. The term "stable transfectant" refers to a cell which has stably integrated one or more transgenes into the genomic DNA.

The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

A "transgenic organism" as used herein refers to an organism in which one or more cells has been transiently transfected or stably transfected with a transgene by experimental manipulation. Trangenic organisms may be produced by several methods including the introduction of a "transgene" comprising nucleic acid (usually DNA) into an embryonic target cell or a somatic target cell of a non-human organism by way of human intervention.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et al., *Biochimie* 67:755 (1985). In the case of radioactive oligonucleotide probes, only extremely high specific activities are found to show satisfactory results. See Studencki and Wallace, *DNA* 3:1 (1984) and Studencki et al., *Human Genetics* 37:42 (1985).

K. B. Mullis et al., U.S. Pat. Nos. 4,683,195 and 4,683,202, hereby incorporated by reference, describe a method for increasing the concentration of a segment of a target sequence in a mixture of genomic DNA without cloning or purification. This process for amplifying the target sequence (which can be used in conjunction with the present invention to make target molecules) consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. There can be numerous "cycles" to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified".

The present invention specifically contemplates using primers having a portion of the nucleic acid sequence set forth in SEQ ID NO:1 in a PCR reaction to identify homologues of LAT, as well as the LAT gene in other species. Such primers are preferably less than fifty nucleotides in length (although longer primers can be used if desired).

The present invention also contemplates using probes having a portion of the nucleic acid sequence set forth in SEQ ID NO:1. The term "probe" as used herein refers to a labeled oligonucleotide which forms a duplex structure with a sequence in another nucleic acid, due to complementarity of at least one sequence in the probe with a sequence in the other nucleic acid.

In one embodiment, the present invention contemplates a polynucleotide sequence that hybridizes under stringent conditions to the nucleic acid sequence of SEQ ID NO:1. As used herein the term "stringency" is used in reference to the conditions of temperature, ionic strength, and the presence of other compounds such as organic solvents, under which nucleic acid hybridizations are conducted. "Stringency" typically occurs in a range from about $T_m$-5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Conditions of "weak" or "low" stringency are often required with nucleic acids that are derived from organisms that are genetically diverse, as the frequency of complementary sequences is usually low between such organisms.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g. Green Fluorescent Protein (GFP).

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It should be noted that, while the invention does not require that a comparison be made between one or more forms of a gene to detect sequence variations, such comparisons are possible using particular hybridization conditions as described in U.S. Pat. No. 5,652,096, hereby incorporated by reference.

The term "$K_m$" as used herein refers to the Michaelis-Menton constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAR" and is complementary to a reference sequence "GTATA".

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length LAT cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci. (U.S.A.)* 85:2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length LAT sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence (e.g., various fragments of LAT protein). Fragments typically are at least 4 amino acids long, preferably at least 20 amino acids long, usually at least 50 amino acids long or longer, and span the portion of the polypeptide required for intermolecular binding of LAT.

The term "analog" as used herein refers to polypeptides which are comprised of a segment of at least 25 amino acids that has substantial identity to a portion of the deduced amino acid sequence of LAT. The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as antagonists or agonists of LAT by inclusion in screening assays described herein below.

GENERAL DESCRIPTION OF THE INVENTION

The invention generally relates to compositions and methods for identifying and testing tyrosine kinase signaling pathway agonists and antagonists, and more particularly, methods and compositions for screening compounds and identifying compounds that will modulate the interaction of protein tyrosine kinase substrates with their intracellular ligands, as well as between their intracellular ligands and other members of the signaling pathway.

Identifying and developing new pharmaceuticals is a multibillion dollar industry in the U.S. alone. Agonists and antagonists of critical proteins in signal transduction pathways provide a promising class of targets for novel therapeutics directed to human diseases. Urgently needed are efficient methods of identifying pharmacological agents or drugs which are active at critical target points of signal transduction pathways. Methods amenable to automated, cost-effective, high throughput drug screening have immediate application in a broad range of domestic and international pharmaceutical and biotechnology drug development programs.

The present invention contemplates elements of the T cell signal transduction pathway as targets for pharmaceutical intervention in the immune system. Immunosuppression is therapeutically desirable in a wide variety of circumstances including transplantation, allergy and other forms of hypersensitivity, autoimmune diseases, infectious diseases and cancer. Cyclosporin, a widely used drug for effecting immunosuppression, is believed to act by inhibiting a calcineurin, a phosphatase which activates certain transcription factors. However, because of side effects and toxicity, clinical indications of cyclosporin (and the more recently developed FK506) are limited. Accordingly, it is desired to identify agents which specifically target critical points in the pathway, that will be less toxic than current drugs, such as cyclosporin, which target more widely expressed molecules.

In one embodiment, the invention provides compositions and methods for identifying and testing the syk family of protein tyrosine kinase (ZAP-70 and syk) substrates. In another embodiment, the invention contemplates identifying tyrosine kinase signaling pathway agonists and antagonists, and in particular, compositions comprising LAT which is Tyr phosphorylated by ZAP-70 and/or Syk protein tyrosine kinases leading to recruitment of multiple signaling molecules.

In preferred embodiments, the invention contemplates identifying tyrosine kinase signaling pathway agonists and antagonists, and in particular, compositions comprising LAT and fragments thereof, which bind to Grb2

The description of the invention involves: A) T cell antigen receptor signaling, B) TCR-Associated Protein Tyrosine Kinases and their Substrates, C) Multimolecular Complexes in TCR signaling, D) Tyrosine Phosphatases, E) LAT as a ZAP-70 and/or Syk tyrosine kinase substrate, and F) Uses Of The Invention.

A. T Cell Antigen Receptor Signaling

The complexity of molecular associations involved in TCR signaling begins with the TCR, which is composed of 6 different polypeptide chains thought to be organized into an 8-chain structure. These polypeptides include a ligand binding heterodimer ($\alpha\beta$ or $\gamma\delta$) and the non-polymorphic CD3$\epsilon$, $\gamma$, $\delta$ and TCR$\zeta$ chains. These non-polymorphic chains are required for receptor assembly, cell-surface expression and signaling. Critical regions of the cytoplasmic domains of these chains are the immunoreceptor tyrosine-based activation motifs (ITAMs), three of which are in each of the TCR$\zeta$ chains, and one in each of the CD3 chains (Cambier, 1995). Since each TCR can contain a TCR$\zeta$ dimer and two CD3 dimers ($\epsilon\delta$, $\epsilon\gamma$), each TCR can contain a total of ten ITAMs.

It has been well documented that these motifs are necessary and sufficient for coupling the TCR to the intracellular signaling machinery, and function by binding key signaling molecules in resting and activated T cells. Upon TCR activation the tyrosine residues within the ITAMs become phosphorylated, permitting the binding of SH2 domain-containing proteins as a consequence of the ability of SH2 domains to bind specific phosphotyrosine-containing polypeptides. Additional signaling molecules are subsequently recruited to these newly TCR-associated proteins via SH2 or other modular interaction domains.

While a similar requirement of ITAMs for initiating signaling by the B-cell antigen receptor (BCR) and certain immunoglobulin receptors (IgR) has been shown, the TCR is notable for the sheer number of ITAMs present in a single receptor. Two different explanations for the presence of ten ITAMs within a single receptor have been proposed. The multiple ITAMs may provide the capacity to amplify the signal received by each TCR. Indeed, it has been shown that the intensity of the response to signaling by recombinant ITAM-containing polypeptide chains is dependent on the number of ITAMs present. As the T cell may be required to respond strongly in the presence of a low antigen concentration, this multiplicity of ITAMs is potentially quite important. However, recent studies offer an alternative explanation. A specificity of interaction with different ITAMs has been noted for a number of molecules including ZAP-70, PLC$\gamma$1, PI3-K and Shc, raising the possibility that ITAMs are bound differentially [Exley, M., Varticovsky, L., Peter, M., Sancho, J. and Terhorst, C., Association of phosphatidylinositol-3-kinase with a specific sequence of the T cell receptor chain is dependent on T cell activation, *J. Biol. Chem.* 269:15140-15146 (1994); Cambier, J. C. and Johnson, S. A., Differential binding activity of ARH1/TAM motifs, Immunol. Lett. 44:77-80 (1995); Isakov, N., Wange, R. L., Burgess, W. H., Watts, J. D., Aebersold, R. and Samelson, L. E., ZAP-70 binding specificity to T cell receptor tyrosine-based activation motifs: the tandem SH2 domains of ZAP-70 bind distinct tyrosine-based activation motifs with varying affinity, *J. Exp. Med.* 181:375-380 (1995); Osman, N., Turner, H., Lucas, S., Reif, K. and Cantrell, D. A., The protein interactions of the immunoglobulin receptor family tyrosine-based activation motifs present in the T cell receptor subunits and the CD3, and chains, *Eur. J. Immunol.* 26:1063-1068 (1996)]. Of course, the multiplicity of ITAMs within the TCR may actually serve both purposes.

Another important function of ITAMs may be to mediate an activation-induced association of TCR$\zeta$ and CD3$\epsilon$ with the actin cytoskeleton. There is increasing evidence to suggest that in resting T cells a fraction of the TCR is tightly associated with the actin cytoskeleton, and that upon TCR stimulation the portion of TCR$\zeta$ and CD3$\epsilon$ recoverable in the cytochalasin-disruptable, detergent-insoluble fraction increases [Caplan, S., Zeliger, S., Wang, L. and Baniyash, M., Cell-surface expressed T-cell antigen-receptor chain is associated with the cytoskeleton, *Proc. Natl. Acad. Sci. USA*, 92:4768-4772 (1995); Rozdzial, M. M., Malissen, B. and Finkel, T. H. (1995). Tyrosine-phosphorylated T cell receptor chain associates with actin cytoskeleton upon activation of mature T lymphocytes, *Immunity*, 3:623-633 (1995)]. This association with the actin cytoskeleton requires the intact C-terminal ITAM of TCR$\zeta$. Further investigation is needed to determine how these interactions impinge on TCR recycling, trafficking and signaling, and to assess the role of TCR-cytoskeletal interactions in mediating the changes in cell shape and motility patterns that can accompany T cell activation.

B. TCR-Associated Protein Tyrosine Kinases and Their Substrates

Immediately downstream of the TCR in the signaling pathway are the TCR-associated protein tyrosine kinases (PTKs). Two families of PTKs have been shown to be involved in TCR signaling. Lck and Fyn are members of the Src family, while ZAP-70 and Syk make up another PTK family. Characteristics of these enzymes have been extensively reviewed [Bolen, J. B., Nonreceptor tyrosine protein kinases, *Oncogene*, 8:2025-2031 (1993); Peri, K. G. and Veillette, A., Tyrosine protein kinases in T lymphocytes. *Chem. Immunol.* 59:19-39 (1994)]. A primary function of the Src-family kinases is to phosphorylate key tyrosine residues within the ITAMs. An additional function of these kinases includes the phosphorylation and concurrent activation of the ZAP-70 kinase. Other substrates for these enzymes remain to be defined, though some candidates such as the receptor for $IP_3$ (providing a mechanism for Fyn to directly regulate intracellular $Ca^{2+}$) have been identified [(Jayaraman et al., Regulation of the Inositol 1,4,5-trisphosphate receptor by tyrosine phosphorylation, *Science* 272:1492-1494 (1996)]. It remains to be determined whether Lck and Fyn have any unique substrates, or whether their roles in signaling are redundant. Genetic experiments in which these enzymes are either deleted or over-expressed suggest unique roles for them during development, but these experiments do not address function in a mature T cell that developed in a normal environment.

The relatively recent discovery of the PTKs ZAP-70 and Syk has led to intense investigation of their function in lymphocytes. Syk is central to BCR and IgR function. Though possibly involved in T cell development and the function of certain subsets of γδ T cells, its importance to TCR signaling in mature T cells has not been demonstrated [Cheng et al., Syk tyrosine kinase required for mouse viability and B-cell development, *Nature* 378:303-306 (1995); Fargnoli et al., Syk mutation in Jurkat E6-derived clones results in lack of p72syk expression, *J Biol. Chem.* 270:26533-26537 (1995); Turner et al., Perinatal lethality and blocked B-cell development in mice lacking the tyrosine kinase Syk, *Nature* 378:298-302 (1995)]. In contrast, study of patients with ZAP-70 deficiency and mice with a genetically engineered absence of ZAP-70 confirm the critical function of this enzyme for TCR-mediated signaling [Arpaia et al., Defective T cell receptor signaling and CD8+ thymic selection in humans lacking ZAP-70 kinase, *Cell* 76:947-958 (1994); Chan et al., ZAP-70 deficiency in an autosomal recessive form of severe combined immunodeficiency, *Science* 264:1599-1601 (1994); Elder et al., Human severe combined immunodeficiency due to a defect in ZAP-70, a T cell tyrosine kinase, *Science* 264:1596-1599 (1994); Negishi et al., Essential role for ZAP-70 in both positive and negative selection of thymocytes, *Nature* 376:435-438 (1995)].

Certain factors that regulate the activity of ZAP-70 have been identified. That activation of ZAP-70 requires a Src family kinase could be inferred from the initial description of this enzyme [Chan et al., ZAP-70: a 70 kd protein-tyrosine kinase that associates with the TCR chain, *Cell* 71:649-662 (1992)]. Full enzymatic activity of ZAP-70 expressed in COS cells required co-expression of Lck or Fyn. These results, and the generally recognized ability of tyrosine phosphorylation to regulate PTK activity, lead to an investigation of the sites of tyrosine phosphorylation within activated ZAP-70. Recombinant ZAP-70, when analyzed in vitro, becomes tyrosine phosphorylated at a low level at Y126 and Y292 [Watts et al., Identification by electrospray ionization mass spectrometry of the sites of tyrosine phosphorylation induced in activated Jurkat T cells on the protein tyrosine kinase ZAP-70, *J. Biol. Chem.* 269:29520-29529 (1994)]. However, only when assayed with added recombinant Lck does maximal tyrosine phosphorylation and maximal activity of the enzyme occur. Prominent sites of phosphorylation under these conditions are the adjacent tyrosines 492 and 493 in the kinase domain as well as tyrosines 69, 126, 178 and 292. A similar experiment using kinase-dead ZAP-70 (K369R) and the isolated kinase domain of Lck found only a single prominent site of phosphorylation in ZAP-70 at Y493 [Guanghui et al., Distinct tyrosine phosphorylation sites within ZAP-70 mediate activation and negative regulation of antigen receptor function, *Mol. Cell. Biol.* (1996) In press]. ZAP-70 isolated from intact, activated T cells contains phosphate on Y492 and Y493 as well as on Y292, which lies between the second SH2 domain and the kinase domain (Watts et al., Identification by electrospray ionization mass spectrometry of the sites of tyrosine phosphorylation induced in activated Jurkat T cells on the protein tyrosine kinase ZAP-70, *J. Biol. Chem.* 269:29520-29529 (1994)]. Another critical observation was that isolated proteolytic phosphopeptides purified from activated ZAP-70 contained phosphate on Y493 alone or on both Y492 and Y493, but not on Y492 alone, suggesting that phosphorylation at Y493 precedes and is required for phosphorylation of Y492 (Chan et al., Activation of ZAP-70 kinase activity by phosphorylation of tyrosine 493 is required for lymphocyte antigen receptor function, *EMBO J.* 14:2499-2508 (1995)]. This has also been suggested by COS cell studies with ZAP-70 carrying Tyr to Phe mutations at either Y492 or Y493 [Wange et al., Activating and inhibitory mutations in adjacent tyrosines in the kinase domain of ZAP-70, *J. Biol. Chem.* 270:18730-18733 (1995)].

These observations have led to a model describing the sequential activation of protein tyrosine kinases following TCR engagement [Weiss, A. and Littman, D. R., Signal transduction by lymphocyte antigen receptors, *Cell* 76:263-274 (1994); Cantrell, D., T Cell Antigen Receptor Signal Transduction Pathways, *Annu. Rev. Immunol.* 14: 259-274 (1996)]. Occupancy of the TCR causes the initial activation of Lck and/or Fyn leading to tyrosine phosphorylation of ITAMs. By virtue of its tandem SH2 domains, ZAP-70 then binds to these motifs [Wange et al., Tandem SH2 domains of ZAP-70 bind to T cell antigen receptor and CD3 from activated Jurkat T cells, *J. Biol. Chem.* 268:19797-19801 (1993); Iwashima et al., Sequential interactions of the TCR with two distinct cytoplasmic tyrosine kinases, *Science* 263:1136-1139 (1994)]. Recruitment of ZAP-70 to the ITAMs is required for activation of its kinase activity and for T cell activation, since agents that block recruitment prevent these events [Wange et al., F2(Pmp)2-TAM 3, a novel competitive inhibitor of the binding of ZAP-70 to the T cell antigen receptor, blocks early T cell signaling, *J. Biol. Chem.* 270:944-948 (1995); Qian et al., Dominant-negative Zeta-associated Protein 70 Inhibits T Cell Antigen Receptor Signaling, *J. Exp. Med.* 183:611-620 (1996)]. This sequence of events can be detected in cultured cell lines and in peripheral blood lymphocytes. However, in thymocytes and lymph node T cells, one can detect inactive, non-phosphorylated ZAP-70 bound to the basally tyrosine-phosphorylated TCR in the absence of activation [van Oers et al., Constitutive tyrosine phosphorylation of the T-cell receptor (TCR) subunit: regulation of TCR-associated protein tyrosine kinase activity by TCR, *Mol. Cell. Biol.* 13:5771-5780 (1993); Wiest et al., TCR activation of ZAP-70 is impaired in CD4+CD8+ thymocytes as a consequence of intrathymic interactions that diminish available p56lck, *Immunity* 4:495-504 (1996)]. The phosphorylation of ZAP-70 on Y493 by a Src-family kinase results in the activation of ZAP-70 kinase activity [Chan et al., Activation of ZAP-70 kinase activity by phosphorylation of tyrosine 493 is required for lymphocyte antigen receptor function, *EMBO J.* 14:2499-2508 (1995); Wange et al., Activating and inhibitory mutations in adjacent tyrosines in the kinase domain of ZAP-70, *J. Biol. Chem.* 270:18730-18733 (1995)]. Although this site shares sequence similarity with the so-called autophosphorylation sites defined on other PTKs, for ZAP-70 it is more accurate to refer to this as a transphosphorylation/activation site, since ZAP-70 is unable to phosphorylate this site, and phosphorylation of this site is required for full kinase activity. The mechanism of subsequent tyrosine phosphorylation events within the kinase domain at Y492, outside this region at Y292, and perhaps at other sites is not defined, but is likely to be due to autophosphorylation or transphosphorylation by other activated ZAP-70 molecules on adjacent ITAMs, although an additional role for a heterologous kinase has not been ruled out.

Clearly the role of phosphorylation of Y493 is to activate the kinase activity of ZAP-70; however, the roles played by phosphorylation of tyrosines 492 and 292 are less clear. In contrast to what is seen in Y493F mutants, the mutation of Y492 to Phe results in increased activity in ZAP-70 isolated from transfected COS cells and enhanced BCR signaling in Syk$^{-/-}$ B cells reconstituted with this ZAP-70 mutant [Wange et al., Activating and inhibitory mutations in adjacent tyrosines in the kinase domain of ZAP-70, *J. Biol. Chem.* 270:18730-18733 (1995); Guanghui et al., Distinct tyrosine phosphorylation sites within ZAP-70 mediate activation and negative regulation of antigen receptor function, *Mol. Cell. Biol.*, In press (1996)]. Tyrosine Y492 may therefore serve a negative regulatory function in ZAP-70 when phosphorylated. Alternatively, mutation of Y492 to Phe may cause a loss of hydrogen bonding capacity that maintains the kinase in an inactive conformation when unphosphorylated [Wange et al., Activating and inhibitory mutations in adjacent tyrosines in the kinase domain of ZAP-70, *J. Biol. Chem.* 270:18730-18733 (1995)]. Mutation of Y292 to Phe, unlike the Y492F mutation, has no effect on the activity of purified ZAP-70, but, like the Y492F mutation, results in a hyperactivated state upon BCR stimulation in the Syk$^{-/-}$ chicken B cells [Guanghui et al., Distinct tyrosine phosphorylation sites within ZAP-70 mediate activation and negative regulation of antigen receptor function, *Mol. Cell. Biol.*, In press (1996)]. This is consistent with phosphorylation of Y292 serving a role as a binding site for regulatory molecules, such as SH2 domain-bearing protein tyrosine phosphatases (see below).

Recent reports have identified yet another class of PTKs, the Itk/Btk/Tec family, that may be involved in TCR signaling [reviewed in Desiderio, S. and Siliciano, J. D., The Itk/Btk/Tec Family of Protein-Tyrosine Kinases, *Chem. Immunol.* 59:191-208 (1994)]. This family of PTKs is characterized by having an N-terminal Plextrin Homology (PH) domain, and an SH2 and SH3 domain, in addition to the C-terminal kinase domain. This family of PTKs was first shown to be important in hematopoietic cell function when it was discovered that mutations in the Btk gene at the XLA locus cause X-linked agammaglobulinemia in man. Thus Btk, which is expressed predominantly in B lymphoid and myelomonocytic lineages, is required for normal B cell function. Itk is predominantly expressed in T cells. Itk$^{-/-}$ mice produce fewer thymocytes, and mature T cells isolated from these mice proliferate poorly in response to TCR stimulation, but respond normally to phorbol ester plus ionomycin [Liao, X. C. and Littman, D., Altered T cell receptor signaling and disrupted T cell development in mice lacking Itk. Immunity, 3:757-769 (1995)]. In Jurkat T cells, TCR cross-linking rapidly and transiently tyrosine-phosphorylates Itk, resulting in increased kinase activity in anti-Itk immunoprecipitates (Gibson et al., The EMT/ITK/TSK (EMT) tyrosine kinase is activated during TCR signaling, *J. Immunol.* 156:2716-2722 (1996)]. The precise role of Itk in TCR signaling remains to be determined.

Characterization of pathways downstream of the PTKs depends on identification of their substrates. Detection of protein tyrosine phosphorylation by immunoblotting with specific anti-phosphotyrosine antibodies has revealed a number of kinase targets [Peri, K. G. and Veillette, A., Tyrosine protein kinases in T lymphocytes. Chem. Immunol. 59:19-39 (1994)]. In this fashion PLCγ1 was the first substrate, other than the TCR subunits, to be identified in T cells. Tyrosine phosphorylation of this enzyme is critical to its activation. Vav, a hematopoietic cell-specific proto-oncogene, and more recently, the proto-oncogene Cbl were also identified as being PTK substrates in T cells [Bustelo et al., Product of the Vav protooncogene defines a new class of tyrosine protein kinase substrates, Nature 356: 68-74 (1992); Donovan et al., The protein product of the c-cbl protooncogene is the 120-kDa tyrosine-phosphorylated protein in Jurkat cells activated via the T cell antigen receptor, *J. Biol. Chem.* 269:22921-22924 (1994)]. SH2-domain Leukocyte Protein (SLP-76), a prominent substrate, was recently isolated by virtue of an interaction with the Grb2 linker protein as described below [Jackman et al., Molecular cloning of SLP-76, a 76-kDa tyrosine phosphoprotein associated with Grb2 in T cells, *J. Biol. Chem.* 270:7029-7032 (1995)]. More difficult than identifying the proteins that become tyrosine phosphorylated upon TCR stimulation is determining which PTKs are directly responsible for a given phosphorylation event. As stated above it is clear that ITAM phosphorylation is a function of the Src-family kinases, as is phosphorylation of Y493 of ZAP-70. ZAP-70, at least in vitro, does not phosphorylate these sites.

Substrates of ZAP-70 have been more difficult to identify. Based on previous study of Syk, it has been shown that ZAP-70 can phosphorylate the cytoplasmic domain of erythrocyte band 3 (cdb3) and tubulin in vitro (Wange et al., 1995b; Isakov et al., 1996). Evidence that cdb3 and tubulin are genuine in vivo substrates of Syk has also been presented [Harrison et al., Phosphorylation of human erythrocyte band 3 by endogenous p72syk, *J. Biol. Chem.* 269:955-959 (1994); Peters et al., Syk, activated by cross-linking the B-cell antigen receptor, localizes to the cytosol where it interacts with and phosphorylates alpha-tubulin on tyrosine, *J. Biol. Chem.* 271: 4755-4762 (1996)]. Whether tubulin is an in vivo substrate of ZAP-70 remains to be determined; however, it is interesting that tubulin is tyrosine phosphorylated in activated T cells, and both ZAP-70 and Vav have been found in association with tubulin [Ley et al., Tyrosine phosphorylation of tubulin in human T lymphocytes, *Eur. J. Immunol.*, 24:99-106 (1994); Huby et al., Interactions between the Protein-tyrosine Kinase ZAP-70, the Proto-oncoprotein Vav, and Tubulin in Jurkat T Cells, *J. Biol. Chem.*, 270:30241-30244 (1995)]. These findings further support the contention that cytoskeletal components may play an integral part in the early signal transduction steps. Of the molecules involved in TCR signal transduction that undergo tyrosine phosphorylation upon TCR engagement, only SLP-76 has been shown to be a substrate of ZAP-70 [Wardenburg et al., Phosphorylation of SLP-76 by the ZAP-70 protein tyrosine kinase is required for T cell receptor function, *J. Biol. Chem.*, In press (1996)]. Tyrosine phosphorylation of SLP-76 mediates association with Vav (see below) [Wu et al., Vav and SLP-76 interact and functionally cooperate in IL-2 gene activation, *Immunity* 4:593-602 (1996)]. Of note is that sites likely to be phosphorylated in these three proteins, all share the sequence Asp-Tyr-Glu. Interestingly, the hematopoietic cell specific protein HS1, which has two Asp-Tyr-Glu sites, has been shown to be a substrate for ZAP-70 when HS1, ZAP-70 and Fyn are co-expressed in COS cells (Fusaki et al., Physical and functional interactions of protein tyrosine kinases, p59fyn and ZAP-70, in T cell signaling, *J. Immunol.* 156:1369-1377 (1996)]. The function of HS1 remains unknown.

C. Multimolecular Complexes in TCR Signaling

While it is not intended that the present invention be limited to any particular mechanism of receptor-mediated signal transduction, it is believed that receptor activation leads to assembly of multimolecular complexes on the cytoplasmic domain of platelet-derived and epidermal growth factor receptors. These complexes comprise of multiple signaling molecules that often bind to the receptor by interaction at sites of tyrosine phosphorylation. Many of these signaling molecules are themselves modular, containing variable numbers of interaction domains such as (1) SH2, (2) PTB, (3) SH3 and (4) PH which bind, respectively to (1) pY (in the context of specific residues C-terminal of pY), (2) pY (in the context of specific residues N-terminal of pY), (3) proline-rich regions and (4) phosphotidylinositol (4,5) bisphosphate, inositol phosphates and certain proteins such as G protein βγ subunits. PH domains are thus thought to target some proteins to the plasma membrane. It is believed that, this modular architecture permits the assembly of large multimolecular complexes, as each signaling protein may bind to several different signaling proteins, which may themselves associate with a whole host of additional signaling molecules.

Proteins with the potential to become involved in multimolecular signaling complexes at the TCR include the receptor-proximal kinases themselves. The Src-family kinases contain an SH2, an SH3 and a unique N-terminal domain, all of which can be involved in protein-protein interactions [Bolen, J. B. Nonreceptor tyrosine protein kinases. *Oncogene* 8: 2025-2031(1993); Peri, K. G. and Veillette, A., Tyrosine protein kinases in T lymphocytes, *Chem. Immunol.* 59:19-39 (1994)]. In addition, lipid modification of consensus N-terminal sites stabilizes association of these PTKs with cellular membranes. The unique N-terminal domain of Lck binds to the co-receptor molecules CD4 or CD8, while the comparable region in Fyn binds to non-phosphorylated ITAMs. The SH2 and SH3 domains of Src-family PTKs form an intramolecular association with the tyrosine-phosphorylated C-terminal tail, inhibiting their kinase activity. The phosphorylation status of this negative regulatory tyrosine is controlled by the competing activities of the Csk PTK and the CD45 protein tyrosine phosphatase (PTP). In addition to activating the kinase activity, dephosphorylation of this residue by CD45 also increases the availability of the SH2 and SH3 domains for interaction with other proteins (eg. Cbl, phosphatidylinositol 3-kinase [PI3-K] and ZAP-70) [Donovan et al., The protein product of the c-cbl protooncogene is the 120-kDa tyrosine-phosphorylated protein in Jurkat cells activated via the T cell antigen receptor, *J. Biol. Chem.* 269:22921-22924 (1994); Vogel, L. B. and Fujita, D. J., The SH3 domain of p56lck is involved in binding to phosphatidylinositol 3'-kinase from T lymphocytes, *Mol. Cell. Biol.*, 13:7408-7417 (1993); Thome et al., Syk and ZAP-70 mediate recruitment of p56lck/CD4 to the activated T cell receptor/CD3/complex, *J. Exp. Med.*, 181: 1997-2006 (1995)].

ZAP-70 is also capable of forming multimolecular complexes through its two SH2 domains and via tyrosine-phosphorylated SH2 domain acceptor sites. The only known function of the SH2 domains of ZAP-70 is to target the kinase to the two phosphorylated tyrosines of the ITAM [Wange et al., Tandem SH2 domains of ZAP-70 bind to T cell antigen receptor and CD3 from activated Jurkat T cells, *J. Biol. Chem.* 268:19797-19801 (1993); Iwashima et al., Sequential interactions of the TCR with two distinct cytoplasmic tyrosine kinases, *Science* 263:1136-1139 (1994)]. It is possible however that these SH2 domains have other targets when not engaged to the activated TCR, but this seems unlikely given the unique structure of the tandem SH2 domain of ZAP-70, which only permits high affinity binding to polypeptides possessing two phosphotyrosines within a prescribed distance, as is found in ITAMs [Hatada et al., Molecular basis for interaction of the protein tyrosine kinase ZAP-70 with the T-cell receptor, *Nature* 377:32-38 (1995)]. It is important to note that, unlike Syk, ZAP-70 is not activated by the binding of its tandem SH2 domains to ITAMs [Shiue et al., Syk is activated by phosphotyrosine-containing peptides representing the tyrosine-based activation motifs of the high affinity receptor for IgE, *J. Biol. Chem.* 270:10498-10502 (1995); Neumeister et al., Binding of ZAP-70 to phosphorylated T-cell receptor and enhances its autophosphorylation and generates specific binding sites for SH2 domain-containing proteins, *Mol. Cell. Biol.* 15:3171-3178 (1995); Isakov et al., Purification and characterization of human ZAP-70 protein tyrosine kinase from a baculovirus expression system, *J. Biol. Chem.* 271: 15753-15761 (1996)].

In addition to its role as an enzyme responsible for protein tyrosine phosphorylation, ZAP-70 appears also to function as an adaptor protein or scaffold upon which other signaling molecules assemble [Neumeister et al., Binding of ZAP-70 to phosphorylated T-cell receptor and enhances its autophosphorylation and generates specific binding sites for SH2 domain-containing proteins, *Mol. Cell. Biol.* 15:3171-3178 (1995)]. Interestingly, Lck, Vav and Cbl have all been found in association with ZAP-70 [Thome et al., Syk and ZAP-70 mediate recruitment of p56lck/CD4 to the activated T cell receptor/CD3/complex, *J. Exp. Med.* 181:1997-2006 (1995); Katzav et al., The protein tyrosine kinase ZAP-70 can associate with the SH2 domain of proto-vav, *J. Biol. Chem.* 269: 32579-32585 (1994); Fournel et al., Association of tyrosine protein kinase ZAP-70 with the protooncogene product p120c-cbl in T lymphocytes, *J. Exp. Med.* 183:301-306 (1996)], and, at least for Lck and Vav, this association appears to involve the SH2 domains of these two proteins binding to phosphorylated tyrosines on ZAP-70. As mentioned previously tyrosines 69, 126, 178, 292, 492 and 493 have all been shown to be capable of accepting phosphate in an in vitro kinase reaction with Lck [Watts et al., Identification by electrospray ionization mass spectrometry of the sites of tyrosine phosphorylation induced in activated Jurkat T cells on the protein tyrosine kinase ZAP-70, *J. Biol. Chem.* 269:29520-29529 (1994)]. It has been suggested that two other tyrosines (315 and 319) may be phosphorylatable, and phosphorylated peptides cognate for this region can disrupt the association of Vav with ZAP-70 (Katzav et al., The protein tyrosine kinase ZAP-70 can associate with the SH2 domain of proto-vav, *J. Biol. Chem.* 269: 32579-32585 (994)] While the functional consequences of the ZAP-70 association with these signaling molecules remains to be determined, one can speculate that these associations ensure their efficient phosphorylation by ZAP-70 or associated PTKs, such as Lck. In addition, the association of Lck with tyrosine-phosphorylated ZAP-70 has been suggested to be required for recruitment of Lck-CD4 to the TCR [Thome et al., Syk and ZAP-70 mediate recruitment of p56lck/CD4 to the activated T cell receptor/CD3/complex, *J. Exp. Med.* 181:1997-2006 (1995)], thereby enhancing the assembly of a fully effective signaling complex.

The adaptor protein Grb2 is an example of a modular, so-called, linker protein, consisting entirely of a central SH2 domain flanked by two SH3 domains. In a number of growth factor receptor tyrosine kinase systems, Grb2 has been shown to couple these receptors to the Ras activator protein SOS [Downward, J., The GRB2/Sem-5 adaptor protein, *FEBS Lett.* 338: 113-117 (1994)] As the Ras pathway was known to be required for lymphokine gene activation, a number of investigators sought to determine whether Grb2 was linked to this pathway in T cells. The Grb2-SOS interaction was indeed documented and SOS has been shown to be involved in Ras activation in T cells [Downward, J., The GRB2/Sem-5 adaptor protein, *FEBS Lett.* 338: 113-117 (1994); Holsinger et al., Signal transduction in T lymphocytes using a conditional allele of Sos, *Proc. Natl. Acad. Sci. USA* 92:9810-9814 (1995)]. While, Shc, another linker protein, has been shown to link Grb2 to certain growth factor receptors, its role in TCR signaling remains controversial [Ravichandran et al., Interaction of Shc with Grb2 regulates association of Grb2 with mSOS, *Mol. Cell. Biol.* 15:593-600 (1995); Osman et al., A comparison of the interaction of Shc and the tyrosine kinase ZAP-70 with the T cell antigen receptor chain tyrosine-based activation motif, *J. Biol. Chem.* 270:13981-13986 (1995)].

In addition to the anticipated role of Grb2 in Ras activation, Grb2 was also found to bind several of the most prominent substrates of the TCR-associated PTKs [Motto et al., In vivo association of Grb2 with pp116, a substrate of the T cell antigen receptor-activated protein tyrosine kinase, *J. Biol. Chem.* 269:21608-21613 (1994); Buday et al., A complex of Grb2 adaptor protein, Sos exchange factor, and a 36-kDa membrane-bound tyrosine phosphoprotein is implicated in ras activation in T cells, *J. Biol. Chem.* 269:9019-9023 (1994); Reif et al., SH3 domains of the adapter molecule Grb2 compete with two proteins in T cells: the guanine nucleotide exchange protein SOS and a 75-kDa protein that is a substrate for T cell antigen receptor-activated tyrosine kinases, *J. Biol. Chem.* 269:14081-14087 (1994)]. A 120 kD protein that binds to Grb2 has been shown to be the proto-oncogene Cbl [Donovan et al., The protein product of the c-cbl protooncogene is the 120-kDa tyrosine-phosphorylated protein in Jurkat cells activated via the T cell antigen receptor, *J. Biol. Chem.* 269:22921-22924 (1994); Fukazawa et al., T cell activation-dependent association between the p85 subunit of the phosphatidyl 3-kinase and Grb2/phospholipase C-γ1-binding phosphotyrosyl protein, *J. BIol. Chem.* 270:36-38, 20177-20182 (1995); Meisner et al., Interaction of Cbl with Grb2 and Phosphatidylinositol-3'-Kinase in Activated Jurkat Cells, *Mol. Cell. Biol.* 15:3571-3578 (1995)]. The Grb2-Cbl association is mediated via the N-terminal SH3 domain of Grb2, and is observed in resting and activated T cells. Affinity purification with a Grb2 fusion protein was used to isolate a 76 kD protein, SLP-76, which binds to the C-terminal SH3 domain of Grb2 [Jackman et al., Molecular cloning of SLP-76, a 76-kDa tyrosine phosphoprotein associated with Grb2 in T cells, *J. Biol. Chem.* 270, 7029-7032 (1995). The identity of pp36, a 36 kD substrate, that binds to the SH2 domain of Grb2, has been identified to be "LAT", the composition claimed in the present invention. This protein plays a critical role in TCR signaling, as in addition to binding Grb2, it has also been found in association with PLCγ1 and PI3-K [Cantrell, D., T Cell Antigen Receptor Signal Transduction Pathways, *Annu. Rev. Immunol.* 14: 259-274 (1996) and also see experimental section]. The tight membrane localization of pp36 provides a possible mechanism for recruitment of Grb2, PLCγ1 and PI3-K to the plasma membrane. Grb2-SOS activates the Ras-pathway when localized to the plasma membrane [Downward, J., The GRB2/Sem-5 adaptor protein, *FEBS Lett.* 338: 113-117 (1994); Cantrell, D., T Cell Antigen Receptor Signal Transduction Pathways, *Annu. Rev. Immunol.* 14: 259-274 (1996)], while membrane localization of PLCγ1 and PI3-K permits phosphorylation of these proteins by membrane-associated PTKs, and provides access to lipid substrates.

The binding of SOS and Cbl to Grb2 is mutually exclusive, as proline-rich regions in these proteins compete for the same binding site [Meisner et al., Interaction of Cbl with Grb2 and Phosphatidylinositol-3'-Kinase in Activated Jurkat Cells, *Mol. Cell. Biol.* 15:3571-3578 (1995)]. An interesting area of investigation is whether or not this competition plays a role in TCR signaling. It is also possible that Grb2 could mediate a complex between either pp36 and/or SLP-76 with Cbl or SOS. An additional consequence of formation of the Grb2-Cbl complex could depend on the ability of Cbl, itself, to serve as an adaptor protein. Recent studies demonstrate that Cbl can be found in complex with PI3-K, ZAP-70, 14.3.3τ and CrkL [Meisner et al., Interaction of Cbl with Grb2 and Phosphatidylinositol-3'-Kinase in Activated Jurkat Cells, *Mol. Cell. Biol.* 15:3571-3578 (1995); Fukazawa et al., T cell activation-dependent association between the p85 subunit of the phosphatidyl 3-kinase and Grb2/phospholipase C-γ1-binding phosphotyrosyl protein, *J. BIol. Chem.* 270:36-38, 20177-20182 (1995); Fournel et al., Association of tyrosine protein kinase ZAP-70 with the protooncogene product p120c-cbl in T lymphocytes, *J. Exp. Med.* 183:301-306 (1996); Liu et al. Activation-modulated association of 14-3-3 proteins with Cbl in T cells. J. Biol. Chem. 271, 14591-14595 (1996); Reedquist et al., Stimulation through the T cell receptor induces Cbl association with Crk proteins and guanine nucleotide exchange protein C3G, *J. Biol. Chem.* 271:8435-8442 (1996)]. CrkL is another adapter protein that in turn interacts with C3G, a nucleotide exchange factor for members of the Rac/Rho family of small G proteins.

Study of Vav and SLP-76 has led to the most significant recent insights into TCR signal transduction mechanisms. Vav, first identified as a transforming oncogene when truncated, consists of a number of interaction modules, 2 SH3 domains, one SH2 domain and one PH domain, along with regions sharing homology with Rac/Rho guanine nucleotide exchange proteins [Bustelo et al., Product of the Vav protooncogene defines a new class of tyrosine protein kinase substrates, *Nature* 356:68-74 (1992)]. Over-expression of this protein in Jurkat T cells results in enhanced basal activation of IL-2 promoters and further enhances the response to TCR signaling (Wu et al., Vav and SLP-76 interact and functionally cooperate in IL-2 gene activation, *Immunity* 4:593-602 (1995)]. Its proximal position in the TCR pathway was established by the observation that dominant negative Ras or Raf could block the Vav-mediated enhancement of TCR signaling. The position of Vav in the signaling cascade has been further delineated by the observation that the activity of Vav requires active PTKs and is not functional in a T cell line lacking Lck. Similar studies with SLP-76 over-expression also demonstrated an enhanced response to TCR engagement although without an increase in basal levels of activation (Motto et al., Implications of the GRB2-associated phosphoprotein SLP-76 in T cell receptor-mediated interleukin 2 production, *J. Exp. Med.* 183:1937-1943 (1996)]. Over-expression of both Vav and SLP-76 causes a synergistic induction of basal and TCR-stimulated NFAT and IL-2 promoter activation [Wu et al., Vav and SLP-76 interact and functionally cooperate in IL-2 gene activation, *Immunity* 4:593-602 (1996)].

How these two signaling molecules ultimately affect transcriptional activity is unknown, but it has been shown that a specific interaction between Vav and SLP-76 is required for this activity [Wu et al., Vav and SLP-76 interact and functionally cooperate in IL-2 gene activation, *Immunity* 4:593-602 (1996)]. This association requires the SH2 domain of Vav and tyrosine phosphorylation of SLP-76. This association is required for the subsequent tyrosine phosphorylation of Vav, as crippling the SH2 domain of Vav prevents its tyrosine phosphorylation. Similarly, enhanced signaling does not occur if critical tyrosine residues (112, 128, 145) in SLP-76, presumably the binding sites for the Vav SH2 domain, are mutated to Phe. SLP-76, in turn binds two tyrosine-phosphorylated proteins of 130 (SLAP) and 62 kD. An inactivating mutation within the SLP-76 SH2 domain prevents association of these proteins and significantly blocks the stimulatory effect of SLP-76 over-expression. Clearly Vav and SLP-76 have critical functional effects and the complex of these two proteins with others (eg. pp130 and pp62) is central to TCR function.

D. Tyrosine Phosphatases

The addition of phosphate to tyrosine residues catalyzed by tyrosine kinases induces many binding interactions as described. Regulation of these events by tyrosine phosphatases has equal significance both in initiating and quenching TCR signaling pathways [for review see McFarland et al., Protein tyrosine phosphatases involved in lymphocyte signal transduction, *Chem. Immunol.* 59:40-61 (1994)]. Activation of Src family kinases by CD45 has already been mentioned. Recent evidence for interaction of the SHP-1 PTP with ZAP-70 suggests that regulation of this kinase or its substrates by SHP-1 may also be significant [Plas et al., Direct regulation of ZAP-70 by SHP-1 in T cell antigen receptor signaling, *Science* 272:1173-1176 (1996). This association is mediated by the SH2 domains of SHP-1, which bind to tyrosine phosphorylated ZAP-70 after TCR engagement. Engagement of the SH2 domains of SHP-1 by ZAP-70 stimulates the phosphatase activity with a consequent decrease in net ZAP-70 kinase activity. The functional significance of this interaction can be demonstrated by overexpression of wildtype SHP-1, which decreases IL-2 production in response to TCR stimulation, or conversely by overexpression of catalytically inactive SHP-1 (C453S), which has the opposite effect of enhancing IL-2 production. Other, as yet, unidentified PTPs are likely to have functional significance, and substrates of known PTPs remain to be defined. It is also interesting that SHP-1 has been found to associate with Vav in activated splenocytes and the EL4 T cell lymphoma [Kon-Kozlowski, M. et al., The tyrosine phosphatase PTP1C associates with Vav, Grb2, and mSos1 in hematopoietic cells, *J. Biol. Chem.* 271:3856-3862 (1996)]. This association appears to involve the SH2 and flanking SH3 domains of Vav. As Vav and ZAP-70, and ZAP-70 and SHP-1 have also been shown to associate, determining the actual nature of the associations between these proteins will be required to more fully understand these signaling events. Another PTP that probably plays a role in down-regulating the TCR signal is SHP-2, which has been found to associate with the activation-upregulated T cell surface protein CTLA-4. Fyn, Lck and ZAP-70 are all hyper-phosphorylated in CTLA-4$^{-/-}$ mice [Marengere et al., Regulation of T cell receptor signaling by tyrosine phosphatase SYP association with CTLA-4, *Science* 272:1170-1173 (1996)].

E. LAT as a ZAP-70 and/or Syk Tyrosine Kinase Substrate

Figure 17:
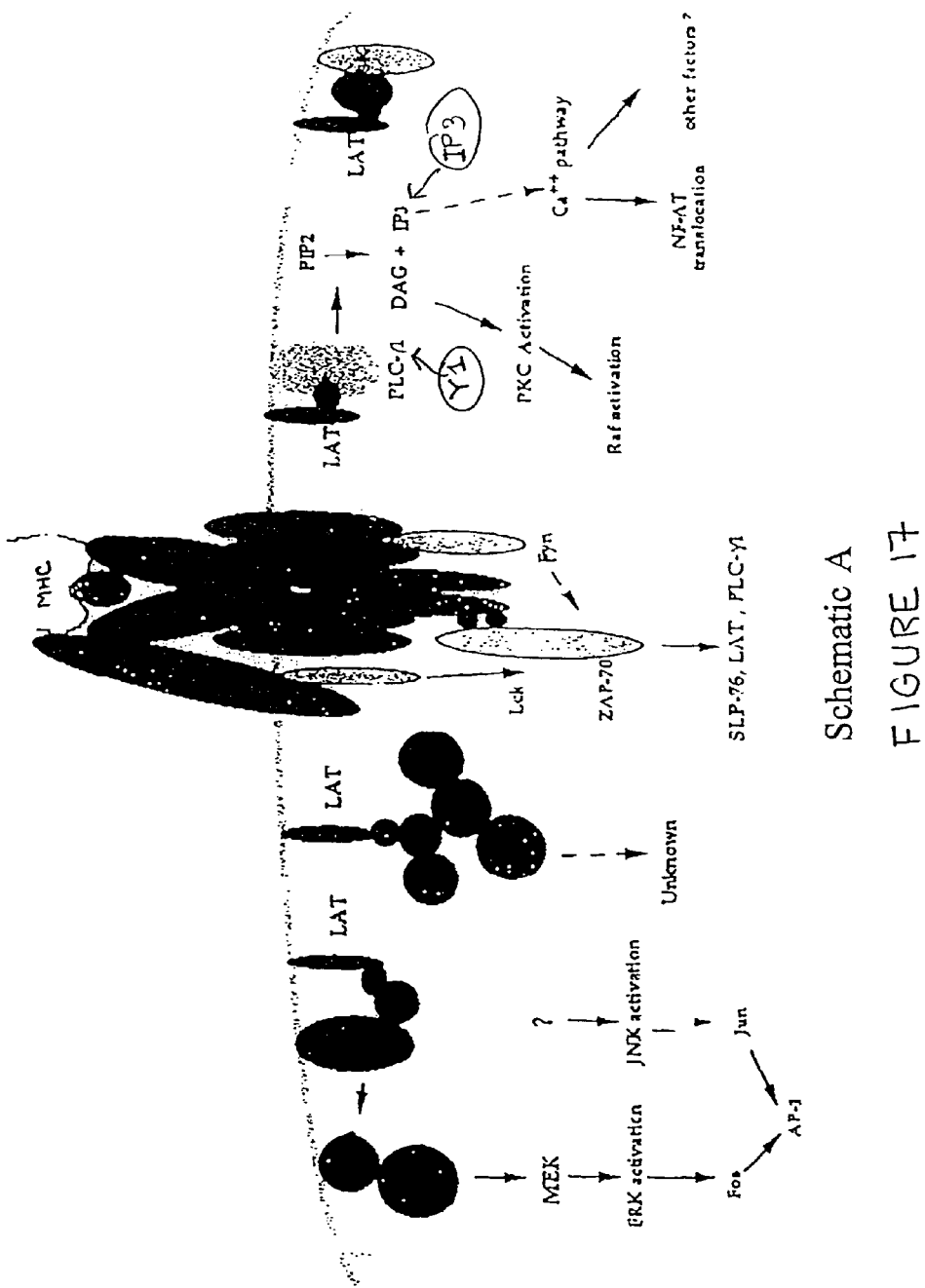
FIG. 17 shows as Schematic A activity of LAT molecule in various cell activations.

In the present invention, LAT, one of the most prominently tyrosine phosphorylaed protein following TCR engagement has been identified. Deduced amino acid sequence identifies a novel integral membrane protein containing multiple potential tyrosine phosphorylation sites. This 36-3 kD protein is capable of binding SH2 domains of Grb2, phospholipase C-γ1 and the p85 subunit of phosphoinositide 3-kinase and may play a central role as a molecule downstream of PTKs capable of binding critical PTK substrates and effector molecules. In the present invention, this protein is shown to be phosphorylated by ZAP-70 and/orSyk protein tyrosine kinases leading to recruitment of multiple signaling molecules. Its function is demonstrated by inhibition of T cell activation following overexpression of a mutant form lacking critical tyrosine residues (For details see experimental section), providing evidence that LAT plays an important role in linking the TCR to cellular activation. Therefore, the molecule has been named: LAT for linker for activation of T cells (See Schematic A, FIG. 17).

F. Uses of the Invention

The invention provides compositions and methods for identifying and testing tyrosine kinase ZAP-70 and/or Syk substrates and ZAP-70 and/or Syk kinase signaling pathway agonists and antagonists, and in particular, compositions comprising LAT (and fragments thereof) which upon activation/tyrosine phosphorylation binds to ZAP-70 and/or Syk kinase and also to Grb2, PLC-γ-1, the p85 subunit of PI-3 kinase, and Cbl, Vav, SLP-76 and/or other critical signaling molecules, either directly or indirectly upon T cell activation.

The polypeptide LAT and fragments thereof, may have one or more LAT-specific binding affinities for particular ligands such as Grb2, PLC-γ-1, the p85 subunit of PI-3 kinase, and other critical signaling molecules, including the ability to specifically bind at least one natural human intracellular LAT-specific binding target or a LAT-specific binding agent such as a LAT-specific antibody or a LAT-specific binding agent identified in assays such as described below. Accordingly, the specificity of a LAT fragment for specific binding agents is confirmed by ensuring non-crossreactivity with other ZAP-70 and/or Syk substrates. Furthermore, preferred LAT fragments are capable of eliciting an antibody capable of distinguishing LAT from other LAT homologues.

1. Antibody Generation

Both polyclonal and monoclonal antibodies are obtainable by immunization with LAT, LAT fragments, mutant LAT, mutant LAT fragments, and LAT/LAT binding ligand complexes and either type is utilizable for immunoassays (as well as therapy). Polyclonal sera are readily prepared by injection of a suitable laboratory animal with an effective amount of the purified peptide, collecting serum from the animal, and isolating specific sera by any of the known immunoadsorbent techniques. Antibodies produced by this method are utilizable in virtually any type of immunoassay (see below).

The use of monoclonal antibodies directed to LAT, LAT fragments, mutant LAT, mutant LAT fragments, and LAT/LAT binding ligand complexes is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed.

by Schwartz, 1981; Kohler and Milstein, *Nature* 256: 495-499, 1975; *European Journal of Immunology* 6: 511-519, 1976).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with an antigenic amount, for example, from about 0.1 mg to about 20 mg of the peptide or antigenic parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen of lymph nodes of sensitized animals in a sterile fashion and carrying out fusion. Alternatively, lymphocytes can be stimulated or immunized in vitro, as described, for example, in Reading, *Journal of Immunological Methods* 53: 261-291, 1982.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine $1 \times 10^{-4}$M, aminopterin $1 \times 10^{-5}$M, and thymidine. $3 \times 10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21-23 days of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8-12 days after intraperitoneal injection. The ascites contain a higher concentration of antibodies but include both monoclonals and immunoglobulins from the inflammatory ascites. Antibody purification may then be achieved by, for example, affinity chromatography.

Recombinant antibodies are also contemplated, and in particular, single chain antibodies prepared according to Pastan et al., U.S. Pat. No. 5,608,039 (hereby incorporated by reference). In particular, humanized antibodies are contemplated. Such antibodies are non-human antibodies in which some or all of the amino acid residues are replaced with the corresponding amino acid residue found in a similar human antibody. Humanization thereby reduces the antigenic potential of the antibody.

It is not intended that the present invention be limited to specific portions of LAT for the generation of antibodies. However, the cytosolic tail of LAT is a preferred portion for generating specific antibodies. Such antibodies can be subjected to differential absorption using GST-LAT truncations to enhance specificity for different parts of the molecules.

In another embodiment, antibodies to phosphorylated LAT are contemplated. In such embodiments, phosphorylated expressed LAT protein or synthetically prepared phosphotyrosine containing peptides with the LAT sequence are used. Such antibodies are contemplated as useful for studying (and detecting) the phosphorylation of LAT and are contemplated as antibodies useful for binding activated LAT. Such reagents can be introduced into cells to target specific LAT interactions.

2. Antibody Assays

The presence of the LAT polypeptide may be accomplished in a number of ways. A wide range of immunoassay techniques are available as can be seen by reference to U.S. Pat. Nos. 4,016,043 and 4,424,279 and 4,018,653 (herein incorporated by reference). This, of course, includes both single-site and two-site, or "sandwich", assays of the non-competitive types, as well as in the traditional competitive binding assays.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen secondary complex, a second antibody specific to the antigen, labelled with a reporter molecule capable of producing a detectable signal is then added and incubated, allowing time sufficient for the formation of a tertiary complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for LAT or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated at 25° C. (or higher) for a period of time sufficient to allow binding. The incubation period will vary but will generally be in the range of about 1 minute to 2 hours, and more typically 2-40 minutes. Following the incubation period, the antibody subunit solid phase is washed and dried and incubated with a second antibody. The second antibody is linked to a reporter molecule which is used to indicate the binding of the second antibody.

An alternative method involves immobilizing LAT (or a sample containing LAT) and then exposing the immobilized LAT to specific antibody which may or may not be labelled with a reporter molecule. Depending on the amount of LAT and the strength of the reporter molecule signal, LAT may be detectable by direct labelling with the antibody. Alternatively, a second labelled antibody, specific to the first antibody is exposed to the first antibody/LAT complex to form a tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores, luminescent molecules or radionuclide containing molecules (i.e. radioisotopes).

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or toluidine are commonly used. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the tertiary complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope.

Immunofluorescent and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

3. LAT Binding Ligands

The present invention contemplates using LAT, LAT fragments, mutant LAT, and mutant LAT fragments to identify LAT Binding Ligands. Exemplary natural intracellular binding targets include protein tyrosine kinases which comprise one or more LAT binding sites and phosphotyrosine peptide fragments thereof, and protein kinases such as activated ZAP-70 and/or Syk tyrosine kinases and fragments of such targets which are capable of LAT-specific binding. Other natural LAT binding targets and fragments thereof are readily identified by screening cells, membranes and cellular extracts and fractions with the disclosed materials and methods and by other methods known in the art. For example, two-hybrid screening using ZAP-70 and/or Syk kinases are used to identify intracellular targets which specifically bind such LAT fragments. Preferred LAT fragments retain the ability to specifically bind at least one ZAP-70 and/or Syk kinase binding sites.

A wide variety of molecular and biochemical methods are available for generating and expressing LAT fragments and ZAP-70 and/or Syk kinase. For example, the ZAP-70 and/or Syk kinase and LAT or fragments thereof may be obtained by chemical synthesis, expression in bacteria such as *E. coli* and eukaryotes such as yeast or vaccinia or baculovirus-based expression systems, insect cells etc., depending on the size, nature and quantity of the LAT or fragment. The LAT fragments are of length sufficient to provide a novel peptide. As used herein, such peptides are at least 5, usually at least about 6, more usually at least about 8, most usually at least about 10 amino acids. LAT fragments may be present in a free state or bound to other components such as blocking groups to chemically insulate reactive groups (e.g. amine, carboxyls, etc.) of the peptide, fusion peptides or polypeptides (i.e. the peptide may be present as a portion of a larger polypeptide), etc. The same applies to the binding ZAP-70 and/or Syk kinase fragments, other LAT binding ligands etc.

The LAT fragments maintain binding affinity of not less than six, preferably not less than four, more preferably not less than two orders of magnitude less than the binding equilibrium constant of a full-length native LAT to the binding target under similar conditions.

Particular LAT fragments or deletion mutants are shown to function in a dominant-negative fashion. Overexpression of particular LAT fragments, for e.g. mLAT are also shown to block NFAT and AP-1 transcriptional activation mediated by OKT3 stimulated Jurkat T cells. Such LAT fragments provide therapeutic agents, e.g. when delivered by intracellular immunization-transfection of susceptible cells with nucleic acids encoding such mutants. The claimed LAT and LAT fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample.

The invention provides LAT-specific binding agents, methods of identifying and testing such agents, and their use in diagnosis, therapy and pharmaceutical development. For example, LAT-specific agents are useful in a variety of diagnostic applications, especially where disease or disease prognosis is associated with immune dysfunction resulting from improper expression of LAT or due to the signaling pathways being modified by LAT. In addition, LAT specific agents are useful in detecting clinical conditions of LAT deficiency, LAT mutations by assessing the levels of LAT expression and/or LAT phosphorylation in clinical samples, by developing assays such as PCR, Immunoblotting etc. Novel LAT-specific binding agents include LAT-specific antibodies; novel nucleic acids with sequence similarity to that of LAT; isolated ZAP-70 and/or Syk kinase binding domains; Grb2 binding domains; other natural intracellular binding agents identified with assays such as one- and two-hybrid screens; non-natural intracellular binding agents identified in screens of chemical libraries, etc.

The invention also provides nucleic acids encoding the subject LAT and LAT fragments thereof, the said nucleic acids may be part of LAT-expression vectors and may be incorporated into recombinant cells for expression and screening, transgenic animals for functional studies, etc. In addition, the invention provides nucleic acids sharing substantial sequence similarity with that of one or more wild-type (WT) LAT nucleic acids. Substantially identical or homologous nucleic acid sequences hybridize to their respective complements under high stringency conditions, for example, at 55° C. and hybridization buffer, comprising 50% formamide in 0.9M saline/0.09M sodium citrate (SSC) buffer and remain bound when subject to washing at 55° C. with the SSC/formamide buffer. Where the sequences diverge, the differences are preferably silent, i.e. or a nucleotide change providing a redundant codon, or conservative, i.e. a nucleotide change providing a conservative amino acid substitution.

The nucleic acids find a wide variety of applications including use as hybridization probes, PCR primers, therapeutic nucleic acids, etc. for use in detecting the presence of LAT genes and gene transcripts, for detecting or amplifying nucleic acids with substantial sequence similarity such as LAT homologs and structural analogs, and for gene therapy applications (including antisense approaches). Given the subject probes, materials and methods for probing cDNA and genetic libraries and recovering homologs are known in the art. Preferred libraries are derived from human immune cells, especially cDNA libraries from differentiated and activated human lymphoid cells. In one application, the subject nucleic acids find use as hybridization probes for identifying LAT cDNA homologs with substantial sequence similarity. These homologs in turn provide additional LAT and LAT fragments for use in binding assays and therapy as described herein.

Therapeutic LAT nucleic acids are used to modulate, usually reduce, cellular expression or intracellular concentration or availability of active LAT. These nucleic acids are typically antisense: single-stranded sequences comprising complements of the disclosed LAT nucleic acids. Antisense modulation of LAT expression may employ LAT antisense nucleic acids operably linked to gene regulatory sequences. Cells are transfected with a vector comprising an LAT sequence with a promoter sequence oriented such that transcription of the gene yields an antisense transcript capable of binding to endogenous LAT encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a LAT or human LAT (hLAT) fragment may be administered to the target cell, in or temporarily isolated from a host, at a concentration that results in a substantial reduction in hLAT expression. For gene therapy involving the transfusion of hLAT transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The subject nucleic acids are often recombinant, meaning they comprise a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of LAT modulatable cellular function, particularly LAT mediated T cell antigen receptor signal transduction. Generally, these screening methods involve assaying for compounds which interfere with hLAT activity such as hLAT-ZAP-70 and/or LAT-Syk kinase binding, LAT-Grb2 binding, etc. The methods are amenable to automated, cost-effective high throughput drug screening and have immediate application in a broad range of domestic and international pharmaceutical and biotechnology drug development programs. Target therapeutic indications are limited only in that the target cellular function (e.g. gene expression) be subject to modulation, usually inhibition, by disruption of the formation of a complex comprising a hLAT or hLAT fragment and one or more natural hLAT intracellular binding targets. Since a wide variety of genes are subject to ZAP-70 and/or Syk kinase regulated signaling, target indications may include viral, bacterial and fungal infections, metabolic disease, genetic disease, cell growth and regulatory disfunction, such as neoplasia, inflammation, hypersensitivity, etc. Frequently, the target indication is related to either immune dysfunction or selective immune suppression.

A wide variety of assays for binding agents are provided including labelled in vitro protein-protein and immunoassays for protein binding or complex formation, cell based assays such as two or three hybrid screens, transient transfection and co-immunoprecipitation assays, etc. For example, three-hybrid screens are used to rapidly examine the effect of transfected nucleic acids, which may, for example, encode combinatorial peptide libraries or antisense molecules, on the intracellular binding of hLAT or hLAT fragments to intracellular hLAT targets. Convenient reagents for such assays (e.g. GST fusion partners) are available in the art.

hLAT or hLAT fragments used in the methods are usually added in an isolated, partially pure or pure form and are typically recombinantly produced. The hLAT or fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring). The assay mixtures comprise at least a portion of a natural intracellular hLAT binding target such as ZAP-70 and/or Syk kinase subunit domain or Grb2 binding domains. The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the aforementioned functional groups. Candidate agents are also found among biomolecules including peptides, saccharides, fatty acids, steroids, purines, pyrimidines, derivatives, structural analogs or combinations thereof, and the like. Where the agent is or is encoded by a transfected nucleic acid, said nucleic acid is typically DNA or RNA. Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs. A variety of other reagents may also be included in the mixture. These include reagents like salts, buffers, neutral proteins, e.g. albumin, detergents, etc. which may be used to facilitate optimal protein-protein binding and/or reduce non-specific or background interactions, etc. Also, reagents that otherwise improve the efficiency of the assay, such as protease inhibitors, nuclease inhibitors, antimicrobial agents, etc. may be used. The resultant mixture is incubated under conditions whereby, but for the presence of the candidate pharmacological agent, the LAT specifically binds the cellular binding target, portion or analog. The mixture components can be added in any order that provides for the requisite bindings. Incubations may be performed at any temperature which facilitates optimal binding, typically between 4 and 40° C., more commonly between 15 and 40° C. Incubation periods are likewise selected for optimal binding but also minimized to facilitate rapid, high-throughput screening, and are typically between 0.1 and 10 hours, preferably less than 5 hours, more preferably less than 2 hours. After incubation, the presence or absence of specific binding between the hLAT and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost. Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide. Detection may be effected in any convenient way. For cell based assays such as one, two, and three hybrid screens, the transcript resulting from hLAT-target binding usually encodes a directly or indirectly detectable product (e.g. galactosidase activity, luciferase activity, etc.). For cell-free binding assays, one of the components usually comprises or is coupled to a label. A wide variety of labels may be employed, essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, non-radiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit hLAT-target binding provide valuable reagents to the pharmaceutical industries for animal and human trials. For example, LAT fragments capable of blocking T cell activation, find use in treating disease associated with undesirable cell growth, differentiation, particularly immune cell differentiation, and hypersensitivity/allergy. In addition, they find use in the inhibition of autoreactive T cells (autoimmunity), inhibition of production of deleterious T cell products (such as cytokines, lymphokines) and/or T cell activities (such as cytotoxicity, etc). Also, the invention finds use in treating diseases associated with cell movement, particularly as changes in motility are important in growth and differentiation. Thus, it could be relevant in the treatment of cancer, immunological diseases, autoimmune diseases, graft rejection and others. For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration will generally be in the range of about 100 to 500 µg/ml in the dose administered. Other additives may be included, such as stabilizers, bactericides, etc. These additives will be present in conventional amounts.

DETAILED DESCRIPTION OF SPECIFIC EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y.) which is incorporated herein by reference) which are provided throughout this document. All the information contained therein is incorporated herein by reference.

Oligonucleotides can be synthesized on an Applied BioSystems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

Assays for detecting the ability of agents to inhibit or enhance LAT binding provide for facile high-throughput screening of agent banks (e.g., compound libraries, peptide libraries, and the like) to identify antagonists or agonists. Such ZAP-70 and/or syk tyrosine kinase signaling pathway antagonists and agonists may be further developed as potential therapeutics and diagnostic or prognostic tools for diverse types of infectious diseases, autoimmune diseases and hereditary diseases, and cancer.

A. Drug Screening Assays for Agonists and Antagonists

In some embodiments, LAT (and in particular, fragments of LAT) are useful in drug screening assays designed to identify drugs that interfere with the specific binding of ZAP-70 and/or Syk kinases with its substrate as well as ZAP-70 and/or Syk kinase activity, and thereby block the activation of downstream signaling molecules.

In preferred embodiments, the invention provides an isolated LAT polypeptide, or a fragment thereof, having Grb2-specific binding affinity. The invention provides nucleic acids encoding the LAT polypeptide and LAT fragments as part of expression vectors for introduction into cells. The invention provides methods of identifying intracellular molecules which interact with LAT or LAT fragments, as well as exogenous agents (i.e. drugs) which disrupt or enhance the binding of LAT and/or fragments thereof to such intracellular targets.

The claimed polypeptide LAT and LAT fragments find particular use in screening assays for agents or lead compounds for agents useful in the diagnosis, prognosis or treatment of disease, particularly disease associated with undesirable cell growth, cell movement, differentiation and cell proliferation. One such assay involves forming mixtures of 1) LAT (or fragments thereof) and 2) an intracellular LAT-binding ligand, in the presence or absence of 3) a prospective drug candidate. The mixtures are made under conditions that permit the binding of the intracellular LAT-binding ligand to LAT (or fragments thereof) and the mixtures are then analyzed for the presence of such binding. A difference in such binding in the presence of such a drug candidate indicates that the agent is capable of modulating the binding of LAT (or fragments thereof) to an intracellular LAT-binding ligand. The assays of the present invention provide for facile high-throughput screening of compounds suspected to be able to inhibit such binding (e.g., compound libraries, peptide libraries, and the like) to identify potential drug candidates.

The compositions and methods of the present invention can be used to identify and screen for drugs that block the following LAT interactions (also see detailed description of specific embodiments):

1) Development of drugs that prevent ZAP-70 and/or other kinases from interacting and phosphorylating LAT 2) Development of drugs that prevent LAT from interacting with ZAP-70 or from getting phosphorylated.

3) Development of drugs that prevent binding of phosphorylated LAT to ligands such as Grb2 etc.

4) Development of drugs that prevent binding of Grb2 (or other ligands) to phosphorylated LAT.

An example of a drug screening assay, that can be employed to test for potential drug candidates that inhibit the specific binding of Grb2 with LAT, is given below. The suspect drug candidates are tested whether they block the binding of Grb2 to the full length LAT, or preferably to Grb2 fused to glutathione-S-transferase (GST). GST-Grb2 or GST-Grb2 is immobilized on glutathione-agarose beads and incubated for 1 hour with the indicated amount or different doses of the drug candidate. In parallel assays, the mutant LAT or αLAT antibodies are used as controls. Lysates from Jurkat T cells treated for 2 min with or without C305 are incubated with the immobilized GST-Grb2 in the presence or absence of the drug candidate (or in parallel assays with the mutant LAT). Bound proteins are eluted with sodium dodecyl sulfate-containing buffer, separated by SDS-PAGE and immunoblotted with αLAT. GST-Grb2 binds to LAT in C305 stimulated Jurkats, but not unstimulated cells. Alternatively, one can screen for drugs that block Grb2 binding to GST-LAT. Treatment with mutant LAT (mLAT) or αLAT antibodies inhibits the binding of GST-Grb2 to LAT in a dose-dependent fashion.

In other embodiments, drug screening assays that can be employed for testing potential drug candidates (for agonists), are those that overcome the inhibition of transcriptional activation of NF-AT (involved in TCR-mediated transcriptional events). Details of these assays are given below. Jurkat TAg cells, can be stably transfected with mutant LAT(Y171/191F), (in parallel assays with the wild-type or vector only), together with a reporter construct for secreted alkaline phosphatase (SEAP) driven by the NF-AT response elements. The suspect drug candidates are tested whether they overcome the inhibition of the transcriptional activation of NF-AT in OKT3 stimulated mLAT transfected Jurkat cells. (For more details, see methodology and example 7 in the experimental section). Identification of agonists are particularly useful in treatment of clinical conditions of LAT deficiency.

B. Structural and Functional Investigation of LAT.

In other embodiments, signaling molecules that bind to LAT can be identified. Based on structural and functional features of LAT (See below and experimental Section), LAT may serve as an adapter molecule that recruits multiple signaling molecules to Ligand-LAT complexes. It is believed that one or more of these proteins may link these complexes to cellular functions. Signaling proteins are predicted either to bind to pTyr within LAT in response to ligand or to bind constitutively to LAT. Identification of LAT binding partners also would provide insight into T cell, NK cell and mast cell signaling pathways. The techniques for studying the interaction of the protein(s) of interest with LAT and analyzing their role in cellular functions are as described below and in the experimental section.

i. Structure-Function Analysis of LAT

In some embodiments, LAT can be subjected to mutagenesis followed by analysis of function, i.e., to understand how does LAT regulate the following and how do mutations of LAT affect the following A. Functional assays:—all can be performed in T cells (Jurkat, normal T cells from humans or mice), mast cells, NK cells. Alternatively, non-lymphocyte cells can be studied by transient or stable expression of LAT or LAT mutants. Additionally one can express necessary kinases, receptors, accessory molecule and relevant indicator molecules. Studies can be performed in vitro, in intact cells or in animal models.

i). Protein Kinase Assays
      a. protein tyrosine kinases—Lck, Fyn, ZAP-70, Syk, Itk
      b. protein serine kinases—Raf, MEK (all), ERK (all), PAK, MEKK (all), JNKK (all), JNK (all) and all related identified and, as of now, unidentified members of these protein serine/threonine kinase families. Protein kinase C (all family members). One can identify novel kinases regulated directly or indirectly by LAT.
   ii). Calcium assays—one can analyze elevations from extra- and intra-cellular sites iii). Assays of small G proteins—(including, but not limited to Ras, Rac, Rho, cdc42, Rap) and regulators of small G protein function (including, but not limited to SOS, GAP, Vav)
   iv). Assays of protein binding—including, but not limited to those molecules shown to be directly or indirectly bound to LAT (Grb2, Grap, phospholipase C, PI-3 kinase, Vav, SLP-76, Cbl)
   v). Assays of transcriptional regulation—including, but not limited to NFAT, AP-1, Fos, Jun
   vi). Localization assays using indirect immunofluorescence and GFP chimeras. Assay by light, confocal, imaging microscopy
   vii). Assays of T cell cellular function—including, but not limited to cell shape, cell size, cell motility, cell migration, cell adhesion
   viii). Assays of tyrosine and serine/threonine phosphorylation of LAT—By using mass spectrometry, chromatography and antibodies specific for all regions of LAT
   ix). Generate panels of anti-LAT antibodies—antibodies that bind phosphorylated and non-phosphorylated regions of LAT.

B. Mutagenesis of LAT

In preferred embodiments, Structure-function analysis of LAT can be performed by mutagenesis of: i) Tyrosine residues, singly and in combinations; ii) Truncations from carboxy end and truncations of amino terminal end of the cytosolic domain (the cytosolic domain is defined approximately by amino acids 28 to 233) followed by re-generation of in-frame sequence; point mutations as indicated following truncations; iii) Deletion of putative transmembrane domain (the transmembrane domain is defined approximately by residues 5 to 27) and mutagenesis of residues in putative transmembrane domain; iv) Mutations of charged residues and cysteine residues near putative transmembrane domain.

ii. Analysis of LAT Interactions

In other embodiments, analysis of LAT interactions with other signaling proteins can be performed as given below.

A. One can study the interactions of LAT with the signaling molecules as described in the above section and in the experimental section. Also, one can map sites of interactions as stated above (mutagenesis, region-specific antibodies, etc.).

B. One can determine new and additional interactions with additional intracellular molecules, by Protein purification, such as Affinity purification using LAT protein, mRNA or cDNA as a probe. By employing two and three hybrid analysis to identify interacting molecules.

C. One can determine interactions with integral membrane proteins including, but not limited to any component of the T cell, B cell, mast cell or NK cell antigen or immunoglobulin receptors, including, but not limited to accessory or co-receptor molecules such as CD4, CD8, CD28.

iii. Analysis of the Role of LAT in T Cell, Mast Cell and NK Cell Function

In some embodiments, the function of LAT can be ascertained in various cells as given below.

A. In T cells, one can study T cell activation, T cell apoptosis, T cell anergy, T cell development and differentiation, T cell helper and killer function, T cell lymphocyte/cytokine production. In addition, one can generate transgenic animals overexpressing wild-type or mutant LAT; generation of LAT knock-outs. Also, one can generation LAT deficient T cell line as recipient for mutant forms of LAT.

B. In Mast cells, one can study granule release, cytokine production, second messenger production, gene transcription C. In NK cells one can study various functions, such as cytotoxity, cytokine and second messenger production, gene transcription iv. Structural Analysis of LAT In other embodiments, structural analysis of LAT can be performed as given below.

A. Mutation of LAT to generate cytosolic fragment followed by analysis of structure by NMR and/or crystallography.

B. Comparison of structure of mutant forms of LAT. Comparison of structure of non-phosphorylated and phosphorylated forms of LAT.

C. Modeling small molecule interactions with structural models of LAT.

iv. Inhibitors of LAT Function

In preferred embodiments, inhibitors of LAT function can be identified and/or generated as given below.

A. Generation of antibodies that bind LAT and block function, including monoclonal, single chain antibodies, recombinant antibodies B. Identify small molecules that bind LAT, by screening libraries of organics for binders, peptide binders, molecular design C. Generation of anti-sense molecules to decrease LAT expression D. Assay as above for function, interaction, localization, etc.

vi. LAT-mediated Immunodeficiency

In preferred embodiments, the compositions and methods of the present invention can be employed for developing diagnostic assays A. Screen various patients with immunodeficiencies to find patients lacking LAT or with mutated LAT. Define clinical condition(s) characterized by LAT deficiency B. Establish cell lines from such patients. Reconstitute with type. Define mutations in LAT; reexpress mutant form (patient form) in LAT deficient cell line. Use naturally occurring mutants for structure-function analysis.

C. Develop screening test for LAT deficiency or mutation.

D. Develop genetic therapy for LAT deficiency; bone marrow or T cell reconstitution.

EXPERIMENTAL

The following examples serve to illustrate certain preferred embodiments and aspects of the present invention and are not to be construed as limiting the scope thereof. In the experimental disclosure which follows, the following methodology apply:

Antibodies, Immunoprecipitation and Western Blotting: Antibodies used in the experiments were rabbit polyclonal anti-Grb2, anti-Grb2 cross-linked to agarose, anti-Cbl (C-15), and anti-Sam68 from Santa Cruz Biotechnology. Monoclonal anti-PLC-γ1, anti-phosphotyrosine (4G10) and anti-Vav, rabbit anti-p85 polyclonal were from Upstate Biotechnology. Others were anti-Flag M2 (Kodak), and anti-phosphotyrosine antibody (PY20, Transduction Laboratory). PY20 was chemically cross-linked to protein A-sepharose using dimethyl pimelimidate (DMP). GST fusion proteins were crosslinked to glutathione-sepharose with 1-Ethyl-3-(3-Dimethylaminopropyl) carbodiimide (EDC, Pierce). Anti-LAT antibodies were generated against a GST fusion protein containing the cytosolic portion of LAT (aa 31-233). The following antibodies were used: rabbit polyclonal anti-LAT antiserum (Zhang, et al., LAT: the ZAP-70 tyrosine kinase substrate that links T cell receptor to cellular activation, *Cell* 92:83-92, 1998), anti-ZAP-70 (Wange, et al., Activating and inhibitory mutations in adjacent tyrosines in the kinase domain of ZAP-70, *J. Biol. Chem.* 270:18730-18733, 1995), anti-Lck (Samelson et al., Association of the fyn protein-tyrosine kinase with the T-cell antigen receptor, *Proc. Natl. Acad. Sci. USA* 87:4358-4362, 1990), anti-CD3ε, (OKT3, Kung et al., Monoclonal antibodies defining distinctive human T cell surface anigens, *Science* 206:347-349, 1979), monoclonal anti-myc (9E10) and monoclonal anti-PLCγ1 (a gift from Dr. S. G. Rhee, NHLBI, NIH).

Jurkat T cells (ATCC) were removed from culture, washed and resuspended at $10^8$ cells/ml in RPMI. Cells were either stimulated with OKT3 ascites (1:100) (ATCC) or C305 (1:50) for 2 minutes or left untreated and lysed in 1% Brij lysis buffer (Wange et al., Activating and inhibitory mutations in adjacent tyrosines in the kinase domain of ZAP-70. *J. Biol. Chem.* 270, 18730-18733, 1995).

For treatment with calf intestine alkaline phosphatase (CIP), immunoprecipitates from $10^7$ cells were incubated with 10 units of CIP (Boehringer) in 40 μl CIP reaction buffer for 1 hour.

Purification of LAT: $10^{11}$ Jurkat E6.1 cells were stimulated for 1.5 min at $10^8$/ml in RPMI-1640 with OKT3 ascites (1:100) at 37° C. Immediately after stimulation, cells were washed with cold RPMI quickly and membrane fractions were prepared by Dounce homogenization and centrifugation. Membrane fractions were then extracted with 1% Brij lysis buffer, and insoluble material was removed by centrifugation. Membrane protein extracts were heated for 10 min at 75° C., followed by centrifugation to remove insoluble material. This supernatant was loaded onto a PY20 column, which was washed sequentially with lysis buffer containing 1% Brij 97 (25 mM Tris-HCl ph 7.6, 150 mM NaCl, 5 mM EDTA, 1 mM sodium orthoranadate, 10 μg/ml each of leupeptin, aprotinin, p-nitrophenyl-p-guanidinobenzoate), 1% CHAPS (3-[(3-cholamidopropyl)-dimethylamminio]-1-propane-sulfonate), and 0.1% CHAPS. Phospho-tyrosine containing proteins were eluted with 0.1% CHAPS buffer containing 10 mM phenyl phosphate. Eluted proteins were concentrated and subjected to SDS-PAGE. The band for p36-38 was excised and subjected to in gel S-carboxyamidomethylation followed by tryptic digestion as described, without the addition of 0.02% Tween. The resulting peptide mixture was separated by microbore HPLC using a Zorbax C18 1.0 mm by 150 mm reverse-phase column on a Hewlett-Packard 1090 HPLC/1040 diode array detector. Optimum fractions were chosen based on differential UV absorbance at 205 nm, 277 nm and 292 nm, peak symmetry and resolution; then further screened for length and homogeneity by matrix-assisted laser desorption time-of-flight spectrometry (MALDI-MS) on a Finnigan Lasermat 2000 (Hemel England). Tryptic peptides were submitted to automated Edman degradation on an Applied Biosystems Procise 494 or 477A protein sequencer (Foster City, Calif.).

cDNA cloning and Northern blotting: A YT lambda ZAP cDNA library ($10^6$ plaques) was screened with a random primed probe made from the Eco RI/Pst I fragment of an EST clone (Genbank #w74254). 20 overlapping phage clones were isolated. The cDNAs were excised from lambda phages with the rapid excision kit from Stratagene. For Northern analysis, blots with poly(A)⁺ RNA from different human tissues (ClonTech) were probed with a radiolabeled fragment of LAT cDNA or human β-actin cDNA under high stringency conditions according to the manufacturer's instruction.

Construction of LAT in expression vector and mutagenesis: The myc tag was fused to the C-terminus of LAT by replacing the Pst I/Hind III fragment of LAT in pBluescript (SK-) (Stratagene) with a double stranded oligonucleotide fragment encoding the myc tag sequence (SMEQKLI-SEEDLN) (SEQ ID NO: 16). Flag-tagged LAT was constructed by replacing the Pst I/Cla I fragment of LAT in pBluescript with a double stranded oligonucleotide fragment encoding the FLAG sequence (DYKDDDDK) (SEQ ID NO: 17). The tagged LAT cDNAs were cloned into the pcDNA3 (InVitrogen) or pEFBOS vector (See Schematic B, and Mizushima and Nagata et al., *Nuc. Acid Res.*, 18: 5322, 1990).

As shown in Schematic B, pEF-BOS carries the SV40 replication origin (311 bp of EcoRII G fragment), the promoter region of human EF-1α chromosomal gene (1.2 kb), the stuffer fragment (450 bp) from CDM8 vector (See Seed, B. *Nature* 329:840-842, 1987), and poly(A) adenylation signal from human EF-1α chromosomal gene (1.2 kb), the stuffer fragment (450 bp) from CDM8 vector and poly(A) adenylation signal from human G-CSF cDNA (700 bp Eco811~EcoRI DNA fragment) (Nagata S et al., *Nature* 319: 415-418, 1986) avin HindIII-EcoRI site of pUC119. The promoter region of EF-1α gene is from nucleotide position 373 to 1561 (Uetsuki et. al., *J. Biol. Chem.*, 264:5791-5798, 1989), which includes 203 bp 5' flanking region, 33 bp first exon, 943 bp first intron and 10 bp of the part of the second exon located at 20 bp upstream of the ATG codon. The size of the pEF-BOS is 5.8 kb, and the cDNA to be expressed can be inserted at BstXI site using BstXI adapter, or XbaI site using XbaI linker. Mutagenesis of Y171 to F and Y191 to F was done by PCR.

Immunofluorescence staining were performed as described (Sloan-Lancaster et al., Regulation of ZAP-70 intracellular localization: visualization with the green fluorescent protein. *J. Exp. Med.* 186, 1713-1724. 1997) with anti-LAT at 1:500 dilution for T cells or 1:1000 dilution for HeLa cells (ATCC), or monoclonal anti-Lck (Santa Cruz Biotech, Calif.) at 1:500 dilution.

Ligands of LAT: The nucleic acid and amino acid sequences for ZAP-70 (GENBANK ACCESSION No. L05148), Syk Kinase (GENBANK ACCESSION No. Z29630), Grb2 (GENBANK ACCESSION No. M96995), Vav (GENBANK ACCESSION No. X16316) and Cbl (GENBANK ACCESSION No. X57110) are available.

Purification of GEM Fractions and Subcellular Fractionation: $5 \times 10^7$ cells were lysed on ice in 1 ml 1% Triton in MNE buffer (25 mM MES pH 6.5, 150 mM NaCl, 5 mM EDTA), dounced 10 times, and mixed with 1 ml 80% sucrose made with MNE buffer. After transfer of the lysate to the centrifuge tube, 2 ml 30% sucrose in MNE buffer was overlaid, then 1 ml 5% sucrose in MNE was overlaid. After centrifugation for 16-18 hours at 200,000 g in a Beckman SW55Ti, 0.4 ml gradient fractions were collected from the top of the gradient. For purification of GEMs from OKT3 stimulated cells, cells were spun down quickly after stimulation and then lysed in 1 ml 1% Triton in 25 mM Tris-Cl pH 7.6, 150 mM NaCl, 5 mM EDTA, 30 mM pyrophosphate, 10 mM glycerol phosphate Schematic B

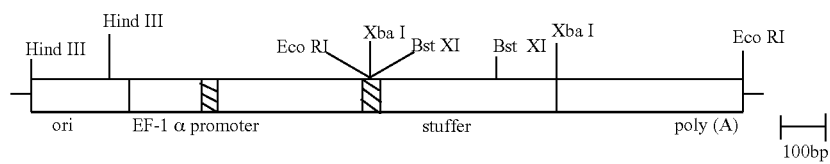

The structure of pEF-BOS. The boxes indicate SV40 origin, human EF-1α promoter region stuffer from CDM8 and poly(A) adenylation site, respectively. The slashed areas in the EF-1α promoter region are first exon and the part of second exon, respectively. The lines flanking boxes are the sequence of pUC119. Major recognition sites for restriction enzymes are shown.

Stable and transient transfections: Transfection of 293T cells was by the calcium phosphate method. Cells were harvested 36 hours after transfection. For transient transfection of Jurkat/Tag cells, $2 \times 10^7$ cells in 0.4 ml RPMI-1640, 25 mM Hepes, 2 mM Glutamine were incubated with pSX-NFAT/SEAP or pSX-AP-1/SEAP with 20 µg of pEF/LAT(wt), pEF/LAT(Y171/191F) or pEF/BOS vector DNA as control. 24 hours after transfection, transfected cells were stimulated with OKT3 ascites (1:1000) or PMA (10 ng/ml) plus ionomycin (Sigma) (1.5 µM). SEAP assay was done as described (Spencer et al., Controlling signal transduction with synthetic ligands. *Science* 262, 1019-1024, 1993; Berger et al., Secreted placental alkaline phosphatase: a powerful new quantitative indicator of gene expression in eukaryotic cells, *Gene* 66:1-10, 1988). For stable transfection of Jurkat E6.1, $10^7$ cells in 0.4 ml RPMI were electroporated using the same conditions as above. Stable transfectants were selected in the presence of 1.5 mg/ml G418 (Gibco/BRL).

Immunofluorescence Staining and Confocal Microscopy: HeLa cells transfected with the cDNA for LAT were grown on sterile glass coverslips overnight prior to antibody staining. Jurkat T cells were stained in suspension, and the cells were mounted onto coverslips immediately prior to analysis.

and 1 mM sodium orthovanadate. Lysates were prepared for sucrose gradient ultracentrifugation as above.

Mutagenesis and Subcloning: Cysteine to alanine mutations (position 26 and 29) of LAT cloned into the pCEFL expression vector (a gift from Dr. S. Gutkind, NIDR, NIH) were made with the Stratagene Quickchange kit. The LAT transmembrane domain deletion mutant (residues 1-22) was made by cloning a double-stranded linker annealed with two oligonucleotides (AATTCGCCGCCATGGCACTGTGTG (SEQ ID NO: 18) and TGCACACACAGTGCCATGGCG-GCG) (SEQ ID NO: 19), Apa L1/Xba I fragment from pEF/LAT-myc into pCEFL Eco RI/Xba I sites.

Transfection, Labeling of Jurkat Cells and 293T Cells, and Immunofluorescence: Transient and stable transfection of Jurkat cells were performed as described (Zhang, et al., LAT: the ZAP-70 tyrosine kinase substrate that links T cell receptor to cellular activation, *Cell* 92:83-92, 1998). For labeling with [$^3$H] palmitate, $2 \times 10^7$ Jurkat cells were removed from culture and resuspended in 1 ml RPMI 1640 containing 5% dialyzed fetal calf serum (FCS), 5 mM sodium pyruvate and 0.5 mCi [$^3$H]-palmitate for 3 hours. 293T cells were transfected with LAT constructs using the calcium phosphate method in 6 well plates. 24 hours after transfection, 293T cells were labeled with 0.5 mCi [$^3$H]-palmitate in 1 ml DMEM containing 5% dialyzed FCS and 5 mM sodium pyruvate, for 3 hours. The gels were fixed, treated with Enlightning (Dupont) for 30 min, dried, and exposed to film for 3-4 weeks. Immunofluorescence staining and confocal microscopy were done with 293T cells transfected with LAT constructs as described (Zhang, et al., LAT: the ZAP-70 tyrosine kinase substrate that links T cell receptor to cellular activation, *Cell* 92:83-92, 1998).

Normal Tissues and Cell Populations: Paraffin embedded normal lymphoid tissues included lymph nodes showing various forms of reactive changes (10 cases), thymuses obtained during cardiac surgery or surrounding thymomas (3), spleens removed after trauma or because of immune thrombocytopenia (4), bone marrows (6), and small intestine (2). In addition, hematopoietic tissues from three embryos aged 11-12 weeks of gestation were analyzed. Freshly frozen samples of reactive lymph nodes (3), spleen (1), and thymus (1) were also used.

Peripheral blood mononuclear cells (PBMC) were isolated from heparinized blood after Ficoll-Hypaque gradient centrifugation and depleted of plastic adherent cells. For purification of polyclonal natural killer (NK) or T cell populations, PBMC were incubated with anti-CD3 monoclonal antibody (JT3A, gift by Dr. A. Moretta, University of Genova, Italy) for 30 minutes at 4° C., followed by treatment with goat-anti-mouse-coated dynabeads (Dynal, Oslo, Norway) for 30 minutes at 4° C. The resulting CD3 negative lymphocyte populations, containing approximately 1% CD3+ cells, 20-30% HLADR+ cells and 70-80% CD16+CD56+ cells, were cultured in rIL-2 (Cetus Corp. Emeryville, Calif.). In order to obtain polyclonally activated T cell-enriched lymphocyte populations, PBMC were stimulated with 0.1% (vol/vol) PHA (Gipco Ltd, Paisley, Scotland) for 24 hours and then cultured in rIL-2.

Neoplastic Tissues: Two-hundred and sixty-four cases of nodal and extranodal hematolymphoid neoplasms were gathered from different institutions; all neoplasms had been previously characterized immunophenotypically on paraffin sections, and in many cases on frozen sections as well. All lymphomas were classified according to the International Lymphoma Study Group Classification, and included all major subtypes of Hodgkin's and Non-Hodgkin's lymphomas.

Fixatives and Tissue and Cell Processing: Tissue samples had been fixed in various fixatives, including buffered formalin, B5, Bouin, and Hollande, and embedded in paraffin. Bone marrow biopsies were fixed in B5 for 3 hours and decalcified in 0.1 M EDTA disodium salt aqueous solution for 2-8 hours. Fresh tissues were immediately frozen after biopsy in liquid nitrogen and stored at −800 C until used.

CD3+CD16−CD56− T cell and CD3−CD16+CD56+ NK cell populations were washed three times in 0.9% NaCl solution, resuspended at a concentration of $5 \times 10^6$ cells/ml and utilized for cytospin preparations (100 µl/each slide). Slides were air dried for 24 hours, then fixed in −20° C. absolute ethanol for 30 minutes, dried and used for immunocytochemical staining.

Immunostaining of Fixed Sections: Details on the production and characterization of the rabbit anti-LAT antibody are reported elsewhere (Zhang, et al., LAT: the ZAP-70 tyrosine kinase substrate that links T cell receptor to cellular activation, *Cell* 92:83-92, 1998). The immunostaining for LAT was performed on paraffin sections after antigen retrieval in microwave (3 boiling cycles, 5 minutes each at 750 watts power, with an interval of 1 minute between cycles) in citrate buffer, pH 6.0; the polyclonal antibody anti-LAT was applied at a dilution of 1:800 in TRIS-HCl buffer, pH 7.2-7.4, for 45 minutes, and was followed by biotinylated anti-rabbit antibody (30 minutes) and peroxidase-conjugated streptavidin-biotin complex (30 minutes) (Bio-S.P.A., Milan, Italy). On cryostat sections, the procedure was similar, but the microwave heating was avoided. Sections were air dried for 18 hours, and LAT was applied at the dilution of 1:100. On cytospins, the sample was subjected to microwave heating once.

In all cases of T-cell lymphomas and anaplastic large cell lymphomas (ALCL), serial paraffin sections were also stained with a polyclonal antibody anti-CD3 (Dako, Milan) (1:200; microwave antigen retrieval in 1 mM EDTA buffer, pH 8.0, 2×5' cycles). Furthermore, the cases of ALCL were also evaluated for their reactivity with the monoclonal antibody ALK1 (Dako) (1:10; microwave antigen retrieval in citrate buffer, 3×5' cycles), which recognizes a formalin-resistant epitope in the nucleophosmin-anaplastic lymphoma kinase (NPM-ALK) chimeric protein. Both CD3 and ALK1 immunostaining were performed using the same indirect immunoperoxidase technique adopted for LAT. Thymuses from embryos were also stained with polyclonal antibodies anti-CD3 and anti-TdT (Dako) (1:200; microwave antigen retrieval in 1 mM EDTA buffer, pH 8.0, 3×5' cycles, overnight incubation of the primary antibody).

Analysis of the distribution of LAT on PMBC was performed using two-colour fluorescence cytofluorometric analysis (FACS) (Ortho Cytoron Absolute) as previously described [135]. For FACS analysis of LAT in combination with monoclonal antibodies JT3A (IgG2a, anti-CD3), KD1 (IgG2a, anti-CD16) and C218 (IgG1, anti-CD56) (all antibodies provided by Dr. A. Moretta), membranes were permeabilized with 0.2% saponin (Sigma) in phosphate buffered saline (PBS) (pH 7.6) for 5 minutes, after fixation with 4% paraformaldehyde in PBS. As second reagents, fluorescein isothiocyanate (FITC)-conjugated swine anti-rabbit antibody (Dako) and phycoerythrin (PE)-conjugated isotype specific goat anti-mouse antibodies (Southern Biotechnology Associates, Birmingham, Ala.) were used.

Example 1

In this example, the purification process of LAT is described. Stimulation of the TCR on the Jurkat human T cell line by crosslinking with either C305 (anti-TCRβ, See FIG. 1A) or OKT3 (anti-CD3ε, not shown) monoclonal antibodies induced the tyrosine phosphorylation of multiple proteins, most prominently, p36-38. To define the role of p36-38 in T cell signaling, the protein was purified from activated Jurkat cells. Since, p36-38 appears to be membrane-associated, membrane fractions were prepared from OKT3 stimulated Jurkat cells and extracted with Brij97 detergent. The extracted membrane proteins were then heat-treated, which induced precipitation of about ⅔ of the protein, but not of p36-38. Anti-phosphotyrosine antibodies were used for affinity purification of phosphotyrosine-containing proteins. These were then specifically eluted with phenyl phosphate, concentrated, and resolved on SDS-PAGE. The p36-38 band was excised, digested in gel with trypsin, and the resultant tryptic peptides were resolved by microbore reverse-phase HPLC (See FIG. 1B).

Example 2

In this example, peptide sequencing and cDNA cloning of the LAT protein is described. Peptides from five HPLC fractions were either microsequenced or subjected to mass spectrometry. The peptide from fraction 40 had a molecular weight of 1721.9 daltons (See FIG. 1C). The residues at position 1, 2, 3, 11 and 15 could not be assigned unambiguously. The available sequence was then used to search the Genbank data base with the BLAST algorithm, and an EST clone from human fetal heart was found to encode the peptide fragment. Review of the Edman sequence data at the ambiguous positions was consistent with the EST sequence. The predicted molecular weight of the putative tryptic fragment predicted from the EST sequence was 1641.8 daltons. The 80.1 daltons difference suggested that a phosphate moiety of this molecular weight could be present at the Tyr residue. Two peptides from peaks 82 and 31 were shown by sequence analysis to be derived from the known tyrosine kinase substrate SLP-76. It was not clear whether these fragments of this 76 kD substrate were cleaved physiologically or during protein purification. To avoid sequencing other peptides derived from SLP-76, the masses of subsequent peptides were determined. With this strategy, it was concluded that the peptide in fraction 55 was likely to originate from SLP-76, but the masses of two peptides in fraction 48 could not be of SLP-76 origin. The sequence of the larger of these two peptides was not found in the EST clone or Genbank. Interestingly, fraction 48 contained a small amount of a second peptide with a molecular weight of 1641.6, 80.3 daltons less than the mass of the peptide isolated and sequenced from peak 40. A partial amino acid sequence revealed that this peptide was the nonphosphorylated form of the peak 40 peptide.

A cDNA library from YT cells was probed with the Eco RI/Pst I fragment of the EST clone. Thirty positive clones were isolated, of which the longest was 1.6 kb. Determination of the nucleotide sequences of these clones predicted a protein that contains the two tryptic peptide sequences found in the isolated peptides (underlined in FIG. 1D). Through comparison of the EST and cDNA sequences, it was found that the first 380 nucleotides in the EST clone were not present in the cDNA. This unknown sequence might be derived from intronic sequence. Probes from the human cDNA were used to screen a murine adult thymus library. The murine amino acid sequence obtained was 66% identical to the human sequence (FIG. 7D).

The coding sequence of human p36-38 began at nucleotide 58. The first methionine, not found within a consensus Kozak sequence, was followed by an open reading frame predicting a 233 amino acid polypeptide with a calculated molecular mass of 24,985 Daltons. One cDNA clone had an 87 nucleotide insertion at position 396, encoding an additional 29 amino acids. Of the 233 amino acids found in the majority of clones, there were a total of 39 negatively charged residues (16 Asp and 23 Glu), but only 11 positively charged residues (2 Lys and 9 Arg). The high relative negative charge could have resulted in retarded migration on SDS-PAGE leading to an apparent molecular weight of 36-38 kD, in excess of the predicted mass. The deduced amino acid sequence contained no domain homologous to known tyrosine, serine/threonine, or lipid kinases, nor did it contain SH2, SH3, or PTB domains. A single region of hydrophobic amino acids extended from residues 5 to 27, and may form an α-helical transmembrane domain. Two of the four residues N-terminal to this region were negatively charged in both human (two Glu) and murine (one Glu and one Asp). Positively charged residues (one Arg in the human and two Arg in the murine sequence), were found immediately after this hydrophobic domain. The relative charge difference across this putative transmembrane domain may determine the orientation of the molecule in the membrane, resulting in an extremely short extracellular amino-terminus and a long cytosolic tail.

Consistent with the prominent tyrosine phosphorylation of the protein in activated cells, the predicted cytosolic domain of human p36-38 contained ten tyrosines, of which nine were conserved between the human and murine proteins. Based on studies of Songyang and colleagues (Songyang et al., Specific motifs recognized by the SH2 domains of Csk, 3BP2, fps/fes, GRB-2, HCP, SHC, Syk and Vav. *Mol. Cell. Biol.* 14, 2777-2785, 1994), after phosphorylation there were five potential binding sites for Grb2 SH2 domains (YxN) at Tyrosines 110, 127, 171, 191 and 226. Tyr171 and Tyr191 have an identical Grb2-binding motif (YVNV) (SEQ ID NO: 25). A binding motif for the SH2 domain of the p85 subunit of P13 kinase was not observed. A sequence related to the consensus binding motif for N-terminal and C-terminal PLC-yl SH2 domains (YLVV (SEQ ID NO: 26), Tyr132) were found to be present. Since the p36-38 protein most likely functioned as a docking protein capable of recruiting signaling molecules, and in view of the observed features of its sequence, the name LAT for linker for activation of T cells was given.

Figures 2A, 2B:
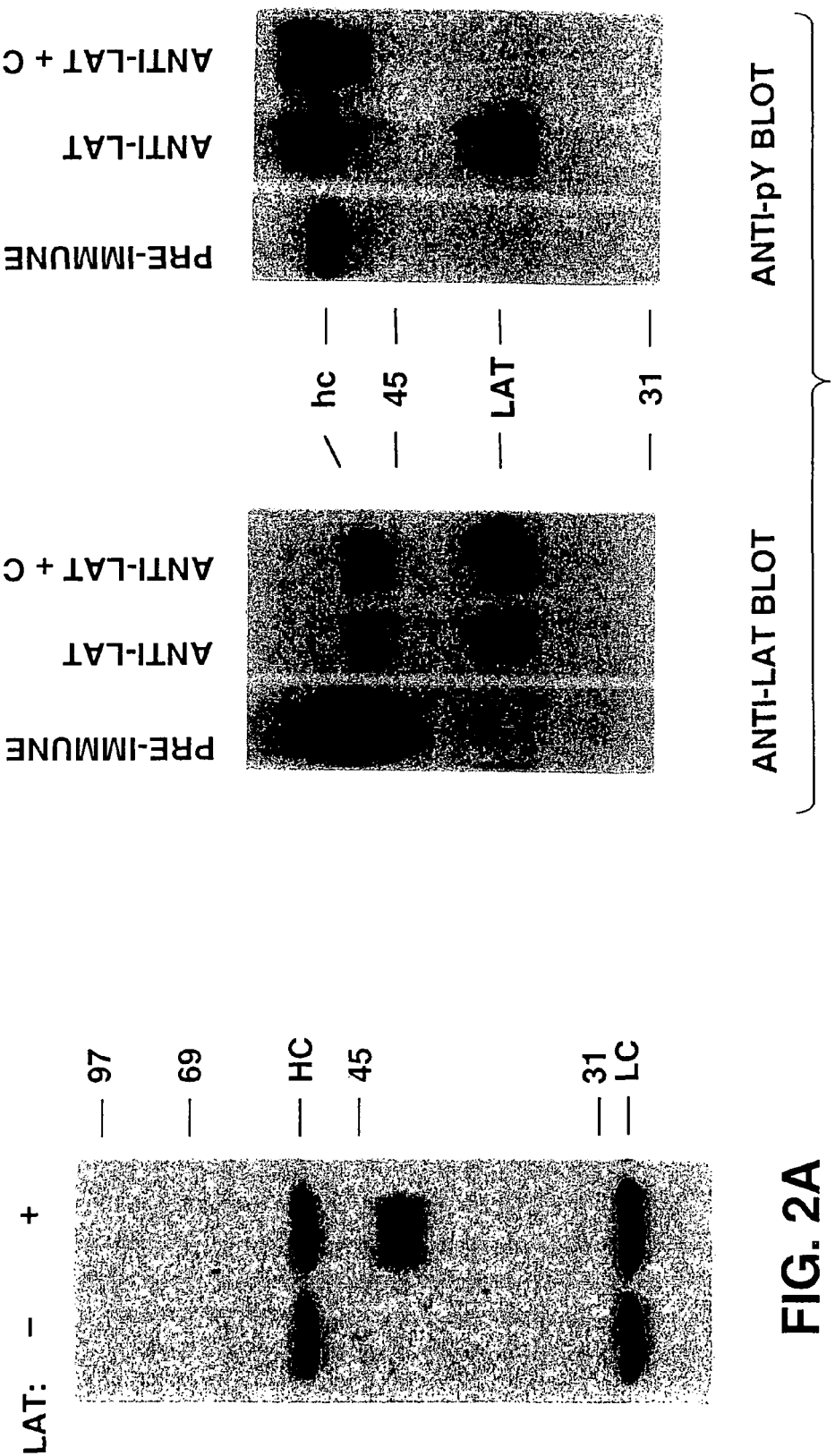
FIG. 2(A) is a representative immunoblot of 293T cells transfected with empty vector (pcDNA3) or with myc-tagged LAT in pcDNA3 (+). Post-nuclear lysates of 293T cells were immunoprecipitated with anti-myc antibody (9E10), resolved on SDS-PAGE and immunoblotted with anti-myc antibody.
FIG. 2(B) is a representative immunoblot of lysates from C305 stimulated Jurkat T cells. Proteins immunoprecipitated with rabbit anti-LAT antibody, were treated with calf intestine alkaline phosphatase where indicated, and blotted with anti-phosphotyrosine (pY) and anti-LAT antibodies.

To confirm that the cDNA clone encodes the full length LAT protein, and to resolve the discrepancy between the predicted and apparent molecular weight, the human LAT cDNA was subjected to in vitro transcription and translation. The reaction product contained a 38 kDa band that was not present when control DNA was used, confirming that the complete LAT coding sequence was present (not shown). The LAT cDNA was modified to include an epitopic tag (myc) at the C-terminus, cloned into the pcDNA3 expression vector and transfected into 293T cells (See FIG. 2A). Immunoprecipitation and blotting demonstrated a 40 kD protein in the transfected, but not non-transfected cells. These results also indicated that the LAT cDNA clone contained the entire coding region of the protein.

Figure 2C:
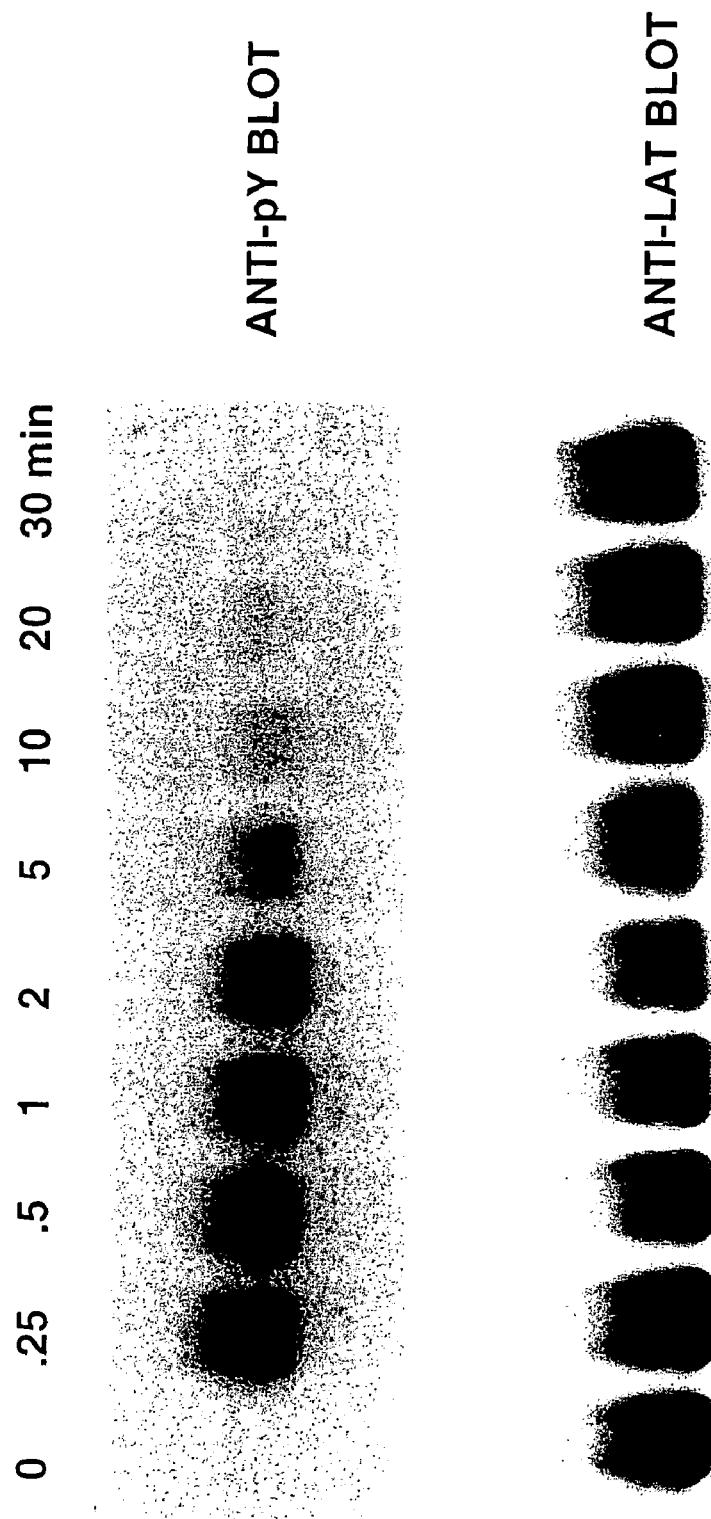
FIG. 2(C) depicts the kinetics of LAT phosphorylation in OKT3 stimulated Jurkat cells. Lysates were immunoprecipitated with anti-LAT antibody, immunoprecipitated proteins were resolved on SDS-PAGE, and blotted with anti-phosphotyrosine (pY) and anti-LAT antibodies.

To demonstrate the LAT protein in T cells, rabbit polyclonal antibodies were raised against the cytosolic portion of LAT fused to GST. The resulting antiserum was used to detect LAT in lysates of activated Jurkat cells (See FIG. 2B). The LAT antiserum precipitated and detected a doublet of 36 and 38 kD, which comigrated with bands detected with antiphosphotyrosine antibodies. Repetitive immunoprecipitation with this antiserum depleted most of p36-38 proteins from stimulated Jurkat lysate (data not shown). Phosphorylation of LAT partially interfered with the detection of this protein as demonstrated by enhanced blotting following dephosphorylation of the immunoprecipitate with calf intestinal phosphatase (CIP). This antiserum enabled the determination that LAT was rapidly tyrosine phosphorylated upon stimulation with OKT3 (See FIG. 2C). Maximal phosphorylation of LAT was seen after stimulation for 15 seconds, and after 2 min LAT was rapidly dephosphorylated. These phosphorylation kinetics were also seen in whole cell lysates (not shown). The results in this example demonstrate that the LAT cDNA encodes a protein that migrates on SDS-PAGE with an apparent molecular weight of 36-38 kD, and which is tyrosine phosphorylated, following TCR activation.

Example 3

Figure 3A:
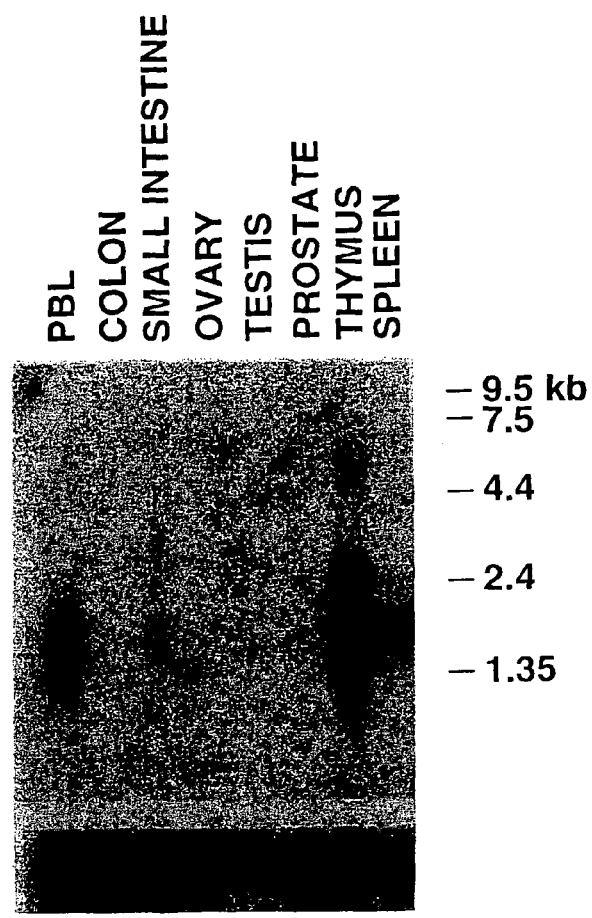
FIG. 3(A) is a representative Northern blot analysis of poly (A)+ RNA from different human tissues.
Figure 3B:
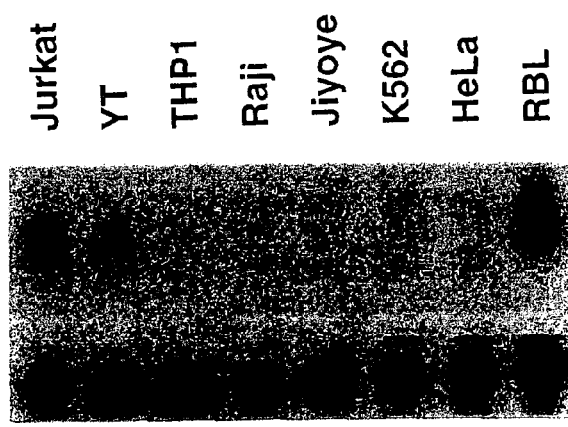
FIG. 3(B) depicts the Northern blot analysis of total RNA from different cell lines: Jurkat (T cell), YT (NK-like cell), THP1 (monocyte), Raji (B lymphoma), Jiyoye (B lymphoma), K562 (myelomonocytic cells), HeLa (fibroblastoid) and RBL (mast cell). The same membrane was also hybridized with a β-actin probe.

In this example, tissue and cellular distribution of the LAT protein is described. Northern blot analysis was performed with poly (A)+ RNAs isolated from different adult human tissues. Two transcripts (2.0 and 1.6 Kb) were seen predominantly in thymus, peripheral blood, and at a low level of expression in spleen. There were no transcripts of LAT found in other tissues (See FIG. 3A and data not shown). LAT expression was assayed in human and rat cell lines of hematopoietic origin. LAT mRNA was only found in Jurkat, YT (NK-like cells) and RBL (a rat mast cell line) (See FIG. 3B). From these data, it was concluded that LAT is expressed in T cells, NK cells, and mast cells, but not in B cells (Raji and Jiyoye) or monocytes (THP1).

The cellular localization of LAT was analyzed by immunofluorescence in COS cells, which were transiently transfected with LAT cDNA, fixed, permeabilized and incubated sequentially with anti-LAT and TRITC-conjugated goat anti-rabbit antibodies. Visualization with confocal microscopy showed that LAT was localized to the plasma membrane, and a juxtanuclear intracellular compartment (data not shown). No staining was detected in untransfected COS cells. Plasma membrane localization of endogenous LAT was also specifically detected in Jurkat cells. When cells were simultaneously stained with anti-LAT and anti-Lck antibodies, LAT and Lck were seen to co-localize at the plasma membrane and in an intracellular compartment.

Example 4

This example shows that LAT is a substrate of ZAP-70 and Syk protein tyrosine kinases. Src family and Syk family kinases are known to be directly involved in TCR-mediated signaling. To examine which tyrosine kinases can phosphorylate LAT, FLAG-tagged LAT was transiently coexpressed with Lck, Fyn, ZAP-70 or Syk, alone or in certain combinations in 293T cells. Phosphorylation of LAT was detected by anti-phosphotyrosine antibody blotting. There was no tyrosine phosphorylation of LAT when it was expressed alone in 293T cells (See FIG. 4A). When LAT was coexpressed with Lck, constitutively activated Lck (Y505F) or Fyn, only coexpression of activated Lck resulted in minimal tyrosine phosphorylation of LAT. Co-transfection with Syk resulted in marked LAT tyrosine phosphorylation. However ZAP-70 alone failed to phosphorylate LAT. ZAP-70, unlike Syk, is known to require activation by a Src kinase family member. Consequently, when LAT was cotransfected with ZAP-70 and Lck or ZAP-70 and Fyn, LAT was tyrosine phosphorylated to a level comparable to that induced by Syk. At least two unidentified tyrosine phosphorylated proteins of 90 and 60 kD co-precipitated with LAT under these conditions. Likewise, the association of LAT with endogenous Grb2 linker protein required LAT tyrosine phosphorylation induced by either Syk or the combination of ZAP-70 with either Lck or Fyn. The results in this example indicate that LAT is a substrate of ZAP-70 and Syk, and that tyrosines in LAT involved in binding to the Grb2 SH2 domain are phosphorylated by these PTKs.

Example 5

Figure 4B:
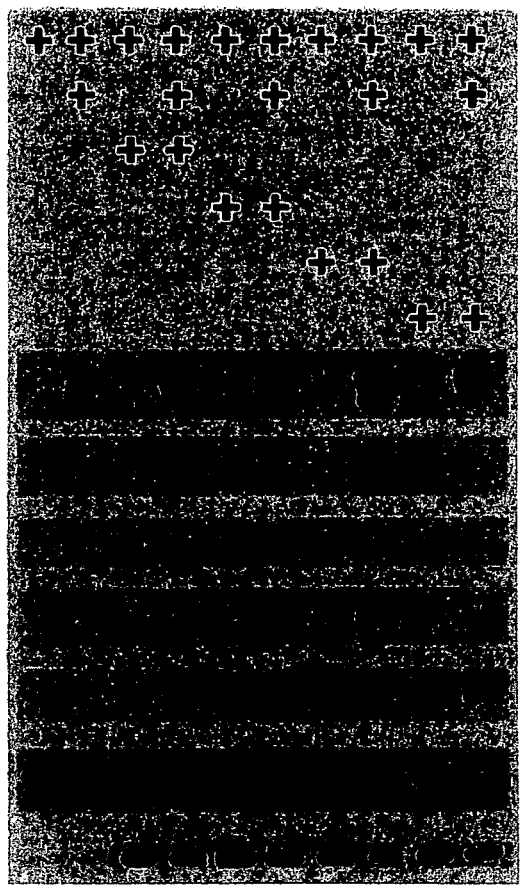
FIG. 4(B) is a representative immunoblot, showing association of LAT with signaling molecules in 293T cells. FLAG-tagged LAT was cotransfected with pCEFL/HA-Grb2, pSRα/Grap-myc, pcDNA3/HA-p85 and pcDNA3/PLC-γ1 in the absence or presence of ZAP-70 and Lck PTKs. Brij lysates of transfected 293T cells were immunoprecipitated with anti-FLAG, and association of LAT with tested proteins was determined by blotting with specific antibodies.

In this example, association of LAT with Grb2, Grap, PI3K and PLC-γ1 is shown in 293T cells. To investigate the association of LAT with critical signaling molecules, FLAG-tagged LAT in the pcDNA3 vector was cotransfected in 293T cells with plasmids expressing HA-tagged Grb2, Myc-tagged Grap, HA-tagged p85 subunit of PI3K or PLC-γ1, in the presence or absence of both ZAP-70 and Lck. LAT was immunoprecipitated with anti-FLAG antibody, and associated proteins were detected by blotting with specific antibodies. As shown in FIG. 4B, LAT tyrosine phosphorylation and association with endogenous Grb2 was induced by cotransfection with ZAP-70 and Lck as in FIG. 4A. When LAT and the two PTKs were coexpressed with HA-tagged Grb2, both endogenous Grb2 and HA-Grb2 bound to phosphorylated LAT (HA-Grb2 migrates more slowly than endogenous Grb2 on SDS-PAGE). Myc-tagged Grap, the Grb2-like protein, when coexpressed with LAT in the presence of the two PTKs, also associated with phosphorylated LAT. However, in this immunoprecipitation no endogenous Grb2 was bound to phosphorylated LAT, suggesting that Grap competes for Grb2 binding sites. HA-tagged p85 or PLC-γ1 also associated with phosphorylated LAT. Some endogenous Grb2 bound to LAT, but less than when LAT was cotransfected only with ZAP and Lck. Surprisingly, some association of LAT with PLC-γ1 was found, without co-transfection of the PTKs, suggesting either binding to undetectable tyrosine phosphorylation sites or binding via an SH2-independent mechanism.

Figure 4C:
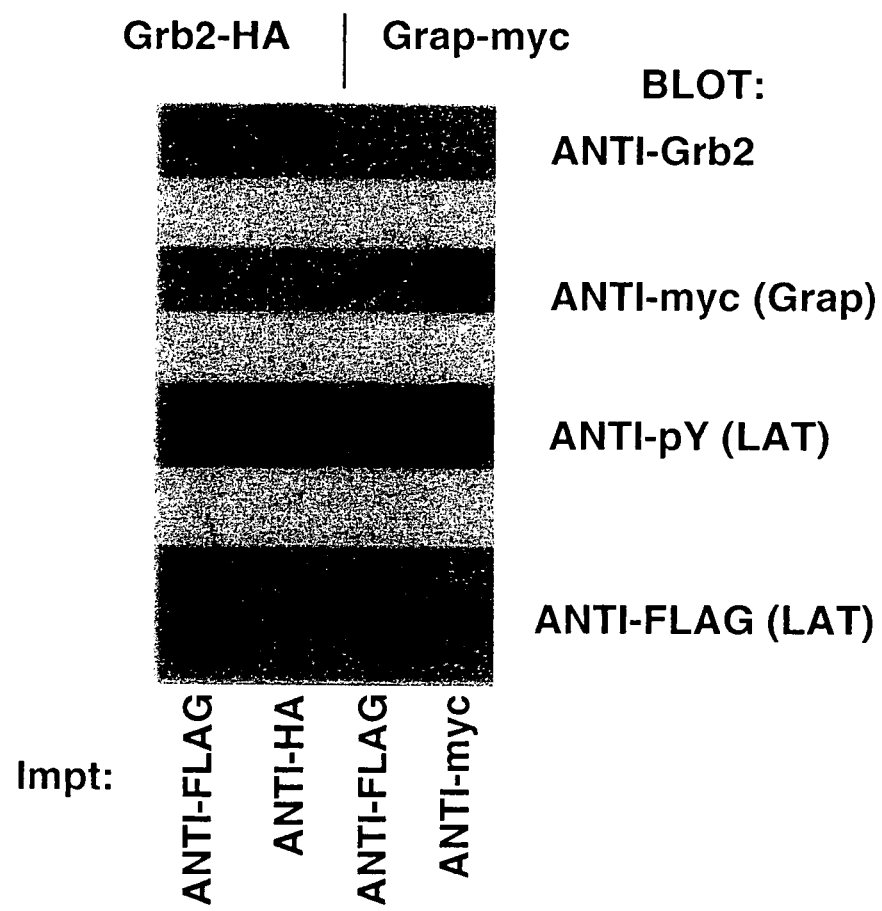
FIG. 4(C) is a representative immunoblot, showing LAT associates with Grb2 or Grap by reciprocal immunoprecipitation. Lck, ZAP-70, and LAT were cotransfected with either Grb2-HA or Grap-myc as indicated, and 293T cell lysates were immunoprecipitated with anti-FLAG and anti-HA antibodies if cotransfected with Grb2-HA, or anti-FLAG and anti-Myc antibodies if cotransfected with Grap-myc.

The above experiments were designed to demonstrate LAT associations by isolation of LAT followed by detection of associated molecules. The reciprocal approach was also performed to confirm these associations. 293T cells were co-transfected with FLAG-tagged LAT, ZAP-70 and Lck, and either HA-tagged Grb2 or myc-tagged Grap (FIG. 4C). As above, immunoprecipitation of LAT allowed detection of that fraction of Grb2 or Grap associated with LAT. In addition, immunoprecipitation of either Grb2-HA or Grap-myc allowed detection of the fraction of LAT bound to either adaptor protein. Similar experiments were performed in cells co-transfected with HA-p85 or PLC-γ1. Immunoprecipitation of these proteins revealed associated LAT (not shown). Additional experiments were performed to determine if the PTKs, ZAP-70 or Lck, could bind to LAT. No associations between LAT and either PTK were detected (not shown).

Example 6

Figure 5A:
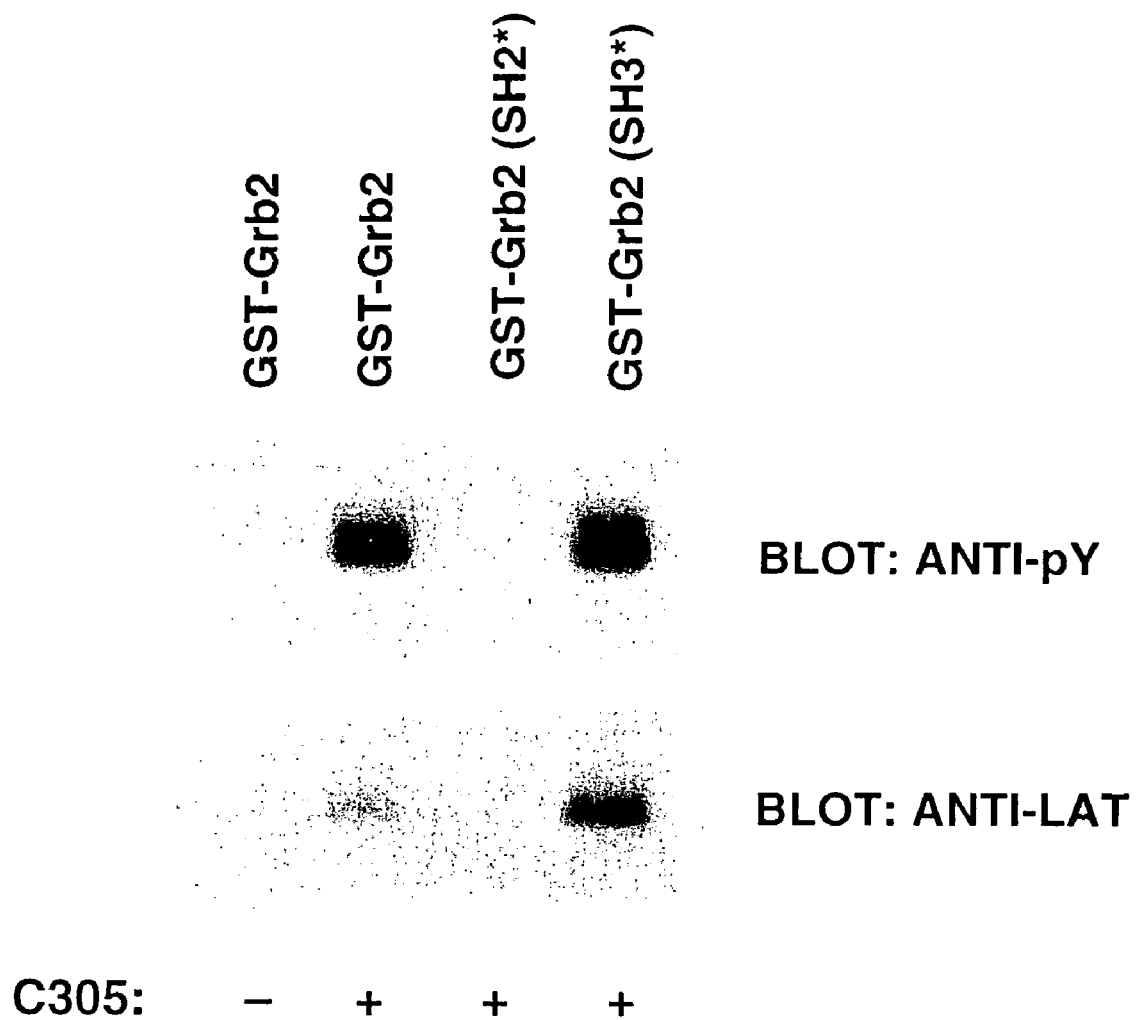
FIG. 5(A) is a representative immunoblot, showing GST-Grb2 associates with LAT through its SH2 domain. GST fusion proteins cross-linked to glutathione-agarose were used to precipitate proteins from unstimulated or stimulated with C305 Jurkat lysates. GST-Grb2 (SH2*) has a mutation in the SH2 domain (R86K). GST-Grb2 (SH3*) has mutations at both N-terminal and C-terminal SH3 domains (P49L/G203R)

In this example, association of LAT with Grb2, PLC-γ1 and PI3K is shown in Jurkat T cells. The ability of LAT to associate with signaling proteins in T cells was next evaluated. The interaction of Grb2 with p36-38 is thought to be mediated by the Grb2 SH2 domain. To test this, lysates prepared from resting and activated Jurkat cells stimulated with C305 were incubated with the immobilized fusion proteins, GST-Grb2, GST-Grb2 with an SH2 domain mutation (R86K), and GST-Grb2 with mutations at both SH3 domains (P49L/G203R). Only GST-Grb2 and GST-Grb2 with SH3 mutations bound a 36-38 kDa tyrosine phosphorylated protein from C305 stimulated Jurkat lysate (FIG. 5A). Mutation at the SH2 domain of Grb2 abolished the interaction between this 36-38 kDa protein and GST-Grb2. Subsequently the same membrane was probed with anti-LAT antibodies which confirmed that this p36-38 is LAT. LAT was not detected in material subjected to purification with GST-Grb2 from unstimulated cells or with GST-Grb2 containing the SH2 mutation.

To demonstrate the interactions in T cells directly, lysates from unstimulated and stimulated Jurkat T cells were subjected to immunoprecipitation with anti-Grb2 and anti-PLC-γ1 antibodies followed by blotting with anti-LAT. As shown in FIG. 5B, equal amounts of Grb2 or PLC-γ1 were immunoprecipitated from unstimulated or stimulated lysates. When the membrane was blotted with anti-phosphotyrosine antibody, a 36-38 kDa tyrosine phosphorylated protein was detected in association with Grb2 and PLC-γ1 only in activated T cells. This protein was identified as LAT by immunoblotting with anti-LAT antibody. CIP treatment of the immunoprecipitate enhanced LAT detection. p85 in anti-Grb2, but not in anti-PLC-γ1 immunoprecipitates in lysates of activated Jurkat cells, was also detected. There was also some low level of association between Grb2 and PLC-γ1 probably through LAT (data not shown).

Figures 1B, 1C:
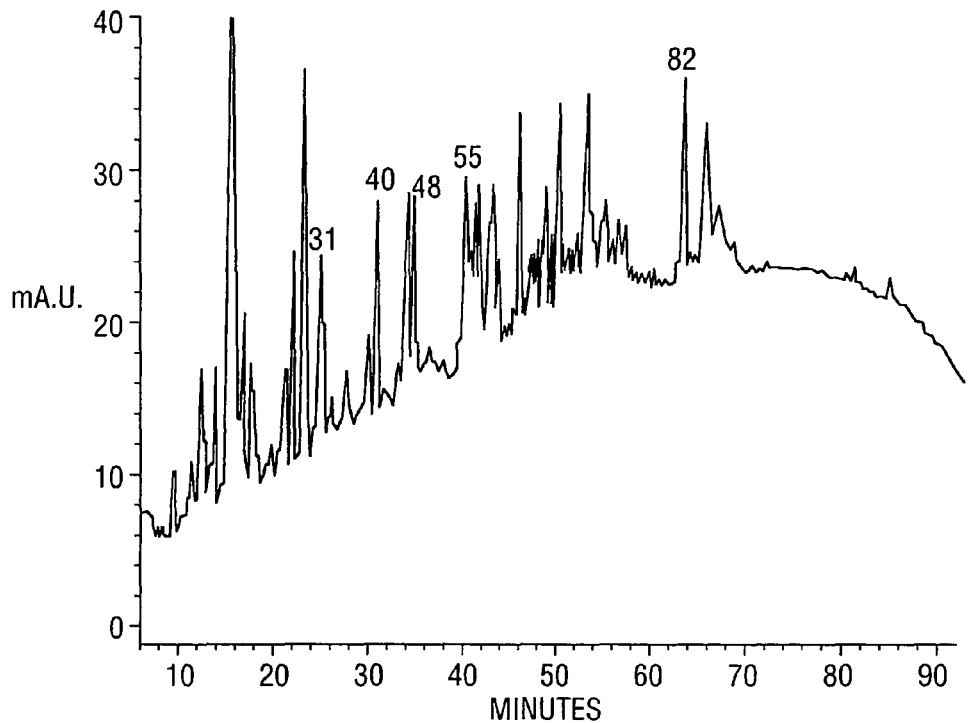
FIG. 1(B) shows the resolution by reverse-phase microbore HPLC of the affinity-purified p36-38 protein (isolated from stimulated Jurkat cells). Five peptide peaks (fraction 31, 40, 48, 55, 82) were selected for mass spectrometry and microsequencing.
FIG. 1(C) shows the analysis of peptides from the indicated peaks. The single amino acid code is used and with the following additional: X=no assignment, uppercase=full confidence assignment, lowercase=ambiguous residue and n.d.=not determined (SEQ ID NOS 20-24, respectively, in order of appearance).
Figure 5C:
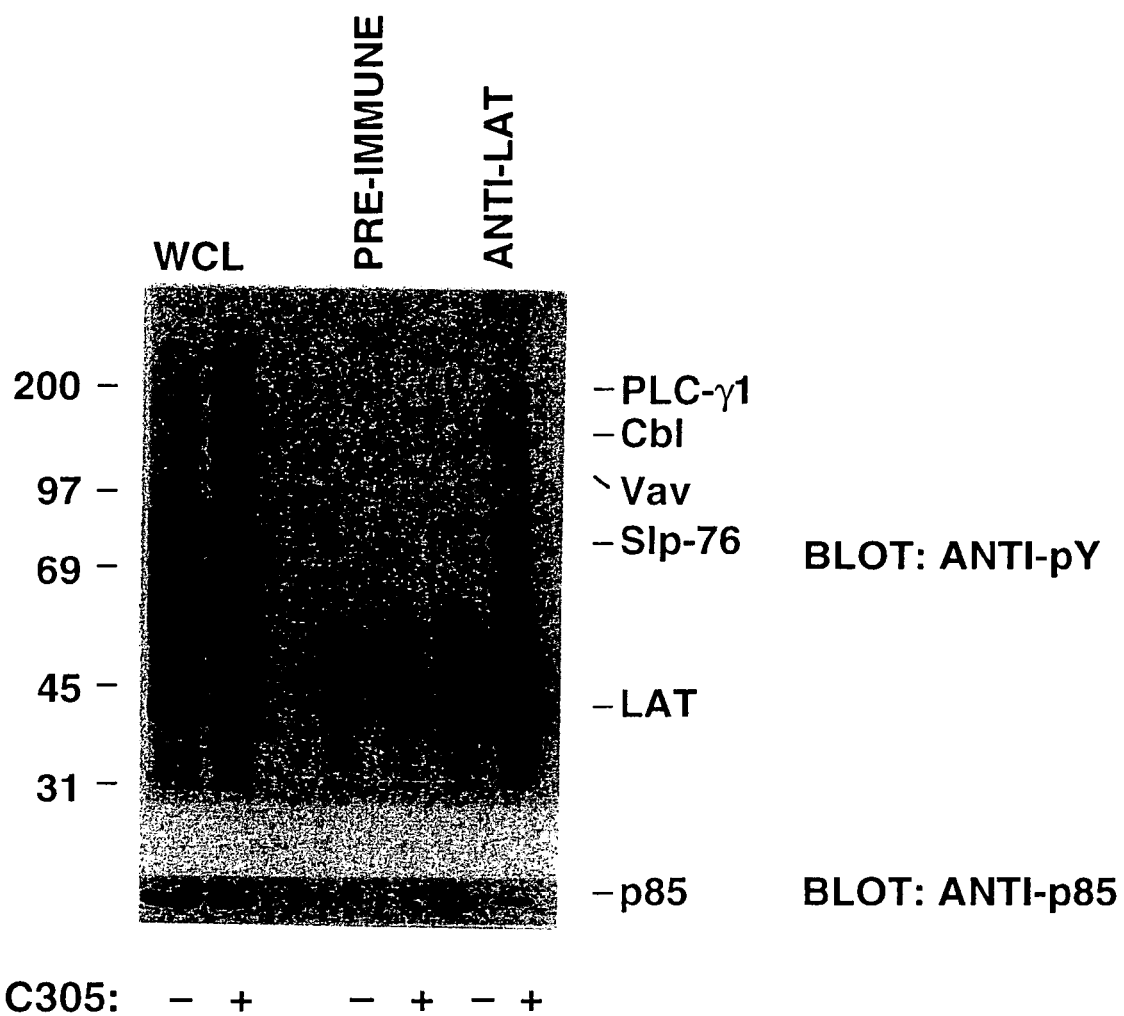
FIG. 5(C) is a representative immunoblot, depicting lysates from Jurkat T cells subjected to preimmune serum or anti-LAT antibody immunoprecipitation, resolved on SDS-PAGE and immunoblotted with anti-phosphotyrosine antibody (4G10). The same membrane was stripped and also blotted with anti-Grb2, p85, Vav, Cbl, PLC-γ1 to identify specific proteins. Only anti-p85 blotting is shown in this figure.

TCR-mediated activation results in tyrosine phosphorylation of many substrates (FIGS. 1A and 4C). To identify additional proteins, capable of binding LAT following T cell activation, anti-LAT antisera was used to immunoprecipitate LAT from lysates of resting and activated Jurkat cells. As shown in FIG. 5C, several tyrosine phosphorylated proteins with molecular weights of about 70, 76, 100, 120, 135 kD were specifically co-precipitated with anti-LAT only from lysates of stimulated Jurkat cells. By using a panel of antibodies to immunoblot known tyrosine kinase substrates, some of these proteins were identified as PLC-γ1 (135 kD), Cbl (120 kD), Vav (100 kD) (not shown). The 76 kD protein was most likely SLP-76. The associations of SLP-76 and Cbl with LAT were probably mediated indirectly through Grb2, because both bind the Grb2 SH3 domain. Vav was likely detected because of its association with SLP-76. The 70 kDa protein was not identified, and was not Sam68 or ZAP-70. Anti-LAT immunoprecipitates from stimulated Jurkat also contained the p85 subunit of PI3K and Grb2 (not shown). The results in this example, demonstrate that LAT is present in signaling complexes containing multiple critical molecules.

Example 7

In this example, the function of LAT in the TCR signal transduction pathway is shown. The hypothesis from the above studies is that the association of tyrosine phosphorylated LAT with the various signaling molecules is required for the TCR signal transduction process. To directly address the role of LAT in signaling through the TCR, wild type LAT or a mutant form of LAT was overexpressed and the effect of this overexpression examined on TCR-mediated activation. The mutant form of LAT employed in these experiments contains Phe for Tyr substitutions at both positions Y171 and Y191 (Y171/191F). These two tyrosine residues were chosen for mutagenesis because they are within identical YVNV (SEQ ID NO: 25) motifs, a motif which has previously been shown to mediate the binding of Shc to Grb2 (See Songyang et al. Specific motifs recognized by the SH2 domains of Csk, 3BP2, fps/fes, GRB-2, HCP, SHC, Syk and Vav. *Mol. Cell. Biol.* 14, 2777-2785, 1994). Moreover, phosphorylation at Tyr 191 was detected during microsequencing and mass spectrometry analysis of peptides from p36-38 (see above).

Figure 6A:
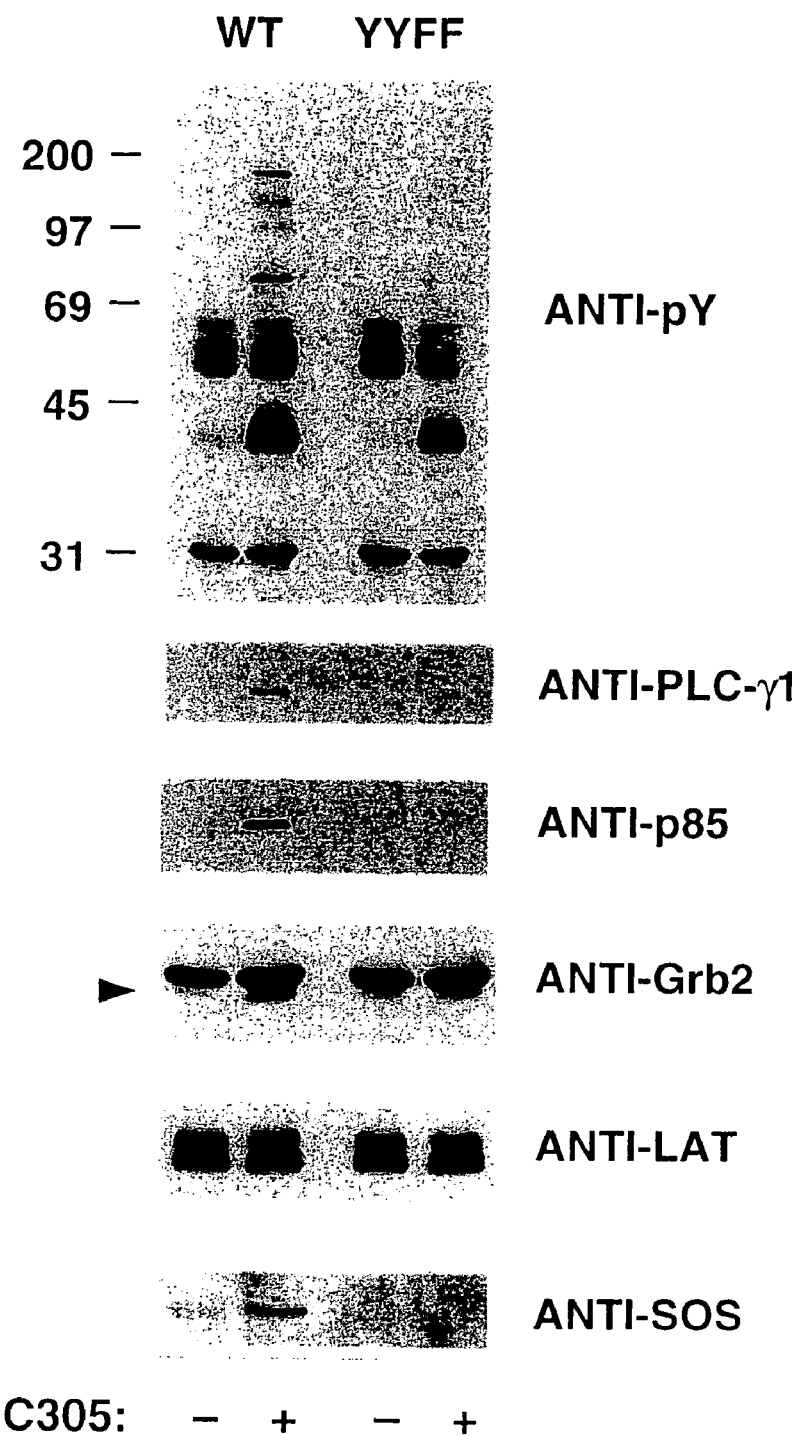
FIG. 6(A) Jurkat cells were stably transfected with wild-type (WT) or mutant (Y171/191F) LAT. Exogenous LAT was immunoprecipitated with anti-myc antibody from cells either left unstimulated or stimulated with C305 (1:50). Samples were analyzed on SDS-PAGE and blotted with 4G10. The same membrane was also blotted with anti-PLC-γ1, anti-p85, anti-Grb2, anti-SOS, and anti-LAT after stripping.

To investigate the effect of mutant LAT on protein-protein interactions, stable cell lines overexpressing myc-tagged wild type or Y171/191F LAT were established. Myc-tagged LAT was immunoprecipitated with anti-myc antibody from unstimulated or C305 stimulated transfectants. As shown in FIG. 6A, blotting with anti-LAT antibodies demonstrated that the amount of LAT immunoprecipitated with anti-myc was comparable in the two cell lines. The myc-tagged LAT appears as a doublet as does endogenous LAT. WT and Y171/191F LAT were both tyrosine phosphorylated upon stimulation, though the level of Y171/191F tyrosine phosphorylation was less than that of WT LAT, suggesting that tyrosine residues besides Y171 and Y191 are phosphorylated. Though p85, Grb2 and PLC-γ1 were observed to bind the WT form of LAT, mutations at Y171 and Y191 abolished the binding of Grb2 and p85, and greatly reduced the binding of PLC-γ1 upon activation. In addition, mutations at Y171 and Y191 prevented the association of SLP-76, Vav and Cbl, but the 70 kDa tyrosine-phosphorylated protein remained associated with LAT. Additionally, the Ras activator protein SOS was observed to co-precipitate with LAT, likely due to its interaction with Grb2. The association with SOS was also disrupted by the double Y to F mutations.

Figure 6B:
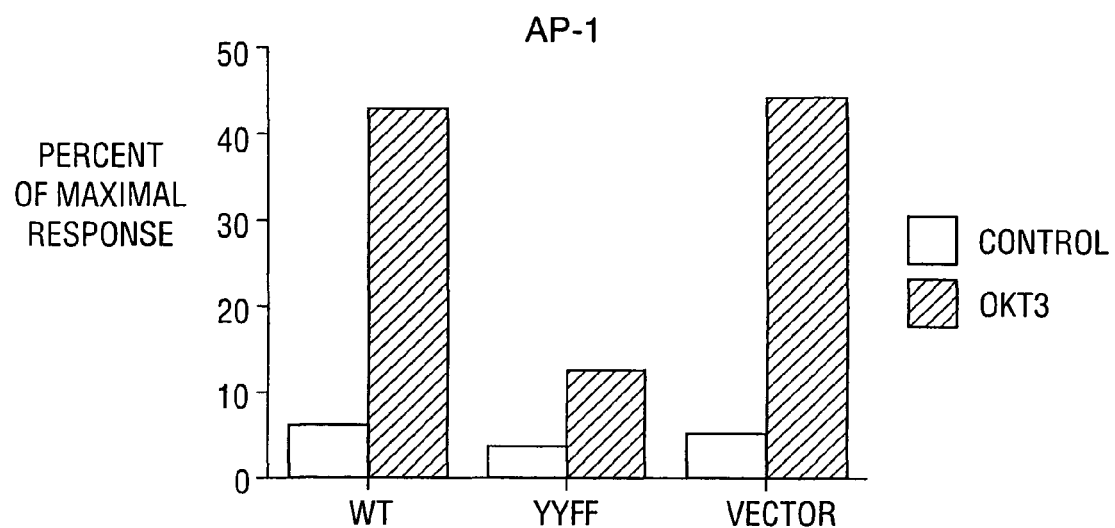
FIG. 6(B). shows secreted alkaline phosphatase (SEAP) activity and the data shown is representative of three independent experiments. Jurkat TAg cells were cotransfected with 20 μg pSX-AP-1/SEAP with 20 μg empty vector, pEF/LAT (WT), or pEF/LAT(Y171/191F), and then stimulated with OKT3 (1:1000), or stimulated with PMA and ionomycin, or left unstimulated.
Figure 6C:
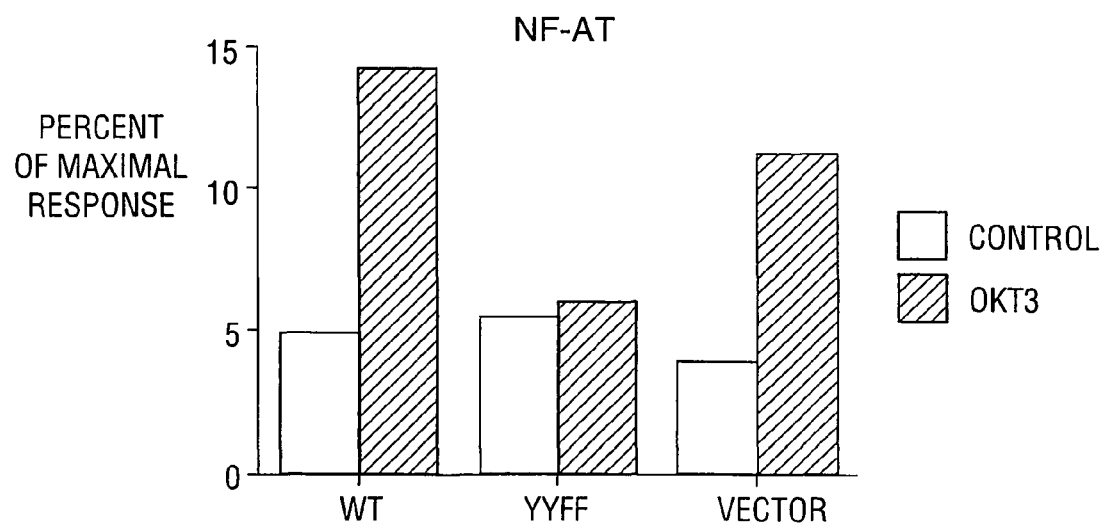
FIG. 6(C) shows SEAP activity and the data shown is representative of three independent experiments. Jurkat TAg cells were cotransfected with 20 µg pSX-NFAT/SEAP with 20 µg empty vector, pEF/LAT(Wt), or pEF/LAT(Y171/191F), and the same procedure used for stimulation and SEAP assay as in (B).

The functional effect of mutant LAT overexpression was assayed by determining the effect on transcriptional activation of AP-1 and NF-AT, both involved in TCR-mediated transcriptional events. Jurkat TAg cells, were transiently transfected with wild-type LAT, mutant LAT(Y171/191F), or vector only, together with a reporter construct for secreted alkaline phosphatase (SEAP) driven by the AP-1 or NF-AT response elements. FIG. 6B demonstrates that overexpression of WT LAT did not result in any significant effect on AP-1 transcriptional activity and only slightly increased NF-AT transcriptional activity compared with transfection of the control vector (see FIG. 6). However, overexpression of the mutant form of LAT (Y171/191F) blocked TCR-mediated AP-1 and NF-AT transcriptional activity. The results in this example indicates that LAT plays an important role in activation of transcription mediated by AP-1 and NF-AT following TCR stimulation.

From the above, it should be clear that the present invention provides methods and compositions useful for identifying signaling pathway agonists and antagonists. The methods and compositions are, in this manner, useful for identifying compounds that may be used in vitro and in vivo in the context of T cell, NK cell and mast cell responses.

Example 8

In this example the discovery of LAT palmitoylation sites and the use of LAT and LAT with modified palmitoylation sites in the TCR signal pathway is shown. Human and murine LAT contain two conserved cysteines, C26 and C29, near the punitive transmembrane domain. These features suggest that LAT could be a member of a class of transmembrane proteins modified by palmitate at juxamembrane cysteine residues. To examine whether LAT is palmitoylated, Jurkat cells were metabolically labeled with [$^3$H]palmitate. LAT was immunoprecipitated with anti-LAT antiserum, and immunoprecipitates were analyzed by SDS-PAGE and flourography. [$^3$H] palmitate was found to be incorporated into LAT. When an identical gel was treated with 1M hydroxylamine, the [$^3$H] signal was almost completely lost, indicating that the addition of palmitate to LAT was through S-acylation.

Many palmitoylated proteins, such as the Src family kinases Lck and Fyn, are targeted into glycolipid-enriched microdomains (GEMs) of the plasma membrane (Alland et al. "Dual myristylation and palmitoylation of Src family member p59$^{fyn}$ affects subcellular localization" *J. Biol. Chem.* 269:16701-16705, 1994; Shenoy-Scaria et al. "Cysteine of Src family protein tyrosine kinases determines palmitoylation and localization in caveolae" *J. Cell Biol.* 126:353-363, 1994). GEMs are operationally characterized by resistance to Triton extraction at 4° C. and are found in low-density gradients of a sucrose gradient (Simons and Ikonen "Functional rafts in cell membranes" *Nature* 387:569-572, 1997). Since LAT is palmitoylated, we next examined whether LAT localizes to GEMs. Jurkat cells were solubilized with 1% Triton, and lysates were subject to overnight ultracentrifugation over a sucrose gradient (5%/30%/40% step gradient). Among a total of 12 fractions collected, fraction 3, at the interface between 5% sucrose and 30% sucrose, contained the low-density membrane fraction including the GEMs (Brown and Rose "Sorting of GPI-anchored proteins to glycolipid-enriched membrane subdomains during transport to the apical cell surface" *Cell* 68:533-544, 1992). Fractions 8-12 from the 40% sucrose section were the Triton-soluble fractions. LAT was detected by immunoblotting and was found in both GEM and Triton-soluble fractions. LAT in the GEM fractions (e.g. fraction 3) was predominately the p36 form. Two prominent forms of LAT, p36 and p38, were detected in Triton-soluble fractions (e.g. fraction 10). LAT was more abundant in fraction 3 than in fraction 10 as determined by immunoblot. When a sample of fraction 3 was diluted 16-fold, the amount of LAT still exceeded that found in the undiluted fraction 10. As controls for GEM purification, we immunoblotted the same membrane with anti-Lck and anti-ZAP70 antibodies. Lck was observed in both GEM and Triton-soluble fractions, but ZAP-70 was found only in Triton-soluble fractions, as expected.

To study the relationship between palmitoylation and GEM localization, Jurkat cells were labeled with [$^3$H]palmitate for 3 hr, lysed in 1% Triton, and subject to ultracentrifugation on a sucrose gradient. LAT was then immunoprecipitated from GEM and Triton-soluble fractions, resolved by SDS-PAGE, and analyzed by both fluorography and anti-LAT immunoblotting. The anti-LAT immunoblot showed that an approximately equal amount of LAT was precipitated from these two fractions. However, LAT in the GEM fraction was clearly more palmitoylated, indicating that palmitoylated LAT predominately localizes to GEMs.

Figure 13A:
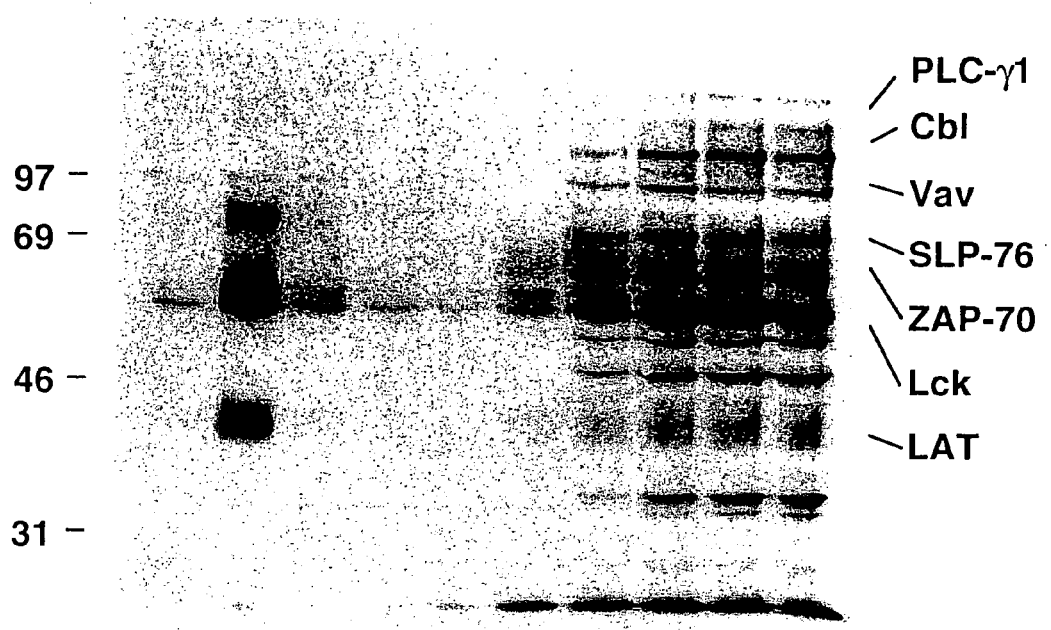
FIG. 13A shows fractions from a sucrose gradient separating a 1% Triton lysate of unstimulated Jurkat cells. Resolved by SDS-PAGE and immunoblotted with anti-phosphotyrosine antibody (4G10).

Since LAT is present in both GEM and Triton-soluble fractions, we next examined in which fraction tyrosine phosphorylated LAT can be found after stimulation of Jurkat cells. We also studied whether activation of T cells induces redistribution of other signaling molecules into GEMs. Crosslinking with the anti-CD3ε antibody, OKT3, leads to tyrosine phosphorylation of many cellular proteins and activation of T cells. Unstimulated or OKT3-stimulated Jurkat lysates were subjected to sucrose gradient centrifugation to separate GEM fractions from Triton-soluble fractions. Each fraction was analyzed by SDS-PAGE followed by immunoblotting with anti-phosphotyrosine antibody and antibodies against each individual protein. As shown in FIG. 13A, LAT and Lck were basally tyrosine phosphorylated in both GEM and Triton-soluble fractions from unstimulated cells. A tyrosine phosphorylated 80 kD diffuse band was also observed in the GEM fractions. LAT phosphorylation results in interactions with Vav, a membrane associated guanine nucleotide releasing factor. While the majority of Vav localized to the Triton-soluble fractions, some tyrosine phosphorylated Vav was detected in the GEM fractions (FIG. 13A) and fractions 5-7, as shown by anti-Vav blot in FIG. 13C.

Figure 13B:
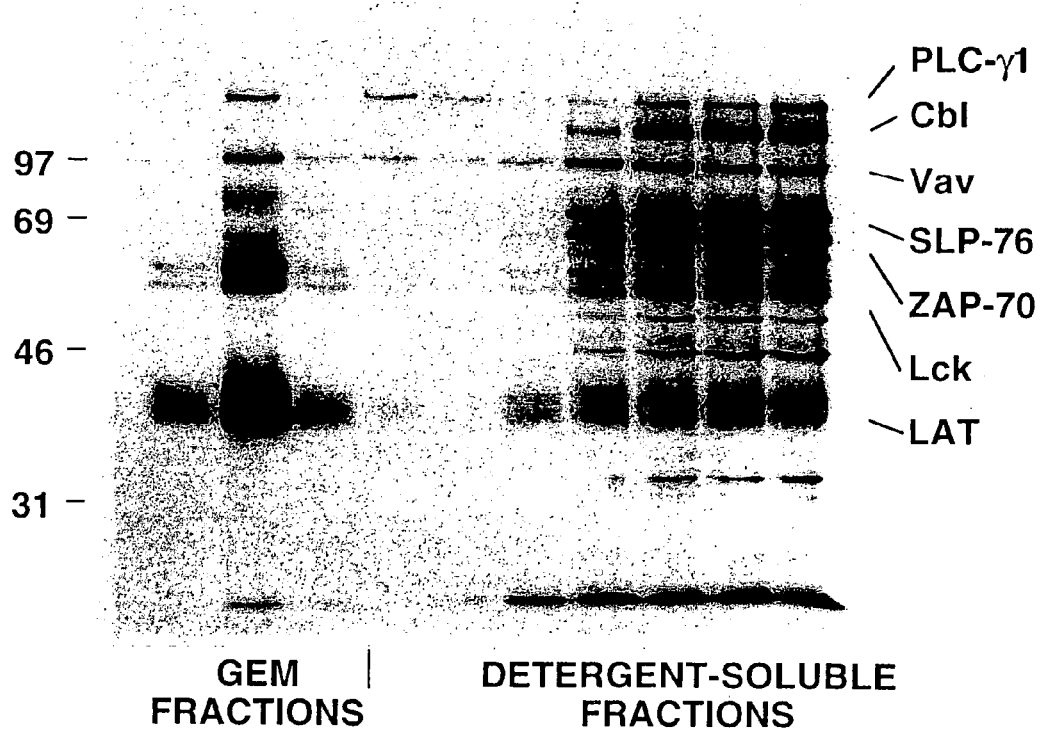
FIG. 13B shows fractions from a sucrose gradient separating a 1% Triton lysate of OKT3-stimulated Jurkat cells. Analyzed by SDS-PAGE and immunoblotted with anti-phosphotyrosine antibody.
Figure 13C:
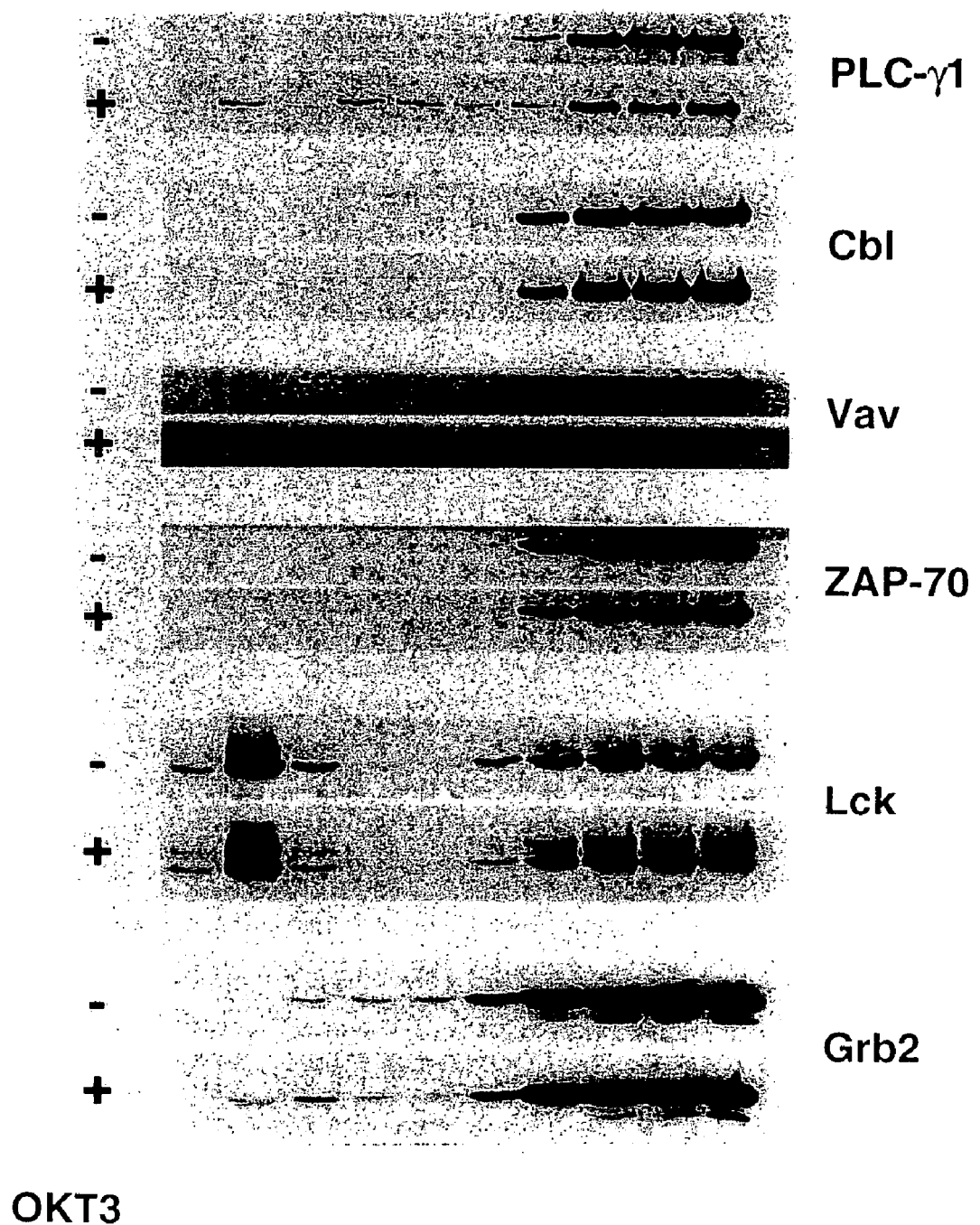
FIG. 13C shows the same membrane from (A) and (B). Was stripped and blotted with anti-PCL-γ1, CB1, Vav, ZAP-70, Lck and Grb2 antibodies.

Upon stimulation with OKT3, most tyrosine phosphorylated LAT appeared in the GEM fractions, although some was in the Triton-soluble fractions (FIG. 13B). There was no obvious change in Lck tyrosine phosphorylation, but the 60 kD form of Lck, well known to accompany TCR activation (Marth et al. "Lymphocyte activation provokes modification of a lymphocyte-specific protein tyrosine kinase (p56lck)" *J. Immunol.* 142:2430-2437, 1989), was increased in Triton-soluble fractions upon stimulation, as shown by the anti-Lck blot (FIG. 13C). Other prominent tyrosine phosphorylated proteins present in the GEM fractions upon stimulation were PLC-γ1 and Vav (FIG. 13B). Blotting with antibodies to particular signaling molecules supported the conclusion that certain molecules re-distribute to GEMs upon TCR activation (FIG. 13C). The amount of PLC-γ1 increased in the GEM fractions and fractions 5-7 upon stimulation. Like PLC-γ1, the amount of Vav in those fractions also increased after stimulation. The distribution of the p85 subunit of PI-3 kinase was similar to Vav. There was also some increase of Grb2 in the GEM fractions after stimulation (FIG. 13C). Cbl and ZAP-70 were present in Triton-soluble fractions, but they did not re-distribute into GEMs after stimulation (FIG. 13C). We used the detergent octyl-glucoside to solubilize GEMs and Triton-soluble fractions in order to assess LAT-associated proteins in the two pools. This detergent is capable of solubilizing Triton-insoluble GEMs (Brown and Rose "Sorting of GPI-anchored proteins to glycolipid-enriched membrane subdomains during transport to the apical cell surface" *Cell* 68:533-544, 1992). Following extraction with this detergent, we observed by co-immunoprecipitation that more PLC-γ1 and Vav associated with LAT in GEMs than LAT in Triton-soluble fractions, suggesting that LAT in GEMs interacts with these signaling molecules following activation.

The present invention contemplates assays for the screening of compounds that are agonistic or antagonistic for LAT activation or that are agonistic or antagonistic for LAT binding of associated molecules. For example, but not by way of limitation, it is contemplated that compounds will be screened using LAT, or portions thereof, and the methods disclosed herein (e.g. determining the extent of LAT incorporation into GEMs). In such an assay compounds that activate LAT would result in a greater amount of LAT being associated with GEMs, as compared to controls. Likewise, compounds that interfered with LAT activation would result in lesser amounts of LAT being associated with GEMs, as compared to controls. Additionally, but not by way of limitation, it is contemplated that compounds that modulate LAT binding to associated molecules (for example, but not limited to, Vav, PLC-γ1, Grb2, Sos, cbl, SLP-76, SLAP, and PI-3 kinase) will be screened using LAT, or portions thereof, and the methods disclosed herein. Modulation of LAT binding of any of these molecules can be determined by methods known to those practiced in the art (e.g. immunoblot, measurement of binding coefficients, measurement of downstream activation events).

Figure 14:
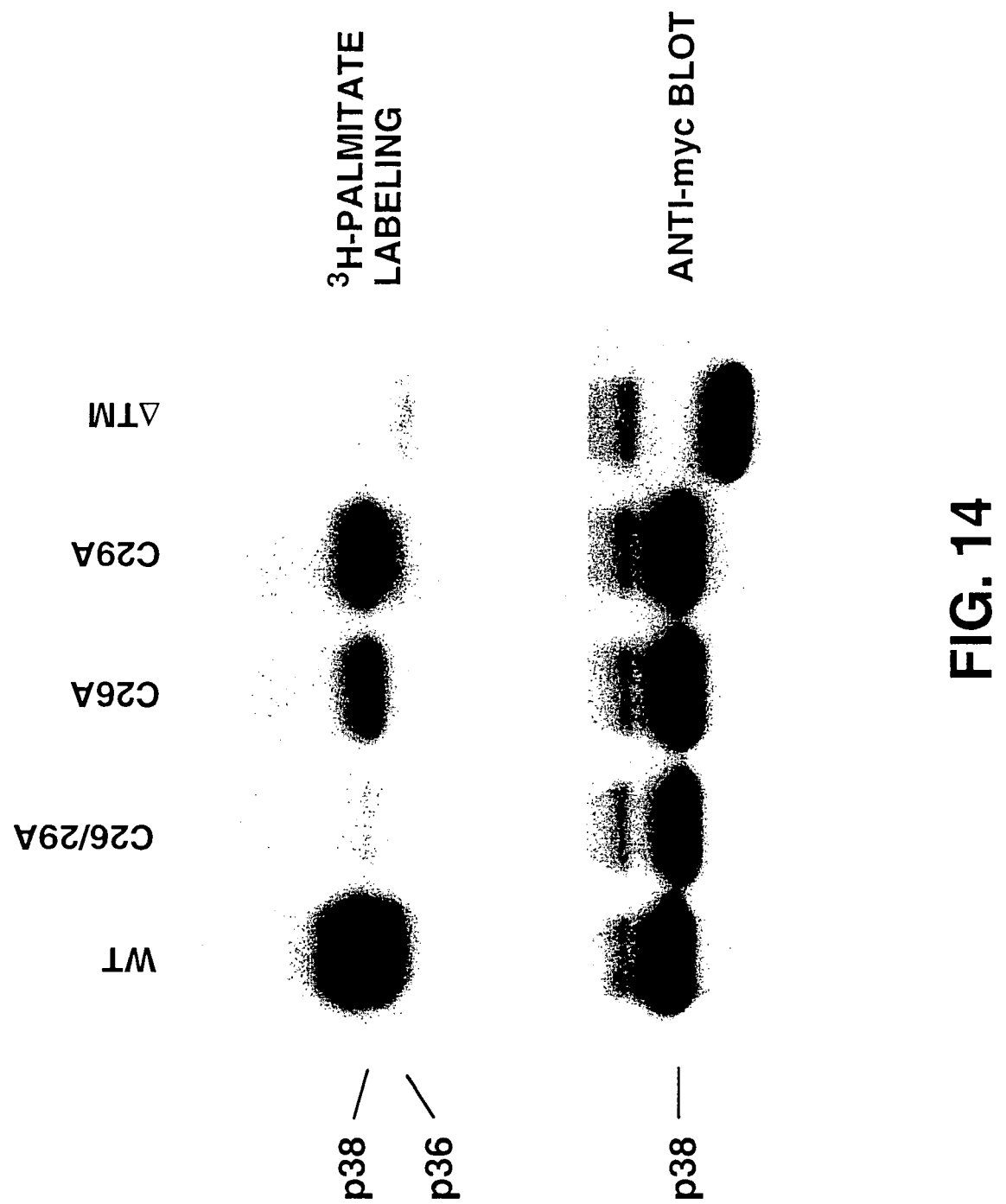
FIG. 14 shows metabolic labeling of Wt and mutant forms of LAT with [$^3$H]palmitate.

To test whether two cysteines, C26 and C29, in human LAT are the sites for addition of the palmitate moiety, we made myc-tagged LAT mutants with single cysteine to alanine mutations (C26A, C29A) and a double mutant (C26/29A). We also made a mutant LAT (Δtm) with a deletion of the N-terminal region (residues 1-22) including the transmembrane domain, to investigate the role of the transmembrane domain in LAT palmitoylation and function. T-antigen transformed human kidney fibroblasts (293T cells) were transiently transfected with these constructs and metabolically labeled with [$^3$H]-palmitate. LAT was then immunoprecipitated with anti-myc antibody from lysates of these transfected cells. As seen in FIG. 14 (top panel), two forms of LAT labeled with [$^3$H]-palmitate were detected in immunoprecipitates of wild type (wt) LAT. For the C26A mutant, only the p38 form was labeled with [$^3$H]-palmitate and the amount of $^3$H label in C26A was less than in wt. Two forms of LAT labeled with [$^3$H]-palmitate were also observed with the C29A mutant, but compared with wt, the amount of $^3$H incorporated into the p38 form was reduced and $^3$H label in the p36 form was barely detectable. A similar trace amount of $^3$H was present in the LAT double cysteine mutant (C26/29A) and in the transmembrane domain deletion mutant (Δtm).

The same samples from the above labeling experiment were loaded on another gel and analyzed by blotting with anti-myc antibody. As shown in FIG. 14 (lower panel), similar amounts of proteins were expressed in each lane. Note that the only the p314 form of LAT was detected by blotting indicating in transient transfections the p36 form was rare. These results indicate that C26 and C29 are the major sites for LAT palmitoylation. The trace amount of $^3$H in C26/29A and Δtm mutant LAT is most likely due to metabolic conversion of [$^3$H]-palmitate into [$^3$H]-amino acids, although we could not totally exclude the possibility that LAT might be palmitoylated at a low level at other site(s).

Figure 15A:
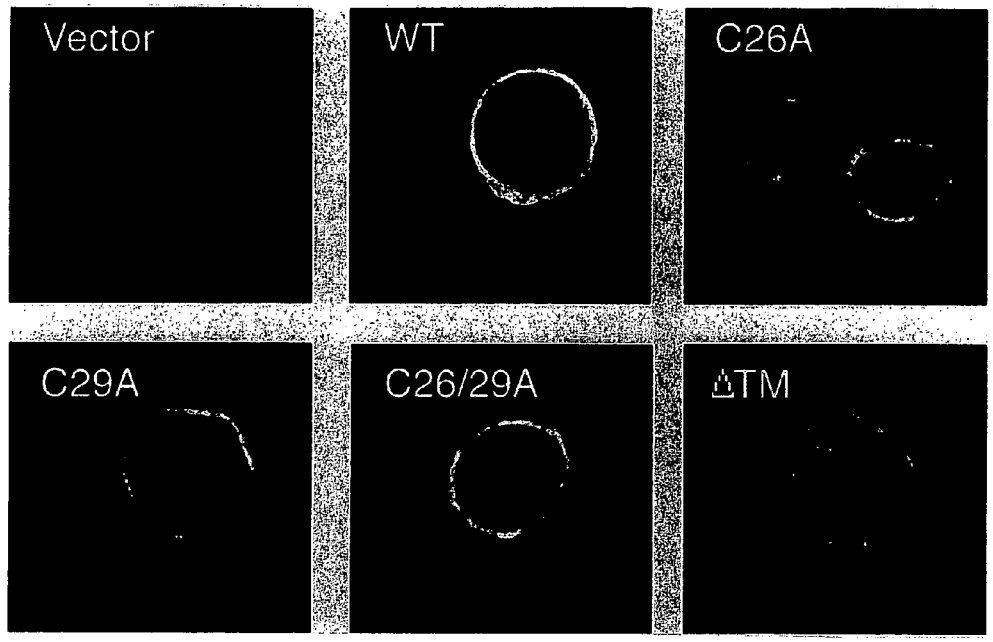
FIG. 15 shows localization of Wt and mutant LAT to the plasma membrane and glycolipid-enriched microdomains.
Figure 15B:
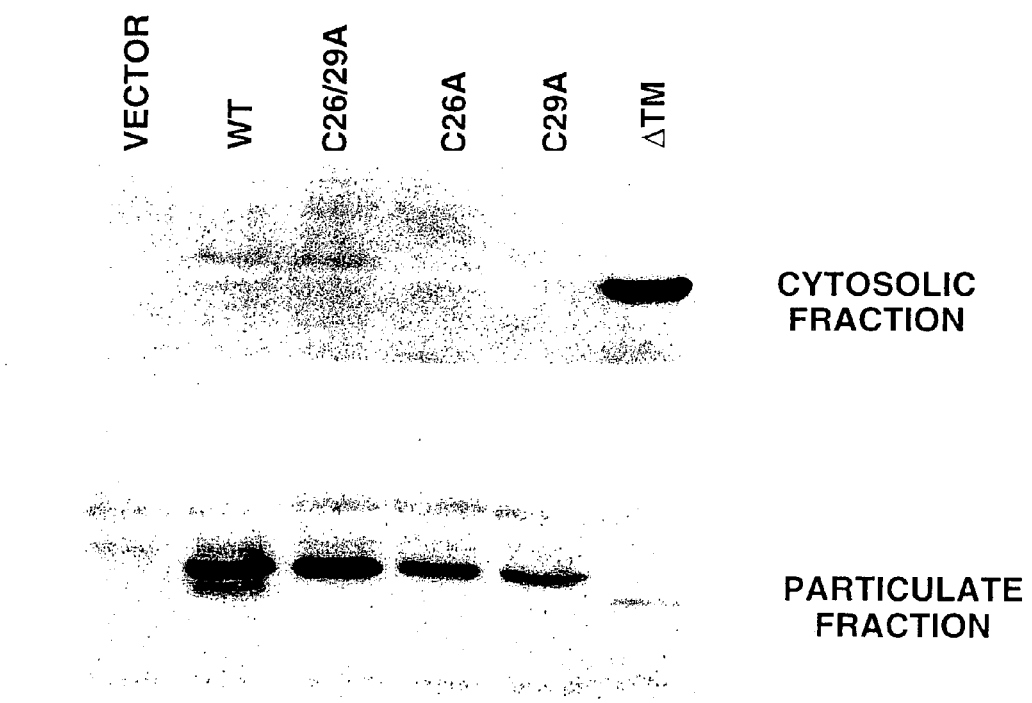

Because mutations of two cysteines, C26 and C29, affected the palmitoylation of LAT, we next tested whether these mutations also altered membrane localization and the partition of LAT into GEMs. We examined the membrane localization of wt and mutant LAT by immunofluorescence staining of transiently transfected 293T cells. There was no significant difference in localization between wt LAT and any of the cysteine mutants. However, deletion of the transmembrane domain of LAT resulted into a predominantly cytosolic localization (FIG. 15A). We also transiently transfected Jurkat/TAg cells (SV40 large T antigen transformed Jurkat cells, Clipstone and Crabtree "Identification of calcineurin as a key signaling enzyme in T-lymphocyte activation" *Nature* 357: 695-697, 1992) with LAT constructs and analyzed the subcellular distribution of LAT by fractionation of transfected cells into cytosolic and particulate fractions. Myc-tagged wt LAT, C26A, C29A, and C26/29A mutants predominantly localized to the particulate fraction, while the LAT Δtm was detected mainly in the cytosolic fraction (FIG. 15B).

Figure 15C:
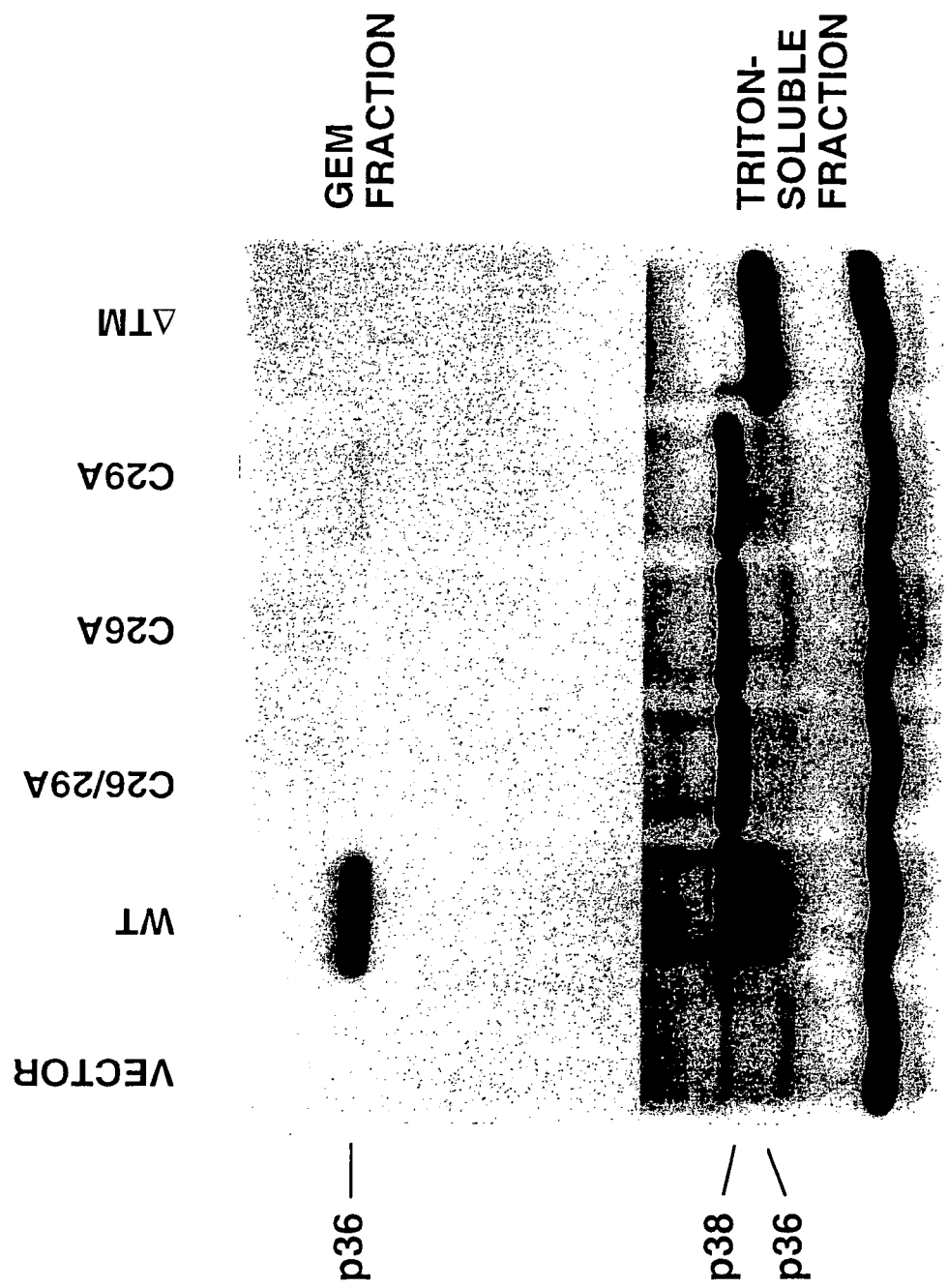
Figure 16:
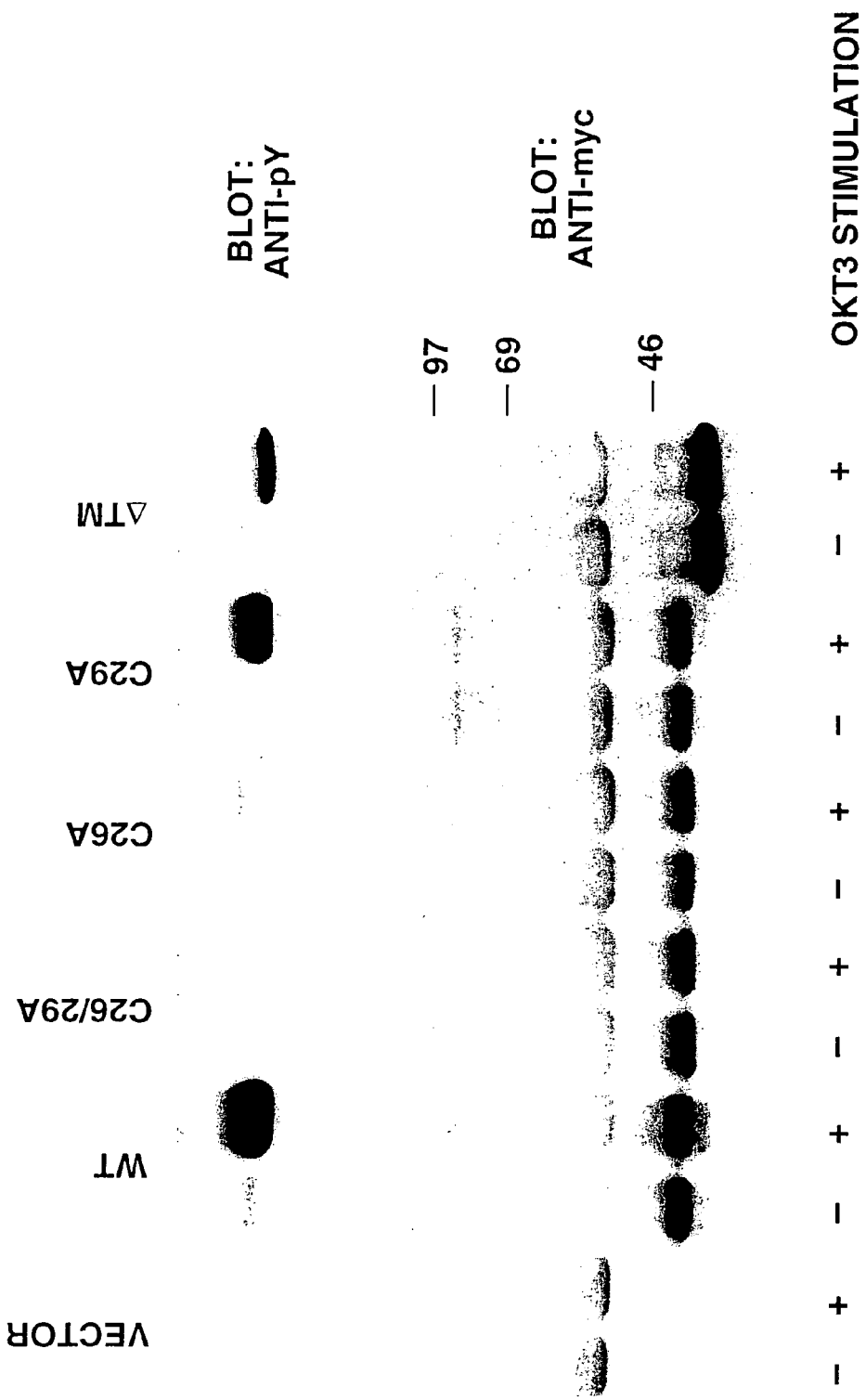
FIG. 16 shows tyrosine phosphorylation of Wt and mutant LAT.

Although C26A, C29A, and C26/29A LAT mutants all localized to the plasma membrane, it was possible that these mutations might affect the targeting of LAT into GEMs. Transiently transfected Jurkat cells were lysed in 1% Triton, and GEM fractions were purified using a sucrose gradient. Samples from fractions 3 and 10, as representatives of the GEM and Triton-soluble fractions, respectively, were analyzed on SDS-PAGE and immunoblotted with anti-myc antibody. The wt LAT and all of the LAT mutants were expressed equally in Triton-soluble fractions (FIG. 15C). Two forms of wt LAT and C29A were observed in these fractions, though the p36 form of C29A was barely detectable. Strikingly, only the wt LAT and a small amount of C29A were present in the GEM fractions. The plasma membrane localization of C26A and C26/29A and the palmitoylation of the C26A mutant were not sufficient for GEM targeting. The cytosolic LAT Δtm mutant was not seen in the GEM fraction, as expected. These results indicate that, while the transmembrane domain alone suffices for LAT plasma membrane localization, palmitoylation at C26 is essential for GEM targeting. Palmitoylation only at C29 is not sufficient for GEM targeting, but it does increase the efficiency of C26-mediated targeting.

We next addressed whether palmitoylation and targeting into GEMs were necessary for the phosphorylation of LAT by tyrosine kinases. Jurkat cells were transfected with mutant LAT constructs and stimulated with OKT3 at 36 hours after transfection. The p36 form of wt myc-tagged LAT was rapidly tyrosine phosphorylated upon OKT3 stimulation (FIG. 10). The p36 form of the C29A mutant was also tyrosine phosphorylated, though less than wt. Only very weak tyrosine phosphorylation of the p314 form of C26A or C26/29A was observed. Surprisingly, LAT Δtm was also tyrosine phosphorylated to some extent. This could be explained by the presence of activated ZAP-70 in the cytosol following stimulation. These activated ZAP-70 molecules might phosphorylate LAT Δtm in the cytosol. Endogenous LAT, however, must be in GEMs to become optimally tyrosine phosphorylated during activation. Blotting the same membrane with anti-myc antibody showed that the amount of LAT was nearly equal in all lanes. This protein blot also revealed the presence of a band at 140 kD in the wt and C29A lanes. This band could be detected with anti-LAT antibody. This 140 kD band could be a dimer of LAT, resistant to treatment with SDS and DTT. In conclusion, our results clearly show that LAT palmitoylation at C26 and C29 not only is required for LAT palmitoylation, but also is necessary for efficient tyrosine phosphorylation by tyrosine kinases during T cell activation.

The present invention contemplates the use of these LAT mutations (C26A, C29A, C26/29A and Δtm), or parts thereof, in screening assays for compounds that are agonistic or antagonistic to LAT activation. Additionally, the present invention contemplates the use of these LAT mutations in screening assays for compounds that will allow for the activation of T cells in the presence of non-functional (e.g. non-palmitoylated) LAT.

Example 9

In this example the staining of both cryostat and paraffin embedded normal tissues and cells was performed. Positive staining for LAT was crisp and mainly localized on the cell membrane and the sub-plasmalemmal area. Variable number of cells also showed diffuse cytoplasmic reactivity and, on occasion, dot-like positivity in the Golgi region. On paraffin sections, optimal staining was observed in tissues fixed in both buffered formalin or B5, whereas occasionally some background staining was observed for tissues fixed in Bouin or Hollande. Decalcification of bone marrow specimens in EDTA did not affect LAT immunoreactivity.

In the thymus, expression of LAT was identifiable throughout all stages of thymocyte differentiation, including the large cortical blasts. In embryos of 10-12 weeks of gestation, thymuses already showing a lobular architecture contained lymphoid cells that expressed LAT and CD3, but were negative for TdT indicating that LAT expression precedes TCR rearrangement.

In peripheral lymphoid tissues, LAT-positive lymphocytes were located in the known T cell areas in lymph nodes and spleen, and the immunoreactivity paralleled that obtained with anti-CD3 in both frozen and paraffin sections. In the small intestine, intraepithelial T cells were also positive for LAT. In bone marrow, LAT was expressed by the sparse T lymphocytes present in interstitial spaces, and also by platelets and megakaryocytes, that exhibited a strong reactivity in the cytoplasm; all other hematopoietic cells were negative. Reactivity for LAT was also noticed on tissue mast cells, in the form of delicate plasma membrane and granular cytoplasmic labeling. In all tissues, non-T cell components, including B cells, macrophages, plasmacytoid monocytes, epithelioid histiocytes and dendritic cells, were completely negative for LAT. Similarly, LAT was not expressed on endothelial cells and epithelia, including thymic epithelium and Hassal bodies.

On peripheral blood mononuclear cells (PBMC), LAT was expressed, in addition to CD3+ T cells, on resting CD16+ and CD56+ NK cells. LAT staining was also found on T and NK cells in culture with rIL-2; on CD3−CD16+CD56+ NK cells purified from PBMC, LAT was obviously expressed, although the intensity of reactivity was much weaker than that recognized on purified CD3+ T cells.

Example 10

In this example the staining of LAT in neoplastic tissues was performed. Neoplastic cells in all cases of Hodgkin's (15 cases) and B cell non-Hodgkin's lymphomas (100 cases) (see Table 1) were negative for LAT, but contained variable amounts of LAT-reactive non neoplastic T cells. In T-cell lymphomas (excluding anaplastic large cell lymphomas (ALCL)), LAT stained 14/14 lymphoblastic lymphomas, 42/43 peripheral T cell lymphomas, and 11/12 NK/T cell lymphomas. The intensity of reactivity and the percentage of labeled cells varied among different types of T cell lymphomas. In lymphoblastic lymphomas all neoplastic cells were strongly labeled by anti-LAT; in contrast, in peripheral T cell and NK/T cell lymphomas the reactivity was intense in 214/53 (52.14%) cases, and it was recognizable in the vast majority of cells in 50/53 (94.3%). LAT expression showed no substantial differences in peripheral T cell lymphomas with relationship to primary location, cell morphology, and immunophenotype, with the exception of NK/T cell lymphomas, which were more frequently characterized by weaker and a lower number of labeled cells.

TABLE 1

Details of negative LAT staining Hodgkin's lymphomas and malignant B cell lymphomas analyzed.

| | N° of cases |
|---|---|
| Hodgkin's Lymphomas | |
| Lymphocyte predominance | 2 |
| Nodular sclerosis | 10 |
| Mixed cellularity | 2 |
| Total | 15 |
| B-cell lymphomas | |
| I. Precursor B-lymphoblastic leukemia/lymphoma | 8 |
| II. Peripheral B-cell neoplasms | |
| B-cell chronic lymphocytic leukemia/small lymphocytic lymphoma | 14* |
| Lymphoplasmacytoid lymphoma | 3 |
| Mantle cell lymphoma | 11** |
| Follicle center cell lymphoma, follicular | 16 |
| Marginal zone B-cell lymphoma | |
| nodal | 1 |
| extranodal | 4 |
| Hairy cell leukemia | 6 |
| Myeloma | 8 |
| Diffuse large B-cell lymphoma | 25*** |
| Burkitt's lymphoma | 4 |
| Total | 100 |

*one with immunoblastic transformation;
**one "blastoid" variant;
***included four T-cell rich B large cell lymphomas and three CD30+/ALK1− anaplastic large cell lymphomas.

The ALCL included 39 extra-cutaneous and 5 purely cutaneous cases; on the basis of the expression of at least one T cell marker (CD3, CD5, CD14, CD43, CD45R0, TCR-β) and no B cell markers (CD20 or CD79a), 25 cases were classified as T cell and 19 cases as null-cell phenotype. 14 cases (31.14%) reacted with LAT; all were represented by extra-cutaneous lymphomas, ten of them were of T cell phenotype, while four were null-cell. LAT positive ALCL showed intense reactivity in 5/14 (35.7%) cases, and it was recognizable in the vast majority of cells in 10/14 (71.4%).

LAT and CD3 expression was compared in T cell and NK/T cell lymphomas (excluding ALCL). In T-lymphoblastic lymphoma, LAT positivity was more intense and diffuse than CD3. Among peripheral T cell lymphomas, only two LAT-negative cases were observed. One was a large cell lymphoma presenting an aberrant phenotype with loss of CD3, CD5, CD43 and TCR-β, the other LAT negative case was a NK/T which strongly expressed cytoplasmic CD3. Three cases of LAT positive cutaneous T-cell lymphomas did not express CD3 (two also lacked CD5), but were positive for CD2, CD4 and TCR-β.

A comparison was made regarding LAT, CD3 and ALK1 expression in ALCL. The distribution of LAT, CD3 and ALK1 in ALCL is reported in Table 2. Seven ALCL cases were LAT+CD3+, 7 were LAT+CD3−, 9 were LAT−CD3+, and 21 were LAT−CD3−. Among ALCL T cell type (25 cases), CD3 labeled a higher number of cases (19/25; 76%) than LAT (10/25; 40%). Interestingly, LAT and CD3 expression in ALCL T cell type was discordant in a significantly higher number of cases than in other peripheral T cell lymphomas (12/25 versus 4/55, respectively; Fisher's exact test: p<0.001). Immunostaining for ALK1 was available in 42 cases and showed nuclear±cytoplasmic positivity in 10. Although the majority of ALK1+ cases were LAT+ (6/10), in comparison with ALK1− cases (14/32), this difference was not statistically significant (Fisher's exact test: p=0.059).

Expression of LAT was also examined in Hematopoietic, non-lymphoid neoplasms. In chronic myeloproliferative disorders and myelodysplastic syndromes, cytoplasmic LAT expression was consistently identified in normal and atypical megakaryocytes, including the micro-megakaryocytes typically found in chronic myeloid leukemia and myelodysplasia. Among 214 cases of acute non-lymphoid leukemia, the only positive cases were represented by two megakaryocytic leukemias, where the blast cells were labeled in their cytoplasm; an additional case of chronic myeloid leukemia in blastic transformation contained two cell populations, one formed by myeloid blasts (myeloperoxidase and CD34 positive), another by megakaryocytic blasts, expressing LAT, Factor VIII-related antigen and CD34. In all

TABLE 3

Details of LAT, CD3 and ALK1 staining in anaplastic large cell lymphomas (ALCL).

| | T-cell type | | | | Null-cell type | | | |
|---|---|---|---|---|---|---|---|---|
| | LAT+ CD3+ | LAT+ CD3− | LAT− CD3− | LAT− CD3+ | LAT+ CD3+ | LAT+ CD3− | LAT− CD3− | LAT− CD3+ |
| ALK1 positive | 3 | 3 | 1 | | | | 3 | |
| ALK1 negative | 4 | | 4 | 8 | | 4 | 12 | |
| ALK1 n.a.* | | | 1 | 1 | | | | |
| Total | 7 | 3 | 6 | 9 | 0 | 4 | 15 | 0 |

*ALK1 not assessable because only B5-fixed specimens available and poor reactivity of anti-ALK1 on this fixative.

pathological conditions, reactivity of LAT on megakaryocytes was strong and particularly helpful in the identification of abnormal forms; moreover, it was frequently stronger than that of other megakaryocytic markers on paraffin sections, such as Factor-VIII related antigen and CD61. 4/5 cases of mastocytosis showed LAT positivity, including 3 of 3 cases of cutaneous mastocytosis, and 1 of 2 cases of systemic mastocytosis, as with normal mast cells, LAT expression in neoplastic mast cells was finely granular in the cytoplasm and delicate on the cell membrane, a pattern of staining that clearly differed from that on T cells.

We claim:

1. An isolated polynucleotide encoding the polypeptide comprising the sequence of SEQ ID NO:4.

2. The isolated polynucleotide of claim 1, wherein the polynucleotide comprises the polynucleotide sequence beginning at base pair (bp) 58 through by 759 of sequence of SEQ ID NO: 1.

3. The isolated polynucleotide of claim 1, wherein the polynucleotide is contained in a recombinant expression vector.

4. The polynucleotide sequence of claim 3, wherein the expression vector containing the polynucleotide sequence is contained within a host cell.

5. An isolated polynucleotide sequence that hybridizes under high stringency conditions of 55° C. and a hybridization buffer comprising 50% formamide in 0.9M saline/0.09M sodium citrate (SSC) buffer, and remains bound when subject to washing at 55° C. with the SSC/formamide buffer to the nucleic acid sequence of SEQ ID NO: 1, wherein the complement of the isolated polynucleotide encodes a polypeptide comprising the sequence of SEQ ID NO:4.

6. The polynucleotide of claim 1, wherein the polynucleotide comprises a label.

7. The polynucleotide of claim 1, wherein the polynucleotide comprises at least one nucleotide analogue.

8. An isolated polynucleotide sequence that (i) has at least 85 percent sequence identity to a polynucleotide sequence beginning at base pair (bp) 58 through by 759 of SEQ ID NO. 1 and (ii) hybridizes to a complement of a polynucleotide sequence beginning at base pair (bp) 58 through by 759 of SEQ ID NO: 1 under high stringency conditions of 55° C. in a hybridization buffer comprising 50% formamide in 0.9M saline/0.09M sodium citrate (SSC) buffer, and remains bound when subject to washing at 55° C. with the SSC/formamide buffer to a complement of the nucleic acid sequence that encodes a polypeptide comprising the sequence of SEQ ID NO: 4.

9. The isolated polynucleotide of claim 8, wherein the polynucleotide is contained in a recombinant expression vector.

10. The polynucleotide sequence of claim 9, wherein the expression vector containing the polynucleotide sequence is contained within a host cell.

11. The polynucleotide of claim 8, wherein the polynucleotide comprises a label.

12. The isolated polynucleotide of claim 5, wherein the polynucleotide is contained in a recombinant expression vector.

13. The polynucleotide sequence of claim 12, wherein the expression vector containing the polynucleotide sequence is contained within a host cell.

14. The polynucleotide of claim 5, wherein the polynucleotide comprises a label.

15. An isolated polynucleotide sequence that (i) has at least 85 percent sequence identity to the polynucleotide sequence beginning at base pair (bp) 58 through by 759 of SEQ ID NO. 1 and (ii) hybridizes to a complement of by 58 through by 759 of SEQ ID NO: 1 under high stringency conditions of 55° C.

in a hybridization buffer comprising 50% formamide in 0.9M saline/0.09M sodium citrate (SSC) buffer, and remains bound when subject to washing at 55° C. with the SSC/formamide buffer to a complement of the nucleic acid sequence that encodes a polypeptide comprising the sequence of SEQ ID NO: 4, wherein the polynucleotide sequence comprises by 79 through by 867 of SEQ ID NO: 2.

16. The polynucleotide sequence of claim 15, wherein the polynucleotide is contained in a recombinant expression vector.

17. The polynucleotide sequence of claim 16, wherein the expression vector containing the polynucleotide sequence is contained within a host cell.

18. The polynucleotide sequence of claim 15, wherein the polynucleotide comprises a label.

19. The polynucleotide sequence of claim 8 wherein the polynucleotide has at least 90 percent sequence identity to SEQ ID NO. 1.

20. The polynucleotide sequence of claim 8 wherein the polynucleotide has at least 95 percent sequence identity to SEQ ID NO. 1.

* * * * *

SEQUENCE LISTING

<160> NUMBER OF SEQ ID NOS: 26

<210> SEQ ID NO 1
<211> LENGTH: 1060
<212> TYPE: DNA
<213> ORGANISM: Homo sapiens

<400> SEQUENCE: 1

| | | | | | |
|---|---|---|---|---|---|
| gactctgccc | ttgaggggcc | taggggtgca | gccagcctgc | tccgagctcc | cctgcagatg | 60 |
| gaggaggcca | tcctggtccc | ctgcgtgctg | gggctcctgc | tgctgcccat | cctggccatg | 120 |
| ttgatggcac | tgtgtgtgca | ctgccacaga | ctgccaggct | cctacgacag | cacatcctca | 180 |
| gatagtttgt | atccaagggg | catccagttc | aaacggcctc | acacggttgc | ccctggcca | 240 |
| cctgcctacc | cacctgtcac | ctcctaccca | ccctgagcc | agccagacct | gctccccatc | 300 |
| ccaagatccc | cgcagcccct | tgggggctcc | caccggacgc | catcttcccg | gcgggattct | 360 |
| gatggtgcca | acagtgtggc | gagctacgag | aacgaggaac | cagcctgtga | ggatgcagat | 420 |
| gaggatgagg | acgactatca | caacccaggc | tacctggtgg | tgcttcctga | cagcaccccg | 480 |
| gccactagca | ctgctgcccc | atcagctcct | gcactcagca | ccctggcat | ccgagacagt | 540 |
| gccttctcca | tggagtccat | tgatgattac | gtgaacgttc | cggagagcgg | ggagagcgca | 600 |
| gaagcgtctc | tggatggcag | ccgggagtat | gtgaatgtgt | cccaggaact | gcatcctgga | 660 |
| gcggctaaga | ctgagcctgc | cgccctgagt | tcccaggagg | cagaggaagt | ggaggaagag | 720 |
| ggggctccag | attacgagaa | tctgcaggag | ctgaactgag | ggcctgtgga | ggccgagtct | 780 |
| gtcctggaac | caggcttgcc | tgggacggct | gagctgggca | gctggaagtg | gctctggggt | 840 |
| cctcacatgg | cgtcctgccc | ttgctccagc | ctgacaacag | cctgagaaat | cccccgtaa | 900 |
| cttattatca | ctttggggtt | cggcctgtgt | ccccgaacg | ctctgcacct | tctgacgcag | 960 |
| cctgagaatg | acctgccctg | gccccagccc | tactctgtgt | aatagaataa | aggcctgcgt | 1020 |
| gtgtctgtgg | aaaaaaaaa | aaaaaaaaa | aaaaaaaaa | | | 1060 |

<210> SEQ ID NO 2
<211> LENGTH: 1460
<212> TYPE: DNA
<213> ORGANISM: Homo sapiens

<400> SEQUENCE: 2

| | | | | | |
|---|---|---|---|---|---|
| accccatctt | catctggcct | tgactctgcc | cttgaggggc | ctaggggtgc | agccagcctg | 60 |
| ctccgagctc | ccctgcagat | ggaggaggcc | atcctggtcc | cctgcgtgct | ggggctcctg | 120 |
| ctgctgccca | tcctggccat | gttgatggca | ctgtgtgtgc | actgccacag | actgccaggc | 180 |
| tcctacgaca | gcacatcctc | agatagtttg | tatccaaggg | gcatccagtt | caaacggcct | 240 |
| cacacggttg | cccctggcc | acctgcctac | ccacctgtca | cctcctaccc | accctgagc | 300 |
| cagccagacc | tgctccccat | cccaagatcc | ccgcagcccc | ttgggggctc | caccggacg | 360 |
| ccatcttccc | ggcgggattc | tgatggtgcc | aacagtgtgg | cgagctacga | gaacgagggt | 420 |
| gcgtctggga | tccgaggtgc | ccaggctggg | tggggagtct | ggggtccgtc | ctggactagg | 480 |
| ctgacccctg | tgtcgttacc | cccagaacca | gcctgtgagg | atgcagatga | ggatgaggac | 540 |
| gactatcaca | acccaggcta | cctggtggtg | cttcctgaca | gcaccccggc | cactagcact | 600 |
| gctgccccat | cagctcctgc | actcagcacc | ctggcatcc | gagacagtgc | cttctccatg | 660 |
| gagtccattg | atgattacgt | gaacgttccg | gagagcgggg | agagcgcaga | agcgtctctg | 720 |

-continued

| | |
|---|---|
| gatggcagcc gggagtatgt gaatgtgtcc caggaactgc atcctggagc ggctaagact | 780 |
| gagcctgccg ccctgagttc ccaggaggca gaggaagtgg aggaagaggg ggctccagat | 840 |
| tacgagaatc tgcaggagct gaactgaggg cctgtggagg ccgagtctgt cctggaacca | 900 |
| ggcttgcctg gacggctga gctgggcagc tggaagtggc tctggggtcc tcacatggcg | 960 |
| tcctgccctt gctccagcct gacaacagcc tgagaaatcc cccgtaact tattatcact | 1020 |
| ttggggttcg gcctgtgtcc cccgaacgct ctgcaccttc tgacgcagcc tgagaatgac | 1080 |
| ctgccctggc cccagcccta ctctgtgtaa tagaataaag gcctgcgtgt gtctgtgttg | 1140 |
| agcgtgcgtc tgtgtgtgcc tgtgtgcgag tctgagtcag agatttggag atgtctctgt | 1200 |
| gtgtttgtgt gtatctgtgg gtctccatcc tccatggggg ctcagccagg tgctgtgaca | 1260 |
| cccccttct gaatgaagcc ttctgacctg gctggcact gctgggggtg aggacacatt | 1320 |
| gccccatgag acagtcccag aacacggcag ctgctggctg tgacaatggt ttcaccatcc | 1380 |
| ttagaccaag ggatgggacc tgatgacctg ggaggactct tttagttctt acctcttgtg | 1440 |
| gttctcaata aaacagaacg | 1460 |

<210> SEQ ID NO 3
<211> LENGTH: 1260
<212> TYPE: DNA
<213> ORGANISM: Mus musculus

<400> SEQUENCE: 3

| | |
|---|---|
| ggcacgagca ggcggggagc aagaaagggg caggtacagc tgggcacggg gatcgtgcag | 60 |
| ctggtagctg gggcacgggc cccagctctg gctctggggc gagcaccttt ccagagccaa | 120 |
| cactgctctc aactcagtcc agcaagagag gggagccatc cagccccgaa aggatacggc | 180 |
| tgcctactgc cgggcggatc ccaggctgga gcccgcttgg tcccatacccc ctgctgccac | 240 |
| tctgtctcga ggggctgcag tgcagcaggg cctgtggcag gtgctctgca gatggaagca | 300 |
| gacgccttga gccggtgggg gctgggcctc ctgctgctgc ccttcttggt cacgctcctg | 360 |
| gctgccctgt gcgtgcgctg ccgtgagttg ccagtctcct atgacagcac ttccacagag | 420 |
| agtttgtacc caagaagcat cctcatcaag ccacctcaaa taaccgtccc ccgaacacct | 480 |
| gctgtttcct accctctagt cacttccttc ccacccctga ggcagccaga cctgctcccc | 540 |
| atcccgagat ccccacagcc ccttgggggt tccatcgga tgccatcttc ccagcagaat | 600 |
| tcagatgatg ccaacagtgt ggcaagctac gagaaccagg agccagcctg taagaatgtg | 660 |
| gatgcagatg aggatgaaga cgactatccc aacggctacc tagtggtgct gcctgacagt | 720 |
| agtcctgctg ccgtccctgt tgtctcctct gctcctgtgc ctagcaaccc tgaccttgga | 780 |
| gacagtgcct tctctgtgga gtcgtgtgaa gattacgtga atgttcctga gagtgaggag | 840 |
| agcgcagagg cgtctctgga tgggagccgg gagtatgtga atgtgtcccc agagcagcag | 900 |
| ccagtgacca gggctgagct ggcctctgtg aactcccagg aggtgaaaga cgaaggagaa | 960 |
| gaggaagggg tggatggaga ggaagctccc gactatgaga atctacagga gcttaactga | 1020 |
| aagcctactg cagctgtctg tcctgaaact ggacttgctg gggtgtcgct aagaggatcc | 1080 |
| catttgatct ctgccttgcc acagcctgag aatcttcccc taacttattg tcactttggg | 1140 |
| gtccagtctg tgtccccaat attctgtacc ttctgataaa gcctgagaat gaatctggtt | 1200 |
| ccagccagac catgtcatgg aataaaggcc atgtgacata aaaaaaaaaa aaaaaaaaaa | 1260 |

<210> SEQ ID NO 4
<211> LENGTH: 233
<212> TYPE: PRT

-continued

<213> ORGANISM: Homo sapiens

<400> SEQUENCE: 4

Met Glu Glu Ala Ile Leu Val Pro Cys Val Leu Gly Leu Leu Leu Leu
1               5                   10                  15

Pro Ile Leu Ala Met Leu Met Ala Leu Cys Val His Cys His Arg Leu
                20                  25                  30

Pro Gly Ser Tyr Asp Ser Thr Ser Ser Asp Ser Leu Tyr Pro Arg Gly
            35                  40                  45

Ile Gln Phe Lys Arg Pro His Thr Val Ala Pro Trp Pro Pro Ala Tyr
50                  55                  60

Pro Pro Val Thr Ser Tyr Pro Pro Leu Ser Gln Pro Asp Leu Leu Pro
65                  70                  75                  80

Ile Pro Arg Ser Pro Gln Pro Leu Gly Gly Ser His Arg Thr Pro Ser
                85                  90                  95

Ser Arg Arg Asp Ser Asp Gly Ala Asn Ser Val Ala Ser Tyr Glu Asn
            100                 105                 110

Glu Glu Pro Ala Cys Glu Asp Ala Asp Glu Asp Asp Tyr His
        115                 120                 125

Asn Pro Gly Tyr Leu Val Val Leu Pro Asp Ser Thr Pro Ala Thr Ser
130                 135                 140

Thr Ala Ala Pro Ser Ala Pro Ala Leu Ser Thr Pro Gly Ile Arg Asp
145                 150                 155                 160

Ser Ala Phe Ser Met Glu Ser Ile Asp Asp Tyr Val Asn Val Pro Glu
                165                 170                 175

Ser Gly Glu Ser Ala Glu Ala Ser Leu Asp Gly Ser Arg Glu Tyr Val
            180                 185                 190

Asn Val Ser Gln Glu Leu His Pro Gly Ala Ala Lys Thr Glu Pro Ala
        195                 200                 205

Ala Leu Ser Ser Gln Glu Ala Glu Glu Val Glu Glu Gly Ala Pro
210                 215                 220

Asp Tyr Glu Asn Leu Gln Glu Leu Asn
225                 230

<210> SEQ ID NO 5
<211> LENGTH: 242
<212> TYPE: PRT
<213> ORGANISM: Mus musculus

<400> SEQUENCE: 5

Met Glu Ala Asp Ala Leu Ser Pro Val Gly Leu Gly Leu Leu Leu Leu
1               5                   10                  15

Pro Phe Leu Val Thr Leu Leu Ala Ala Leu Cys Val Arg Cys Arg Glu
                20                  25                  30

Leu Pro Val Ser Tyr Asp Ser Thr Ser Thr Glu Ser Leu Tyr Pro Arg
            35                  40                  45

Ser Ile Leu Ile Lys Pro Pro Gln Ile Thr Val Pro Arg Thr Pro Ala
50                  55                  60

Val Ser Tyr Pro Leu Val Thr Ser Phe Pro Pro Leu Arg Gln Pro Asp
65                  70                  75                  80

Leu Leu Pro Ile Pro Arg Ser Pro Gln Pro Leu Gly Gly Ser His Arg
                85                  90                  95

Met Pro Ser Ser Gln Gln Asn Ser Asp Asp Ala Asn Ser Val Ala Ser
            100                 105                 110

Tyr Glu Asn Gln Glu Pro Ala Cys Lys Asn Val Asp Ala Asp Glu Asp
        115                 120                 125

```
Glu Asp Asp Tyr Pro Asn Gly Tyr Leu Val Val Leu Pro Asp Ser Ser
    130                 135                 140
Pro Ala Ala Val Pro Val Val Ser Ser Ala Pro Val Pro Ser Asn Pro
145                 150                 155                 160
Asp Leu Gly Asp Ser Ala Phe Ser Val Glu Ser Cys Glu Asp Tyr Val
                165                 170                 175
Asn Val Pro Glu Ser Glu Glu Ser Ala Glu Ala Ser Leu Asp Gly Ser
            180                 185                 190
Arg Glu Tyr Val Asn Val Ser Pro Glu Gln Gln Pro Val Thr Arg Ala
        195                 200                 205
Glu Leu Ala Ser Val Asn Ser Gln Glu Val Glu Asp Glu Gly Glu Glu
    210                 215                 220
Glu Gly Val Asp Gly Glu Glu Ala Pro Asp Tyr Glu Asn Leu Gln Glu
225                 230                 235                 240
Leu Asn

<210> SEQ ID NO 6
<211> LENGTH: 2454
<212> TYPE: DNA
<213> ORGANISM: Homo sapiens

<400> SEQUENCE: 6
ggaataggtt agtttcagac aagcctgctt gccggagctc agcagacacc aggccttccg      60
ggcaggcctg gcccaccgtg ggcctcgag ctgctgctgg gcattcaga accggctctc      120 cattggcatt gggaccagag accccgcaag tggcctgttt gcctggacat ccacctgtac      180
gtccccaggt ttcgggaggc caggggcga tgccagaccc cgcggcgcac ctgcccttct      240
tctacggcag catctcgcgt gccgaggccg aggagcacct gaagctggcg gcatggcgg      300 acgggctctt cctgctgcgc cagtgcctgc gctcgctggg cggctatgtg ctgtcgctcg      360
tgcacgatgt gcgcttccac cactttccca tcgagcgcca gctcaacggc acctacgcca      420
ttgccggcgg caaagcgcac tgtggaccgg cagagctctg cgagttctac tcgcgcgacc      480
ccgacgggct gccctgcaac ctgcgcaagc cgtgcaaccg gccgtcgggc ctcgagccgc      540
agccgggggt cttcgactgc ctgcgagacg ccatggtgcg tgactacgtg cgccagacgt      600
ggaagctgga gggcgaggcc ctggagcagg ccatcatcag ccaggccccg caggtggaga      660
agctcattgc tacgacggcc cacgagcgga tgccctggta ccacagcagc ctgacgcgtg      720
aggaggccga gcgcaaactt tactctgggg cgcagaccga cggcaagttc ctgctgaggc      780
cgcggaagga gcagggcaca tacgccctgt ccctcatcta tgggaagacg gtgtaccact      840
acctcatcag ccaagacaag gcgggcaagt actgcattcc cgagggcacc aagtttgaca      900
cgctctggca gctggtggag tatctgaagc tgaaggcgga cgggctcatc tactgcctga      960
aggaggcctg ccccaacagc agtgccagca acgcctcagg gctgctgct cccacactcc     1020 cagcccaccc atccacgttg actcatcctc agagacgaat cgacaccctc aactcagatg     1080
gatacacccc tgagccagca cgcataacgt ccccagacaa accgcggccg atgcccatgg     1140
acacgagcgt gtatgagagc ccctacagcg acccagagga gctcaaggac aagaagctct     1200
tcctgaagcg cgataacctc tcatagctg acattgaact ggctgcggc aactttggct     1260 cagtgcgcca gggcgtgtac cgcatgcgca agaagcagat cgacgtggcc atcaaggtgc     1320
tgaagcaggg cacggagaag gcagacacgg aagagatgat gcgcgaggcg cagatcatgc     1380
accagctgga caaccccta atcgtgcggc tcattggcgt ctgccaggcc gaggccctca     1440
```

-continued

```
tgctggtcat ggagatggct gggggcgggc cgctgcacaa gttcctggtc ggcaagaggg    1500
aggagatccc tgtgagcaat gtggccgagc tgctgcacca ggtgtccatg gggatgaagt    1560
acctggagga gaagaacttt gtgcaccgtg acctggcggc ccgcaacgtc ctgctggtta    1620
accggcacta cgccaagatc agcgactttg gcctctccaa agcactgggt gccgacgaca    1680
gctactacac tgcccgctca gcagggaagt ggccgctcaa gtggtacgca cccgaatgca    1740
tcaacttccg caagttctcc agccgcagcg atgtctggag ctatggggtc accatgtggg    1800
aggccttgtc ctacggccag aagccctaca agaagatgaa agggccggag gtcatggcct    1860
tcatcgagca gggcaagcgg atggagtgcc caccagagtg tccacccgaa ctgtacgcac    1920
tcatgagtga ctgctggatc tacaagtggg aggatcgccc cgacttcctg accgtggagc    1980
agcgcatgcg agcctgttac tacagcctgg ccagcaaggt ggaagggccc ccaggcagca    2040
cacagaaggc tgaggctgcc tgtgcctgag ctcccgctgc ccaggggagc cctccacgcc    2100
ggctcttccc caccctcagc cccaccccag gtcctgcagt ctggctgagc cctgcttggt    2160
tgtctccaca cacagctggg ctgtggtagg gggtgtctca ggccacaccg gccttgcatt    2220
gcctgcctgg ccccctgtcc tctctggctg gggagcaggg aggtccggga gggtgcggct    2280
gtgcagcctg tcctgggctg gtggctcccg gagggccctg agctgagggc attgcttaca    2340
cggatgcctt ccctgggcc ctgacattgg agcctgggca tcctcaggtg gtcaggcgta    2400
gatcaccaga ataaacccag cttccctctt gaaaaaaaaa aaaaaaaaaa aacc          2454
```

<210> SEQ ID NO 7
<211> LENGTH: 617
<212> TYPE: PRT
<213> ORGANISM: Homo sapiens

<400> SEQUENCE: 7

```
Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val Asp Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Gln Phe Tyr Ser Gln Asp Pro Asp Gly Leu Pro Cys
                85                  90                  95

Asn Leu Arg Asn Ala Cys Asn Arg Pro Pro Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Asp Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Gln Gln Thr Asp Gly Lys Phe Leu Leu Arg Pro Arg
            180                 185                 190

Lys Glu Gln Gly Thr Tyr Ala Leu Ser Leu Val Tyr Gly Lys Thr Val
        195                 200                 205
```

```
Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Arg Leu Lys Glu Val Cys Pro Asn
                245                 250                 255

Ser Ser Ala Ser Ala Ala Val Ala Ala Pro Thr Leu Pro Ala His Pro
            260                 265                 270

Ser Thr Phe Thr Gln Pro Gln Arg Arg Val Asp Thr Leu Asn Ser Asp
        275                 280                 285

Gly Tyr Thr Pro Glu Pro Ala Arg Leu Ala Ser Ser Thr Asp Lys Pro
    290                 295                 300

Arg Pro Met Pro Met Asp Thr Ser Val Tyr Glu Ser Pro Tyr Ser Asp
305                 310                 315                 320

Pro Glu Glu Leu Lys Asp Lys Lys Leu Phe Leu Lys Arg Glu Asn Leu
                325                 330                 335

Leu Val Ala Asp Ile Glu Leu Gly Cys Gly Asn Phe Gly Ser Val Arg
            340                 345                 350

Gln Gly Val Tyr Arg Met Arg Lys Lys Gln Ile Asp Val Ala Ile Lys
        355                 360                 365

Val Leu Lys Gln Gly Thr Glu Lys Ala Asp Lys Asp Glu Met Met Arg
370                 375                 380

Glu Ala Gln Ile Met His Gln Leu Asp Asn Pro Tyr Ile Val Arg Leu
385                 390                 395                 400

Ile Gly Val Cys Gln Ala Glu Ala Leu Met Leu Val Met Glu Met Ala
                405                 410                 415

Gly Gly Gly Pro Leu His Lys Phe Leu Gly Lys Lys Glu Ile Pro
            420                 425                 430

Val Ser Asn Val Ala Glu Leu Leu His Gln Val Ala Met Gly Met Lys
        435                 440                 445

Tyr Leu Glu Glu Lys Asn Phe Val His Arg Asp Leu Ala Ala Arg Asn
450                 455                 460

Val Leu Leu Val Asn Arg His Tyr Ala Lys Ile Ser Asp Phe Gly Leu
465                 470                 475                 480

Ser Lys Ala Leu Gly Ala Asp Asp Ser Tyr Tyr Thr Ala Arg Ser Ala
                485                 490                 495

Gly Lys Trp Pro Leu Lys Trp Tyr Ala Pro Glu Cys Ile Asn Phe Arg
            500                 505                 510

Lys Phe Ser Ser Arg Ser Asp Val Trp Ser Tyr Gly Val Thr Met Trp
        515                 520                 525

Glu Ala Phe Ser Tyr Gly Gln Lys Pro Tyr Lys Lys Met Lys Gly Pro
530                 535                 540

Glu Val Leu Asp Phe Ile Lys Gln Gly Lys Arg Met Glu Cys Pro Pro
545                 550                 555                 560

Glu Cys Pro Pro Glu Met Tyr Ala Leu Met Ser Asp Cys Trp Ile Tyr
                565                 570                 575

Lys Trp Glu Asp Arg Pro Asp Phe Leu Thr Val Glu Gln Arg Met Arg
            580                 585                 590

Asn Tyr Tyr Tyr Ser Leu Ala Ser Arg Ala Glu Gly Pro Pro Gln Cys
        595                 600                 605

Glu Gln Val Ala Glu Ala Cys Gly
610                 615
```

<210> SEQ ID NO 8
<211> LENGTH: 2541
<212> TYPE: DNA
<213> ORGANISM: Homo sapiens

<400> SEQUENCE: 8

| | | | | | | |
|---|---|---|---|---|---|---|
| gaggaagagc | cgcgggcccg | gcggctgagg | ccaccccggc | ggcggctgga | gagcgaggag | 60 |
| gagcgggtgg | ccccgcgctg | cgcccgccct | cgcctcacct | ggcgcaggtg | gacacctgcg | 120 |
| caggtgtgtg | ccctccggcc | cctgaagcat | ggccagcagc | ggcatggctg | acagcgccaa | 180 |
| ccacctgccc | ttcttttcg | gcaacatcac | ccgggaggag | gcagaagatt | acctggtcca | 240 |
| gggggggcatg | agtgatgggc | tttatttgct | gcgccagagc | cgcaactacc | tgggtggctt | 300 |
| cgccctgtcc | gtggcccacg | ggaggaaggc | acaccactac | accatcgagc | gggagctgaa | 360 |
| tggcacctac | gccatcgccg | gtggcaggac | ccatgccagc | ccgccgacc | tctgccacta | 420 |
| ccactcccag | gagtctgatg | gcctggtctg | cctcctcaag | aagcccttca | accggcccca | 480 |
| aggggtgcag | cccaagactg | gcccctttga | ggatttgaag | gaaaacctca | tcagggaata | 540 |
| tgtgaagcag | acatggaacc | tgcagggtca | ggctctggag | caggccatca | tcagtcagaa | 600 |
| gcctcagctg | gagaagctga | tcgctaccac | agcccatgaa | aaaatgcctt | ggttccatgg | 660 |
| aaaaatctct | cgggaagaat | ctgagcaaat | tgtcctgata | ggatcaaaga | caaatggaaa | 720 |
| gttcctgatc | cgagccagag | acaacaacgg | ctcctacgcc | ctgtgcctgc | tgcacgaagg | 780 |
| gaaggtgctg | cactatcgca | tcgacaaaga | caagacaggg | aagctctcca | tccccgaggg | 840 |
| aaagaagttc | gacacgctct | ggcagctagt | cgagcattat | tcttataaag | cagatggttt | 900 |
| gttaagagtt | cttactgtcc | catgtcaaaa | aatcggcaca | cagggaaatg | ttaattttgg | 960 |
| aggccgtcca | caacttccag | gttcccatcc | tgcgtcctcc | cctgcccaag | ggaaccggca | 1020 |
| agagagtact | gtgtcattca | atccgtatga | gccagaactt | gcaccctggg | ctgcagacaa | 1080 |
| aggcccccag | agagaagccc | tacccatgga | cacagaggtg | tacgagagcc | cctacgcgga | 1140 |
| ccccgaggag | atcaggccca | aggaggttta | cctggaccga | aagctgctga | cgctggaaga | 1200 |
| caaagaactg | ggctctggta | attttggaac | tgtgaaaaag | ggctactacc | aaatgaaaaa | 1260 |
| agttgtgaaa | accgtggctg | tgaaaatact | gaaaaacgag | gccaatgacc | ccgctcttaa | 1320 |
| agatgagtta | ttagcagaag | caaatgtcat | gcagcagctg | gacaacccgt | acatcgtgcg | 1380 |
| gatgatcggg | atatgcgagg | ccgagtcctg | gatgctggtt | atggagatgg | cagaacttgg | 1440 |
| tccccctcaat | aagtatttgc | agcagaacag | acatgtcaag | gataagaaca | tcatagaact | 1500 |
| ggttcatcag | gtttccatgg | gcatgaagta | cttggaggag | agcaattttg | tgcacagaga | 1560 |
| tctggctgca | agaaatgtgt | tgctagttac | ccaacattac | gccaagatca | gtgatttcgg | 1620 |
| actttccaaa | gcactgcgtg | ctgatgaaaa | ctactacaag | gcccagaccc | atggaaagtg | 1680 |
| gcctgtcaag | tggtacgctc | cggaatgcat | caactactac | aagttctcca | gcaaaagcga | 1740 |
| tgtctggagc | tttggagtgt | tgatgtggga | agcattctcc | tatgggcaga | agccatatcg | 1800 |
| agggatgaaa | ggaagtgaag | tcaccgctat | gttagagaaa | ggagagcgga | tggggtgccc | 1860 |
| tgcagggtgt | ccaagagaga | tgtacgatct | catgaatctg | tgctggacat | acgatgtgga | 1920 |
| aaacaggccc | ggattcgcag | cagtggaact | gcggctgcgc | aattactact | atgacgtggt | 1980 |
| gaactaaccg | ctcccgcacc | tgtcggtggc | tgcctttgat | cacaggagca | atcacaggaa | 2040 |
| aatgtatcca | gaggaattga | ttgtcagcca | cctccctctg | ccagtcggga | gagccaggct | 2100 |
| tggatgaac | atgcccacaa | cttgtcaccc | aaagcctgtc | ccaggactca | ccctccacaa | 2160 |
| agcaaaggca | gtcccgggag | aaaagacgga | tgcaggatc | caagggggcta | gctggatttg | 2220 |

```
tttgttttct tgtctgtgtg attttcatac aggttatttt tacgatctgt ttccaaatcc    2280
ctttcatgtc tttccacttc tctgggtccc ggggtgcatt tgttactcat cgggcccagg    2340
gacattgcag agtggcctag agcactctca ccccaagcgg cctttccaa atgcccaagg     2400 atgccttagc atgtgactcc tgaagggaag gcaaaggcag aggaatttgg ctgcttctac    2460
ggccatgaga ctgatccctg gccactgaaa agctttcctg acaataaaaa tgttttgagg    2520
ctttaaaaag aaaaaaaaaa a                                              2541

<210> SEQ ID NO 9
<211> LENGTH: 612
<212> TYPE: PRT
<213> ORGANISM: Homo sapiens

<400> SEQUENCE: 9

Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
                20                  25                  30

Gly Met Ser Asp Gly Leu Tyr Leu Leu Arg Gln Ser Arg Asn Tyr Leu
            35                  40                  45

Gly Gly Phe Ala Leu Ser Val Ala His Gly Arg Lys Ala His His Tyr
        50                  55                  60

Thr Ile Glu Arg Glu Leu Asn Gly Thr Tyr Ala Ile Ala Gly Gly Arg
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
        115                 120                 125

Arg Glu Tyr Val Lys Gln Thr Trp Asn Leu Gln Gly Gln Ala Leu Glu
    130                 135                 140

Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
        195                 200                 205

His Glu Gly Lys Val Leu His Tyr Arg Ile Asp Lys Asp Lys Thr Gly
    210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255

Val Pro Cys Gln Lys Ile Gly Thr Gln Gly Asn Val Asn Phe Gly Gly
            260                 265                 270

Arg Pro Gln Leu Pro Gly Ser His Pro Ala Ser Pro Ala Gln Gly
        275                 280                 285

Asn Arg Gln Glu Ser Thr Val Ser Phe Asn Pro Tyr Glu Pro Glu Leu
    290                 295                 300

Ala Pro Trp Ala Ala Asp Lys Gly Pro Gln Arg Glu Ala Leu Pro Met
305                 310                 315                 320
```

Asp Thr Glu Val Tyr Glu Ser Pro Tyr Ala Asp Pro Glu Glu Ile Arg
                325                 330                 335

Pro Lys Glu Val Tyr Leu Asp Arg Lys Leu Leu Thr Leu Glu Asp Lys
            340                 345                 350

Glu Leu Gly Ser Gly Asn Phe Gly Thr Val Lys Lys Gly Tyr Tyr Gln
        355                 360                 365

Met Lys Lys Val Lys Thr Val Ala Val Lys Ile Leu Lys Asn Glu
    370                 375                 380

Ala Asn Asp Pro Ala Leu Lys Asp Glu Leu Leu Ala Glu Ala Asn Val
385                 390                 395                 400

Met Gln Gln Leu Asp Asn Pro Tyr Ile Val Arg Met Ile Gly Ile Cys
                405                 410                 415

Glu Ala Glu Ser Trp Met Leu Val Met Glu Met Ala Glu Leu Gly Pro
            420                 425                 430

Leu Asn Lys Tyr Leu Gln Gln Asn Arg His Val Lys Asp Lys Asn Ile
        435                 440                 445

Ile Glu Leu Val His Gln Val Ser Met Gly Met Lys Tyr Leu Glu Glu
    450                 455                 460

Ser Asn Phe Val His Arg Asp Leu Ala Ala Arg Asn Val Leu Leu Val
465                 470                 475                 480

Thr Gln His Tyr Ala Lys Ile Ser Asp Phe Gly Leu Ser Lys Ala Leu
                485                 490                 495

Arg Ala Asp Glu Asn Tyr Tyr Lys Ala Gln Thr His Gly Lys Trp Pro
            500                 505                 510

Val Lys Trp Tyr Ala Pro Glu Cys Ile Asn Tyr Tyr Lys Phe Ser Ser
        515                 520                 525

Lys Ser Asp Val Trp Ser Phe Gly Val Leu Met Trp Glu Ala Phe Ser
    530                 535                 540

Tyr Gly Gln Lys Pro Tyr Arg Gly Met Lys Gly Ser Glu Val Thr Ala
545                 550                 555                 560

Met Leu Glu Lys Gly Glu Arg Met Gly Cys Pro Ala Gly Cys Pro Arg
                565                 570                 575

Glu Met Tyr Asp Leu Met Asn Leu Cys Trp Thr Tyr Asp Val Glu Asn
            580                 585                 590

Arg Pro Gly Phe Ala Ala Val Glu Leu Arg Leu Arg Asn Tyr Tyr Tyr
        595                 600                 605

Asp Val Val Asn
    610

<210> SEQ ID NO 10
<211> LENGTH: 1109
<212> TYPE: DNA
<213> ORGANISM: Homo sapiens

<400> SEQUENCE: 10
gccagtgaat tcgggggctc agccctcctc cctcccttcc ccctgcttca ggctgctgag    60
cactgagcag cgctcagaat ggaagccatc gccaaatatg acttcaaagc tactgcagac   120
gacgagctga gcttcaaaag gggggacatc ctcaaggttt tgaacgaaga atgtgatcag   180
aactggtaca aggcagagct taatggaaaa gacggcttca ttcccaagaa ctacatagaa   240
atgaaaccac atccgtggtt ttttggcaaa atccccagag ccaaggcaga agaaatgctt   300
agcaaacagc ggcacgatgg ggcctttctt atccgagaga gtgagagcgc tcctggggac   360
ttctccctct ctgtcaagtt tggaaacgat gtgcagcact tcaaggtgct ccgagatgga   420

```
gccgggaagt acttcctctg ggtggtgaag ttcaattctt tgaatgagct ggtggattat    480
cacagatcta catctgtctc cagaaaccag cagatattcc tgcgggacat agaacaggtg    540
ccacagcagc cgacatacgt ccaggccctc tttgactttg atccccagga ggatggagag    600
ctgggcttcc gccggggaga ttttatccat gtcatggata actcagaccc caactggtgg    660
aaaggagctt gccacgggca gaccggcatg tttccccgca attatgtcac ccccgtgaac    720
cggaacgtct aagagtcaag aagcaattat ttaaagaaag tgaaaatgt aaacacata    780 caaaagaatt aaacccacaa gctgcctctg acagcagcct gtgagggagt gcagaacacc    840
tggccgggtc accctgtgac cctctcactt tggttggaac tttaggggt gggaggggc    900 gttggattta aaaatgccaa aacttaccta taaattaaga gagtttttta ttacaaattt    960
tcactgctgc cctctcttcc cctcctttgt ctttttttc atccttttt ctcttctgtc    1020 catcagtgca tgacgtttaa ggccacgtat agtcctagct gacgccaata ataaaaaaca    1080
agaaaccaaa aaaaaaaaac ccgaattca                                     1109
```

<210> SEQ ID NO 11
<211> LENGTH: 217
<212> TYPE: PRT
<213> ORGANISM: Homo sapiens

<400> SEQUENCE: 11

```
Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Lys Pro His Pro Trp Phe Phe Gly Lys
    50                  55                  60

Ile Pro Arg Ala Lys Ala Glu Glu Met Leu Ser Lys Gln Arg His Asp
65                  70                  75                  80

Gly Ala Phe Leu Ile Arg Glu Ser Glu Ser Ala Pro Gly Asp Phe Ser
                85                  90                  95

Leu Ser Val Lys Phe Gly Asn Asp Val Gln His Phe Lys Val Leu Arg
            100                 105                 110

Asp Gly Ala Gly Lys Tyr Phe Leu Trp Val Val Lys Phe Asn Ser Leu
        115                 120                 125

Asn Glu Leu Val Asp Tyr His Arg Ser Thr Ser Val Ser Arg Asn Gln
    130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175

Phe Arg Arg Gly Asp Phe Ile His Val Met Asp Asn Ser Asp Pro Asn
            180                 185                 190

Trp Trp Lys Gly Ala Cys His Gly Gln Thr Gly Met Phe Pro Arg Asn
        195                 200                 205

Tyr Val Thr Pro Val Asn Arg Asn Val
    210                 215
```

<210> SEQ ID NO 12
<211> LENGTH: 2757
<212> TYPE: DNA
<213> ORGANISM: Homo sapiens

<400> SEQUENCE: 12

```
ctaggctttt gcaaaaagct tcacgctgcc gcaagcactc agggcgcaag ggctgctaaa     60
ggaagcggaa cacgtagaaa gccagtccgc agaaacggtg ctgacccecgg atgaatgtca    120
gctactgggc tatctggaca agggaaaacg caagcgcaaa gagaaagcag ttcctgtgcc    180
ttaagaacat tagaaccttc ctgtccacct gctgtgagaa gttcggcctc aagcggagcg    240
agctcttcga agcctttgac ctcttcgatg tgcaggattt tggcaaggtc atctacaccc    300
tgtctgctct gtcctggacc ccgatcgccc agaacagggg gatcatgccc ttccccaccg    360
aggaggagag tgtaggtgat gaagacatct acagtggcct gtccgaccag atcgacgaca    420
cggtggagga ggatgaggac ctgtatgact gcgtggagaa tgaggaggcg gaaggcgacg    480
agatctatga ggacctcatg cgctcggagc ccgtgtccat gccgcccaag atgacagagt    540
atgacaagcg ctgctgctgc tgcgggaga tccagcagac ggaggagaag tacactgaca    600
cgctgggctc catccagcag catttcttga agccectgca acggttcctg aaacctcaag    660
acattgagat catctttatc aacattgagg acctgcttcg tgttcatact cacttcctaa    720
aggagatgaa ggaagccctg gcaccectg gcgcaccgaa tctctaccag gtcttcatca    780
aatacaagga gaggttcctc gtctatggcc gctactgcag ccaggtggag tcagccagca    840
acacctgga ccgtgtggcc gcagcccggg aggacgtgca gatgaagctg gaggaatgtt    900
ctcagagagc caacaacggg aggttcactg cgcgacctgc tgatggtgcc tatgcagcga    960
gttctcaaat atcacctcct tctccaggag ctggtgaaac acacgcagga ggcgatggag   1020
caaggaaact gcggctggcc ctggatgcca tgagggacct ggctcagtgc gtgaacgagg   1080
tcaagcgaga caacgagaca ctgcgacaga tcaccaattt ccagctgtcc attgagaacc   1140
tggaccagtc tctggctcac tatggccggc ccaagatcga cggggaactc aagatcacct   1200
cggtggaacg gcgctccaag atggacaggt atgccttcct gctcgacaaa gctctactca   1260
tctgtaagcg caggggagac tcctatgacc tcaaggactt tgtaaacctg cacagcttcc   1320
aggttcggga tgactcttca ggagaccgag acaacaagaa gtggagccac atgttcctcc   1380
tgatcgagga ccaaggtgcc cagggctatg agctgttctt caagacaaga gaattgaaga   1440
agaagtggat ggagcagttt gagatggcca tctccaacat ctatccggag aatgccaccg   1500
ccaacgggca tgacttccag atgttctcct ttgaggagac cacatcctgc aaggcctgtc   1560
agatgctgct tagaggtacc ttctatcagg ctaccgctg ccatcggtgc gggcatctg    1620
cacacaagga gtgtctgggg agggtccctc catgtggccg acatgggcaa gatttcccag   1680
gaactatgaa gaaggacaaa ctacatcgca gggctcagga caaaaagagg aatgagctgg   1740
gtctgcccaa gatggaggtg tttcaggaat actacgggct tcctccaccc cctggagcca   1800
ttggaccctt tctacggctc aaccctggag acattgtgga gctcacgaag gctgaggctg   1860
aacagaactg gtgggagggc agaaatacat ctactaatga aattggctgg tttccttgta   1920
acagggtgaa gccctatgtc catggccctc ctcaggacct gtctgttcat ctctggtacg   1980
caggccccat ggagcgggca ggggcagaga gcatcctggc caaccgctcg gacgggactt   2040
tcttggtgcg gcagagggtg aaggatgcag cagaatttgc catcagcatt aaatataacg   2100
tcgaggtcaa gcacacggtt aaaatcatga cagcagaagg actgtaccgg atcacagaga   2160
aaaaggcttt ccgggggctt acggagctgg tggagtttta ccagcagaac tctctaaagg   2220
attgcttcaa gtctctggac accaccttgc agttcccctt caaggagcct gaaaagagaa   2280
ccatcagcag gccagcagtg ggaagcacaa agtatttggg cacagccaaa gcccgctatg   2340
```

-continued

```
acttctgcgc ccgtgaccgt tcagagctgt cgctcaagga gggtgacatc atcaagatcc    2400
ttaacaagaa gggacagcaa ggctggtggc gaggggagat ctatggccgg gttggctggt    2460
tccctgccaa ctacgtggag gaagattatt ctgaatactg ctgagccctg gtgccttggc    2520
agagagacga gaaactccag gctctgagcc cggcgtggcg aggcagcgga ccaggggctg    2580
tgacagctcc ggcgggtgga gactttggga tggactggag gaggccagcg tccagctggc    2640
ggtgctcccg ggatgtgccc tgacatggtt aatttataac accccgattt tcctcttggg    2700
tcccctcaag cagacggggg ctcaagggggg ttacatttaa taaaaggatg aagatgg      2757
```

<210> SEQ ID NO 13
<211> LENGTH: 797
<212> TYPE: PRT
<213> ORGANISM: Homo sapiens

<400> SEQUENCE: 13

```
Met Asn Val Ser Tyr Trp Ala Ile Trp Thr Arg Glu Asn Ala Ser Ala
1               5                   10                  15

Lys Arg Lys Gln Phe Leu Cys Leu Lys Asn Ile Arg Thr Phe Leu Ser
                20                  25                  30

Thr Cys Cys Glu Lys Phe Gly Leu Lys Arg Ser Glu Leu Phe Glu Ala
            35                  40                  45

Phe Asp Leu Phe Asp Val Gln Asp Phe Gly Lys Val Ile Tyr Thr Leu
        50                  55                  60

Ser Ala Leu Ser Trp Thr Pro Ile Ala Gln Asn Arg Gly Ile Met Pro
65                  70                  75                  80

Phe Pro Thr Glu Glu Ser Val Gly Asp Glu Asp Ile Tyr Ser Gly
                85                  90                  95

Leu Ser Asp Gln Ile Asp Asp Thr Val Glu Glu Asp Glu Asp Leu Tyr
            100                 105                 110

Asp Cys Val Glu Asn Glu Glu Ala Glu Gly Asp Glu Ile Tyr Glu Asp
        115                 120                 125

Leu Met Arg Ser Glu Pro Val Ser Met Pro Lys Met Thr Glu Tyr
130                 135                 140

Asp Lys Arg Cys Cys Cys Leu Arg Glu Ile Gln Gln Thr Glu Glu Lys
145                 150                 155                 160

Tyr Thr Asp Thr Leu Gly Ser Ile Gln Gln His Phe Leu Lys Pro Leu
                165                 170                 175

Gln Arg Phe Leu Lys Pro Gln Asp Ile Glu Ile Ile Phe Ile Asn Ile
            180                 185                 190

Glu Asp Leu Leu Arg Val His Thr His Phe Leu Lys Glu Met Lys Glu
        195                 200                 205

Ala Leu Gly Thr Pro Gly Ala Pro Asn Leu Tyr Gln Val Phe Ile Lys
    210                 215                 220

Tyr Lys Glu Arg Phe Leu Val Tyr Gly Arg Tyr Cys Ser Gln Val Glu
225                 230                 235                 240

Ser Ala Ser Lys His Leu Asp Arg Val Ala Ala Arg Glu Asp Val
                245                 250                 255

Gln Met Lys Leu Glu Glu Cys Ser Gln Arg Ala Asn Asn Gly Arg Phe
            260                 265                 270

Thr Ala Arg Pro Ala Asp Gly Ala Tyr Ala Ala Ser Ser Gln Ile Ser
        275                 280                 285

Pro Pro Ser Pro Gly Ala Gly Glu Thr His Ala Gly Gly Asp Gly Ala
    290                 295                 300

Arg Lys Leu Arg Leu Ala Leu Asp Ala Met Arg Asp Leu Ala Gln Cys
```

-continued

```
            305                 310                 315                 320
Val Asn Glu Val Lys Arg Asp Asn Glu Thr Leu Arg Gln Ile Thr Asn
                325                 330                 335
Phe Gln Leu Ser Ile Glu Asn Leu Asp Gln Ser Leu Ala His Tyr Gly
                340                 345                 350
Arg Pro Lys Ile Asp Gly Leu Lys Ile Thr Ser Val Glu Arg Arg
                355                 360                 365
Ser Lys Met Asp Arg Tyr Ala Phe Leu Leu Asp Lys Ala Leu Leu Ile
                370                 375                 380
Cys Lys Arg Arg Gly Asp Ser Tyr Asp Leu Lys Asp Phe Val Asn Leu
385                 390                 395                 400
His Ser Phe Gln Val Arg Asp Asp Ser Gly Asp Arg Asp Asn Lys
                405                 410                 415
Lys Trp Ser His Met Phe Leu Leu Ile Glu Asp Gln Gly Ala Gln Gly
                420                 425                 430
Tyr Glu Leu Phe Phe Lys Thr Arg Glu Leu Lys Lys Lys Trp Met Glu
                435                 440                 445
Gln Phe Glu Met Ala Ile Ser Asn Ile Tyr Pro Glu Asn Ala Thr Ala
                450                 455                 460
Asn Gly His Asp Phe Gln Met Phe Ser Phe Glu Thr Thr Ser Cys
465                 470                 475                 480
Lys Ala Cys Gln Met Leu Leu Arg Gly Thr Phe Tyr Gln Gly Tyr Arg
                485                 490                 495
Cys His Arg Cys Arg Ala Ser Ala His Lys Glu Cys Leu Gly Arg Val
                500                 505                 510
Pro Pro Cys Gly Arg His Gly Gln Asp Phe Pro Gly Thr Met Lys Lys
                515                 520                 525
Asp Lys Leu His Arg Arg Ala Gln Asp Lys Lys Arg Asn Glu Leu Gly
                530                 535                 540
Leu Pro Lys Met Glu Val Phe Gln Glu Tyr Tyr Gly Leu Pro Pro Pro
545                 550                 555                 560
Pro Gly Ala Ile Gly Pro Phe Leu Arg Leu Asn Pro Gly Asp Ile Val
                565                 570                 575
Glu Leu Thr Lys Ala Glu Ala Glu Gln Asn Trp Trp Glu Gly Arg Asn
                580                 585                 590
Thr Ser Thr Asn Glu Ile Gly Trp Phe Pro Cys Asn Arg Val Lys Pro
                595                 600                 605
Tyr Val His Gly Pro Pro Gln Asp Leu Ser Val His Leu Trp Tyr Ala
                610                 615                 620
Gly Pro Met Glu Arg Ala Gly Ala Glu Ser Ile Leu Ala Asn Arg Ser
625                 630                 635                 640
Asp Gly Thr Phe Leu Val Arg Gln Arg Val Lys Asp Ala Ala Glu Phe
                645                 650                 655
Ala Ile Ser Ile Lys Tyr Asn Val Glu Val Lys His Thr Val Lys Ile
                660                 665                 670
Met Thr Ala Glu Gly Leu Tyr Arg Ile Thr Glu Lys Lys Ala Phe Arg
                675                 680                 685
Gly Leu Thr Glu Leu Val Glu Phe Tyr Gln Gln Asn Ser Leu Lys Asp
                690                 695                 700
Cys Phe Lys Ser Leu Asp Thr Thr Leu Gln Phe Pro Phe Lys Glu Pro
705                 710                 715                 720
Glu Lys Arg Thr Ile Ser Arg Pro Ala Val Gly Ser Thr Lys Tyr Phe
                725                 730                 735
```

```
Gly Thr Ala Lys Ala Arg Tyr Asp Phe Cys Ala Arg Asp Arg Ser Glu
            740                 745                 750

Leu Ser Leu Lys Glu Gly Asp Ile Lys Ile Leu Asn Lys Lys Gly
        755                 760                 765

Gln Gln Gly Trp Trp Arg Gly Glu Ile Tyr Gly Arg Val Gly Trp Phe
    770                 775                 780

Pro Ala Asn Tyr Val Glu Glu Asp Tyr Ser Glu Tyr Cys
785                 790                 795

<210> SEQ ID NO 14
<211> LENGTH: 3090
<212> TYPE: DNA
<213> ORGANISM: Homo sapiens

<400> SEQUENCE: 14
gaattccggg cccggatagc cggcggcggc ggcggcggcg gcggcggcgg cggccgggag      60
aggcccctcc ttcacgccct gcttctctcc ctcgctcgca gtcgagccga gccggcggac     120
ccgcctgggc tccgaccctg cccaggccat ggccggcaac gtgaagaaga gctctggggc     180
cgggggcggc acgggctccg ggggctcggg ttcgggtggc ctgattgggc tcatgaagga     240
cgccttccag ccgcaccacc accaccacca ccacctcagc ccccaccgc cggggacggt     300 ggacaagaag atggtggaga gtgctgaa gctcatggac aaggtggtgc ggttgtgtca     360
gaacccaaag ctggcgctaa agaatagccc accttatatc ttagacctgc taccagatac     420
ctaccagcat ctccgtacta tcttgtcaag atatgagggg aagatggaga cacttggaga     480
aaatgagtat tttagggtgt ttatggagaa tttgatgaag aaaactaagc aaaccataag     540
cctcttcaag gagggaaaag aagaatgta tgaggaaat tctcagccta ggcgaaacct     600
aaccaaactg tccctcatct tcagccacat gctggcagaa ctaaaaggaa tctttccaag     660
tggactcttt cagggagaca catttcggat tactaaagca gatgctgcgg aatttttggag     720 aaaagctttt ggggaaaaga caatagtccc ttggaagagc tttcgacagg ctctacatga     780
agtgcatccc atcagttctg ggctggaggc catggctctg aaatccacta ttgatctgac     840
ctgcaatgat tatatttcgg tttttgaatt tgacatcttt acccgactct ttcagccctg     900
gtcctctttg ctcaggaatt ggaacagcct tgctgtaact catcctggct acatggcttt     960
tttgacgtat gacgaagtga aagctcggct ccagaaattc attcacaaac tggcagttta    1020
tatcttccgg ctgagctgta ctcgtctggg tcagtgggct attgggtatg ttactgctga    1080
tgggaacatt ctccagacaa tccctcacaa taaacctctc ttccaagcac tgattgatgg    1140
cttcagggaa ggcttctatt tgtttcctga tggacgaaat cagaatcctg atctgactgg    1200
cttatgtgaa ccaactcccc aagaccatat caaagtgacc caggaacaat atgaattata    1260
ctgtgagatg ggctccacat tccaactatg taaaatatgt gctgaaaatg ataaggatgt    1320
aaagattgag ccctgtggac acctcatgtg cacatcctgt cttacatcct ggcaggaatc    1380
agaaggtcag ggctgtcctt tctgccgatg tgaaattaaa ggtactgaac ccatcgtggt    1440
agatccgttt gatcctagag ggagtggcag cctgttgagg caaggagcag agggagctcc    1500 ctcccccaaat tatgatgatg atgatgatga acagctgat gatactctct tcatgatgaa    1560
ggaattggct ggtgccaagg tggaacggcc gccttctcca ttctccatgg ccccacaagc    1620
ttcccttccc ccggtgccac cacgacttga ccttctgccg cagcgagtat gtgttccctc    1680
aagtgcttct gctcttggaa ctgcttctaa ggctgcttct ggctcccttc ataaagacaa    1740
accattgcca gtacctccca cacttcgaga tcttccacca ccaccgcctc cagaccggcc    1800
```

```
atattctgtt ggagcagaat cccgacctca aagacgcccc ttgccttgta caccaggcga   1860
ctgtccctcc agagacaaac tgcccccgt cccctctagc cgccttggag actcatggct   1920
gccccggcca atccccaaag taccagtatc tgccccaagt tccagtgatc cctggacagg   1980
aagagaatta accaaccggc actcacttcc attttcattg ccctcacaaa tggagcccag   2040
accagatgtg cctaggctcg gaagcacgtt cagtctggat acctccatga gtatgaatag   2100
cagcccatta gtaggtccag agtgtgacca ccccaaaatc aaaccttcct catctgccaa   2160
tgccatttat tctctggctg ccagacctct tcctgtgcca aaactgccac tggggagca    2220 atgtgagggt gaagaggaca cagagtacat gactccctct tccaggcctc tacggccttt   2280
ggatacatcc agagttcac gagcatgtga ttgcgaccag cagattgata gctgtacgta    2340
tgaagcaatg tataatattc agtcccaggc gccatctatc accgagagca gcacctttgg   2400
tgaagggaat ttggccgcag cccatgccaa cactggtccc gaggagtcag aaaatgagga   2460
tgatgggtat gatgtcccaa agccaccgt gccggccgtg ctggccccgcc gaactctctc   2520 agatatctct aatgccagct cctccttgg ctggttgtct ctggatggtg atcctacaac    2580
aaatgtcact gaaggttccc aagttcccga gaggcctcca aaaccattcc cgcggagaat   2640
caactctgaa cggaaagctg cagctgtca gcaaggtagt ggtcctgccg cctctgctgc   2700
caccgcctca cctcagctct ccagtgagat cgagaacctc atgagtcagg gtactcctta  2760
ccaggacatc agaaagcttt tggtcattgc ccagaacaac atcgagatgg ccaaaaacat  2820
cctccgggaa tttgtttcca tttcttctcc tgcccatgta gctacctagc acccatctc   2880 cctgctgcag gtttagagga ccagtgagtt gggagttat actcaagtgg cacctagaag   2940
ggcaggagtt cctttggtga cttcacagtg aagtcttgcc ctctctgtgg gatatcacat  3000
cagtggttcc aagatttcaa agtggtgaaa tgaaaatgga gcagctagta tgttttatta  3060
ttttatgggt cttgagtgca tttgaaggtg                                    3090
```

<210> SEQ ID NO 15
<211> LENGTH: 897
<212> TYPE: PRT
<213> ORGANISM: Homo sapiens

<400> SEQUENCE: 15

```
Met Ala Gly Asn Val Lys Lys Ser Ser Gly Ala Gly Gly Gly Ser
1               5                   10                  15

Gly Gly Ser Gly Ala Gly Gly Leu Ile Gly His Met Lys Asp Ala Phe
            20                  25                  30

Gly Pro His His His His His His Leu Ser Pro His Pro Pro Cys Thr
        35                  40                  45

Val Asp Lys Lys Met Val Glu Lys Cys Trp Lys Leu Met Asp Lys Val
    50                  55                  60

Val Arg Leu Cys Gln Asn Pro Asn Val Ala Leu Lys Asn Ser Pro Pro
65                  70                  75                  80

Tyr Ile Leu Asp Leu Leu Pro Asp Thr Tyr Gly His Leu Arg Thr Val
                85                  90                  95

Leu Ser Arg Tyr Glu Gly Lys Met Glu Thr Leu Gly Glu Asn Glu Tyr
            100                 105                 110

Phe Arg Val Phe Met Glu Asn Leu Met Lys Lys Thr Lys Gln Thr Ile
        115                 120                 125

Ser Leu Phe Lys Glu Gly Lys Glu Arg Met Tyr Glu Glu Asn Ser Gln
    130                 135                 140

Pro Arg Arg Asn Leu Thr Lys Leu Ser Leu Ile Phe Ser His Met Leu
```

-continued

```
            145                 150                 155                 160
Ala Glu Leu Lys Gly Ile Phe Pro Ser Gly Leu Phe Gln Gly Asp Thr
                165                 170                 175
Phe Arg Ile Thr Lys Ala Asp Ala Glu Phe Trp Arg Lys Ala Phe
                180                 185                 190
Gly Glu Lys Thr Ile Val Pro Trp Lys Ser Phe Arg Gln Ala Leu His
                195                 200                 205
Glu Val His Pro Ile Ser Ser Gly Leu Glu Ala Met Ala Leu Lys Ser
                210                 215                 220
Thr Ile Asp Leu Thr Cys Asn Asp Tyr Ile Ser Val Phe Glu Phe Asp
225                 230                 235                 240
Ile Phe Thr Arg Leu Phe Gln Pro Trp Ser Ser Leu Leu Arg Asn Trp
                245                 250                 255
Asn Ser Leu Ala Val Thr His Pro Gly Tyr Met Ala Phe Leu Thr Tyr
                260                 265                 270
Asp Glu Val Lys Ala Arg Leu Gln Lys Phe Ile His Lys Pro Gly Ser
                275                 280                 285
Tyr Ile Phe Arg Leu Ser Cys Thr Arg Leu Gly Gln Trp Ala Ile Gly
                290                 295                 300
Tyr Val Thr Ala Asp Gly Asn Ile Leu Gln Thr Ile Pro His Asn Lys
305                 310                 315                 320
Pro Leu Phe Gln Ala Leu Ile Asp Gly Phe Arg Glu Gly Phe Tyr Leu
                325                 330                 335
Phe Pro Asp Gly Arg Asn Gln Asn Pro Asp Leu Thr Gly Leu Cys Glu
                340                 345                 350
Pro Thr Pro Gln Asp His Ile Lys Val Thr Gln Ile Cys Ala Glu Asn
                355                 360                 365
Asp Lys Asp Val Lys Ile Glu Pro Cys Gly His Leu Met Cys Thr Ser
                370                 375                 380
Cys Leu Thr Ser Trp Gln Glu Ser Glu Gly Gln Gly Cys Pro Phe Cys
385                 390                 395                 400
Arg Cys Glu Ile Lys Gly Thr Glu Pro Ile Val Val Asp Pro Phe Asp
                405                 410                 415
Pro Arg Gly Ser Gly Ser Leu Leu Arg Gln Gly Ala Glu Gly Ala Pro
                420                 425                 430
Ser Pro Asn Tyr Asp Asp Asp Asp Glu Arg Ala Asp Asp Ser Leu
                435                 440                 445
Phe Met Met Lys Glu Leu Ala Gly Ala Lys Val Glu Arg Pro Ser Ser
450                 455                 460
Pro Phe Ser Met Ala Pro Gln Ala Ser Leu Pro Pro Val Pro Pro Arg
465                 470                 475                 480
Leu Asp Leu Leu Gln Gln Arg Ala Pro Val Pro Ala Ser Thr Ser Val
                485                 490                 495
Leu Gly Thr Ala Ser Lys Ala Ala Ser Gly Ser Leu His Lys Asp Lys
                500                 505                 510
Pro Leu Pro Ile Pro Pro Thr Leu Arg Asp Leu Pro Pro Pro Pro
                515                 520                 525
Pro Asp Arg Pro Tyr Ser Val Gly Ala Glu Thr Arg Pro Gln Arg Arg
                530                 535                 540
Pro Leu Pro Cys Thr Pro Gly Asp Cys Pro Ser Arg Asp Lys Leu Pro
545                 550                 555                 560
Pro Val Pro Ser Ser Arg Pro Gly Asp Ser Trp Leu Ser Arg Thr Ile
                565                 570                 575
```

```
Pro Lys Val Pro Val Ala Thr Pro Asn Pro Gly Asp Pro Trp Asn Gly
            580                 585                 590

Arg Glu Leu Thr Asn Arg His Ser Leu Pro Phe Ser Leu Pro Ser Gln
            595                 600                 605

Met Glu Pro Arg Ala Asp Val Pro Arg Leu Gly Ser Thr Phe Ser Leu
610                 615                 620

Asp Thr Ser Met Thr Met Asn Ser Ser Pro Val Ala Gly Pro Glu Ser
625                 630                 635                 640

Glu His Pro Lys Ile Lys Pro Ser Ser Ala Asn Ala Ile Tyr Ser
                645                 650                 655

Leu Ala Ala Arg Pro Leu Pro Met Pro Lys Leu Pro Pro Gly Glu Gln
            660                 665                 670

Gly Glu Ser Glu Glu Asp Thr Glu Tyr Met Thr Pro Thr Ser Arg Pro
            675                 680                 685

Val Gly Val Gln Lys Pro Glu Pro Lys Arg Pro Leu Glu Ala Thr Gln
            690                 695                 700

Ser Ser Arg Ala Cys Asp Cys Asp Gln Gln Ile Asp Ser Cys Thr Tyr
705                 710                 715                 720

Glu Ala Arg Asn Tyr Thr Ile Gln Ser Gln Ala Leu Ser Val Ala Glu
                725                 730                 735

Asn Ser Ala Ser Gly Glu Gly Asn Leu Ala Thr Ala His Thr Ser Thr
            740                 745                 750

Gly Pro Glu Glu Ser Glu Asn Glu Asp Asp Gly Tyr Asp Val Pro Lys
            755                 760                 765

Pro Pro Val Pro Ala Val Leu Ala Arg Arg Thr Leu Ser Asp Ile Ser
            770                 775                 780

Asn Ala Ser Ser Ser Phe Gly Trp Leu Ser Leu Asp Gly Asp Pro Thr
785                 790                 795                 800

His Phe Asn Glu Gly Ser Gly Val Pro Glu Arg Pro Pro Lys Pro Phe
                805                 810                 815

Pro Arg Arg Ile Asn Ser Glu Arg Lys Ala Ser Ser Tyr Gln Gln Gly
            820                 825                 830

Gly Gly Ala Thr Ala Asn Pro Val Ala Thr Ala Pro Ser Pro Gln Leu
            835                 840                 845

Ser Ser Glu Ile Glu Arg Leu Met Ser Gln Gly Tyr Ser Tyr Gln Asp
850                 855                 860

Ile Gln Lys Ala Leu Val Ile Ala His Asn Asn Ile Glu Met Ala Lys
865                 870                 875                 880

Asn Ile Leu Arg Glu Phe Val Ser Ile Ser Ser Pro Ala His Val Ala
                885                 890                 895

Thr

<210> SEQ ID NO 16
<211> LENGTH: 13
<212> TYPE: PRT
<213> ORGANISM: Homo sapiens

<400> SEQUENCE: 16

Ser Met Glu Gln Lys Leu Ile Ser Glu Glu Asp Leu Asn
1               5                   10

<210> SEQ ID NO 17
<211> LENGTH: 8
<212> TYPE: PRT
<213> ORGANISM: Artificial
<220> FEATURE:
<223> OTHER INFORMATION: Synthetic
```

```
<400> SEQUENCE: 17

Asp Tyr Lys Asp Asp Asp Asp Lys
1               5

<210> SEQ ID NO 18
<211> LENGTH: 24
<212> TYPE: DNA
<213> ORGANISM: Artificial
<220> FEATURE:
<223> OTHER INFORMATION: Synthetic

<400> SEQUENCE: 18
aattcgccgc catggcactg tgtg                                          24

<210> SEQ ID NO 19
<211> LENGTH: 24
<212> TYPE: DNA
<213> ORGANISM: Artificial
<220> FEATURE:
<223> OTHER INFORMATION: Synthetic

<400> SEQUENCE: 19
tgcacacaca gtgccatggc ggcg                                          24

<210> SEQ ID NO 20
<211> LENGTH: 15
<212> TYPE: PRT
<213> ORGANISM: Homo sapiens
<220> FEATURE:
<221> NAME/KEY: X
<222> LOCATION: (1)..(2)
<223> OTHER INFORMATION: x is unassigned
<220> FEATURE:
<221> NAME/KEY: X
<222> LOCATION: (11)..(11)
<223> OTHER INFORMATION: X is unassigned
<220> FEATURE:
<221> NAME/KEY: misc_feature
<222> LOCATION: (12)..(12)
<223> OTHER INFORMATION: Xaa can be any naturally occurring amino acid

<400> SEQUENCE: 20

Xaa Xaa Val Asn Val Ser Gln Glu Leu His Pro Xaa Ala Ala Lys
1               5                   10                  15

<210> SEQ ID NO 21
<211> LENGTH: 16
<212> TYPE: PRT
<213> ORGANISM: Homo sapiens

<400> SEQUENCE: 21

Ser Glu Val Leu Gly Trp Asp Pro Asp Ser Leu Ala Asp Tyr Phe Lys
1               5                   10                  15

<210> SEQ ID NO 22
<211> LENGTH: 5
<212> TYPE: PRT
<213> ORGANISM: Homo sapiens

<400> SEQUENCE: 22

Ser Ile Phe Thr Arg
1               5

<210> SEQ ID NO 23
<211> LENGTH: 16
<212> TYPE: PRT
<213> ORGANISM: Homo sapiens
```

```
<400> SEQUENCE: 23

Leu Pro Gly Ser Tyr Asp Ser Thr Ser Ser Asp Ser Leu Tyr Pro Arg
1               5                   10                  15

<210> SEQ ID NO 24
<211> LENGTH: 5
<212> TYPE: PRT
<213> ORGANISM: Homo sapiens
<220> FEATURE:
<221> NAME/KEY: X
<222> LOCATION: (1)..(1)
<223> OTHER INFORMATION: X is unassigned

<400> SEQUENCE: 24

Xaa Tyr Val Asn Val
1               5

<210> SEQ ID NO 25
<211> LENGTH: 4
<212> TYPE: PRT
<213> ORGANISM: Homo sapiens

<400> SEQUENCE: 25

Tyr Val Asn Val
1

<210> SEQ ID NO 26
<211> LENGTH: 4
<212> TYPE: PRT
<213> ORGANISM: Homo sapiens

<400> SEQUENCE: 26

Tyr Leu Val Val
1
```